US010550110B2

(12) United States Patent
Musicki et al.

(10) Patent No.: US 10,550,110 B2
(45) Date of Patent: Feb. 4, 2020

(54) TETRAHYDROQUINOLINE SULFONAMIDE DERIVATIVES AS INVERSE AGONISTS OF RETINOID-RELATED ORPHAN RECEPTOR GAMMA (ROR GAMMA (T))

(71) Applicant: GALDERMA RESEARCH & DEVELOPMENT, Biot (FR)

(72) Inventors: Branislav Musicki, Nice (FR); Claire Bouix-Peter, Vallauris (FR); Gilles Ouvry, Biot (FR); Etienne Thoreau, Saint Vallier de Thiey (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 193 days.

(21) Appl. No.: 15/537,591

(22) PCT Filed: Dec. 18, 2015

(86) PCT No.: PCT/EP2015/080690
§ 371 (c)(1),
(2) Date: Jun. 19, 2017

(87) PCT Pub. No.: WO2016/097392
PCT Pub. Date: Jun. 23, 2016

(65) Prior Publication Data
US 2018/0265500 A1 Sep. 20, 2018

(30) Foreign Application Priority Data

Dec. 19, 2014 (FR) ...................................... 14 63035
Jul. 3, 2015 (FR) ...................................... 15 56341

(51) Int. Cl.

| | | |
|---|---|---|
| *C07D 413/06* | (2006.01) |
| *C07D 405/14* | (2006.01) |
| *C07D 215/36* | (2006.01) |
| *C07D 231/56* | (2006.01) |
| *C07D 401/04* | (2006.01) |
| *C07D 401/06* | (2006.01) |
| *C07D 403/04* | (2006.01) |
| *C07D 403/06* | (2006.01) |
| *C07D 405/04* | (2006.01) |
| *C07D 405/12* | (2006.01) |
| *C07D 407/04* | (2006.01) |
| *C07D 409/04* | (2006.01) |
| *C07D 409/06* | (2006.01) |
| *C07D 417/06* | (2006.01) |
| *C07D 471/10* | (2006.01) |
| *C07D 209/34* | (2006.01) |
| *C07D 307/79* | (2006.01) |
| *C07D 405/06* | (2006.01) |
| *A61P 17/10* | (2006.01) |
| *A61P 17/06* | (2006.01) |
| *A61P 17/04* | (2006.01) |
| *C07D 401/14* | (2006.01) |

(52) U.S. Cl.
CPC ............ *C07D 413/06* (2013.01); *A61P 17/04* (2018.01); *A61P 17/06* (2018.01); *A61P 17/10* (2018.01); *C07D 209/34* (2013.01); *C07D 215/36* (2013.01); *C07D 231/56* (2013.01); *C07D 307/79* (2013.01); *C07D 401/04* (2013.01); *C07D 401/06* (2013.01); *C07D 401/14* (2013.01); *C07D 403/04* (2013.01); *C07D 403/06* (2013.01); *C07D 405/04* (2013.01); *C07D 405/06* (2013.01); *C07D 405/12* (2013.01); *C07D 405/14* (2013.01); *C07D 407/04* (2013.01); *C07D 409/04* (2013.01); *C07D 409/06* (2013.01); *C07D 417/06* (2013.01); *C07D 471/10* (2013.01)

(58) Field of Classification Search
None
See application file for complete search history.

(56) References Cited

FOREIGN PATENT DOCUMENTS

| WO | 2006/052190 A1 | 5/2006 |
| WO | 2013/160418 A1 | 10/2013 |
| WO | 2014/090712 A1 | 6/2014 |

OTHER PUBLICATIONS

International Search Report dated Mar. 7, 2016 corresponding to International Patent Application No. PCT/EP2015/080690 (with English translation), 6 pages.
Zhang, Y., et al., "Discovery of 2-oxo-1,2-dihydrobenzo[cd]indole-6-sulfonamide derivatives as new RORγ inhibitors using virtual screening, synthesis and biological evaluation," European J. Med. Chem., vol. 78, Mar. 2014, pp. 431-444, XP028847891.

*Primary Examiner* — Heidi Reese
(74) *Attorney, Agent, or Firm* — Sunit Talapatra; Foley & Lardner LLP

(57) ABSTRACT

Tetrahydroquinoline sulfonamide derivatives of formula (I), the pharmaceutically acceptable addition salts thereof, the hydrates and/or solvates thereof, and the use of same as inverse agonists of retinoid-related orphan receptor gamma (RORγt) are described. Pharmaceutical compositions including such compounds, as well as the use thereof for the topical and/or oral treatment of RORγt receptor-mediated inflammatory diseases, in particular acne, psoriasis and/or atopic dermatitis are also described.

20 Claims, No Drawings

TETRAHYDROQUINOLINE SULFONAMIDE DERIVATIVES AS INVERSE AGONISTS OF RETINOID-RELATED ORPHAN RECEPTOR GAMMA (ROR GAMMA (T))

CROSS REFERNCE TO PRIOR APPLICATIONS

This application is a National Stage of PCT/Ep2015/080690, filed Dec. 18, 2015, and designating the United States (published Jun. 23, 2016, as WO 2016/097392 A1), which claims priority under 35 U.S.C. § 119 to French Patent Application No. 1463035, Dec. 19, 2014 and French Patent Application No. 1556341, filed Jul. 3, 2015, each hereby expressly incorporated by reference in its entirety and each assigned to the assignee hereof.

The present invention relates to particular bicyclic sulfonamide derivatives, to the pharmaceutically acceptable addition salts thereof, hydrates thereof and/or solvates thereof, and also to the use thereof as inverse agonist of the retinoid-related orphan receptor gamma RORγt.

The invention also relates to a pharmaceutical composition comprising such compounds and also to the use thereof for the topical and/or oral treatment of inflammatory diseases mediated by the RORγt receptors, especially acne, atopic dermatitis and/or psoriasis.

The nuclear receptors form a large family (known as a superfamily) of transcription factors which correspond to proteins that are capable of being activated by a ligand, of binding to specific DNA sequences and of regulating the transcription of target genes. Thus, these receptors are involved in the regulation of a wide variety of biological functions, including growth, development, reproduction, differentiation and metabolism in a multitude of living organisms.

The first members of this superfamily that were identified and described in the scientific literature are the nuclear receptors of steroid hormones such as the glucocorticoid receptors and the estrogen receptors. This superfamily also comprises among its members many receptors for which no ligand has been identified. These nuclear receptors are known as "orphan receptors".

Retinoid-related orphan receptors thus constitute a subfamily of nuclear receptors. This subfamily is composed of three members each having an intrinsic expression profile: ROR alpha (known as RORα), ROR beta (known as RORβ) and ROR gamma (known as RORγ). Two isoforms of the orphan receptors RORγ have already been identified, namely RORγ1, which is expressed in a variety of tissues such as the thymus, the kidneys, muscles and the liver, and RORγ2 (also known as RORγt), which is expressed exclusively in the cells of the immune system.

In particular, the receptor RORγt plays an important regulating role in cell differentiation of the Th17 lymphocytes which correspond to helper T lymphocytes whose function is to ensure the defense of the body against a large number of extracellular pathogens such as bacteria and fungal infections.

However, it has been demonstrated that the Th17 lymphocytes are also involved in a wide variety of inflammatory disorders, such as acne, and of autoimmune diseases such as psoriasis, rheumatoid arthritis or multiple sclerosis (Peck A, Mellins E D. Precarious balance; Th17 cells in host defense. Infect. Immun. 2010 January; 78(1): 32-8; Suarez-Farinas: J. Allergy Clin. Immunol. 2014; J. Invest. Dermatol. 2008, 128(11), 2625).

Specifically, the Th17 lymphocytes produce numerous cytokines which have distinct profiles, such as interleukin-17A (IL-17A), interleukin-17F (IL-17F), interleukin-26 (IL-26), interleukin-21 (IL-21), interleukin-22 (IL-22) and TNFα, the development, survival and proliferation of which depend on interleukin-23 (IL-23). These cytokines are capable of activating different types of effector cells, such as keratinocytes, thus leading to their hyperproliferation and to the additional production of pro-inflammatory cytokines, chemokines and antimicrobial peptides, which in turn recruit and activate other immune system cells in the inflamed skin, which may lead to amplification of the inflammatory response.

Thus, activation of the Th17 lymphocytes is responsible for the recruitment of cytokines, especially of interleukin-17 (IL17), and of other types of pro-inflammatory cells, which will lead to the mediation of inflammatory disorders such as acne and/or of autoimmune diseases such as psoriasis.

Experiments conducted on mice show that a decrease in the level of expression of the RORγt receptor leads to a decrease in the activity of the Th17 lymphocytes, which consequently makes it possible to greatly reduce the expression of interleukin-17 (IL-17) (Ivanov II, McKenzie BS, Zhou L, Tadokoro CE, Lepelley A, Lafaille JJ, Cua DJ, Littman DR: Cell 2006, 126, 1121-1133) and to efficiently treat inflammatory disorders and autoimmune diseases mediated by these cytokines, especially those for which high levels of interleukin-17 (IL-17) are detected.

To this end, patent application WO 2013/160 418 describes sulfonamide compounds used as inverse agonists of the RORγt receptor in order to be able to treat inflammatory disorders and autoimmune diseases. Similarly, other compounds have also been developed as inverse agonists of the RORγt receptor, such as those described in patent applications WO 2014/090 712, WO 2014/008 214, WO 2013/169 588, WO 2013/160 419, WO 2013/1 002 027, WO 2013/092 939, WO 2013/092 941, WO 2013/085 890 and WO 2012/100 732.

There is thus a real need to develop novel compounds as inverse agonists of the RORγt receptor in order to be able to efficiently treat diseases mediated by such a receptor, especially inflammatory disorders such as acne, and/or autoimmune diseases such as psoriasis or atopic dermatitis.

This aim is achieved by means of the use of particular bicyclic sulfonamide derivatives as described below, which make it possible to modulate the activity of the RORγt receptor and consequently to efficiently treat inflammatory disorders and autoimmune diseases of certain pathologies.

One subject of the present invention is thus one or more compounds of formula (I), the pharmaceutically acceptable addition salts thereof, hydrates thereof and/or solvates thereof:

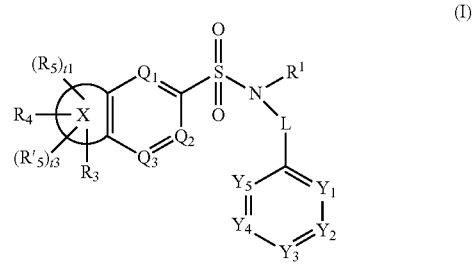

in which formula (I):
L represents a single bond or a methylene group $CH_2$,
X represents the following cyclic radical:

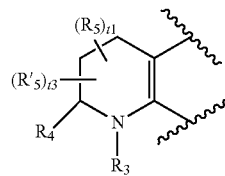

one or two of the elements $Y^1$, $Y^2$, $Y^3$, $Y^4$ and $Y^5$ represent(s) a nitrogen atom and the other elements correspond to a group —$CR^2$, or each of the elements $Y^1$, $Y^2$, $Y^3$, $Y^4$ and $Y^5$ corresponds to a group —$CR^2$, one or two of the elements $Q^1$, $Q^2$ and $Q^3$ represent(s) a nitrogen atom and the other element(s) correspond(s) to a group —$CR^{2a}$, or each of the elements $Q^1$, $Q^2$ and $Q^3$ corresponds to a group —$CR^{2a}$, $R^1$ represents a linear or branched $C_3$-$C_5$ alkyl radical, a $C_3$-$C_5$ cycloalkyl radical, a linear or branched $C_2$-$C_5$ alkenyl radical, a ($C_1$)alkyl($C_3$-$C_5$)cycloalkyl radical, a $C_4$-$C_5$ heterocycloalkyl radical, a ($C_1$)alkyl($C_4$-$C_6$)heterocycloalkyl radical, $R^2$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a cyano group —CN, a radical —C(=O)$R'^2$ with $R'^2$ denoting a $C_1$-$C_3$ alkoxy radical, a —$CF_3$ radical; said alkyl, alkenyl and alkoxy radicals possibly being substituted with one or more halogen atoms, $R^{2a}$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a —CN group, a hydroxyl group —OH, a group —CH($R^{3a}$)OH, a carboxylic group —COOH, a carbamoyl group —CONR$^{2c}$R$^{2d}$, an amido group —NR$^{2c}$COR$^{2d}$, a group —SO$_2$R$^{2c}$, a group —SOR$^{2c}$, a group —S(=O)(=NH—R$^{2c}$), said alkyl, alkenyl and alkoxy radicals possibly being substituted with one or more halogen atoms, $R^{2c}$ and $R^{2d}$, which may be identical or different, represent a hydrogen atom or a linear or branched $C_1$-$C_5$ alkyl radical, $R^{3a}$ represents a hydrogen atom or a linear or branched $C_1$-$C_5$ alkyl radical, $t_1$ and $t_3$, which may be identical or different, denote a natural integer 0 or 1, $R^3$ and $R^4$, which may be identical or different, represent a hydrogen atom, a group (CHR$^6$)$_n$—(Z)$_o$—(CHR$'^6$)$_p$—R$^7$, a group CH=R$^7$ or a group —C=CH—R$^7$, n, o and p, which may be identical or different, represent zero or a natural integer ranging from 1 to 3, when $R^3$ represents a group (CHR$^6$)$_n$—(Z)$_o$—(CHR$'^6$)$_p$—R$^7$, a group CH=R$^7$ or a group —C=CH—R$^7$, then $R^4$ represents a hydrogen atom, when $R^4$ represents a group (CHR$^6$)$_n$—(Z)$_o$—(CHR$'^6$)$_p$—R$^7$, a group CH=R$^7$ or a group —C=CH—R$^7$, then $R^3$ represents a hydrogen atom, Z represents a divalent group chosen from a methylene group —CH$_2$—, an amino group —NH— and an oxygen atom —O—, $R^6$ and $R'^6$, which may be identical or different, represent a hydrogen atom, a methyl group —CH$_3$, an —OH group, a $C_1$ hydroxyalkyl group, a carboxylic function —COOH, $R^7$ represents:
a hydrogen atom or a halogen atom,
a group COOR$'^7$ with R$'^7$ denoting (C$_1$)alkyl(C$_6$)heterocycle,
a non-cationic heterocyclic radical optionally substituted with one or more halogen atoms, one or more linear or branched C$_1$-C$_3$ alkyl groups, one or more —OH groups, one or more carbonyl functions, one or more linear or branched C$_1$-C$_4$ hydroxyalkyl groups, one or more amino groups, one or more groups —C(=O)R$^{7a}$, one or more groups S(=O)$_2$R$^{7a}$; R$^{7a}$ representing a linear or branched C$_1$-C$_3$ alkyl radical, a linear or branched C$_1$-C$_3$ alkoxy radical, or an amino radical N(R$^{8a}$)(R$^{8b}$),
a non-cationic C$_3$-C$_6$ cycloalkyl radical optionally substituted with one or more C$_1$ alkyl radicals, one or more halogen atoms, a cyano group —CN or one or more groups —COR$^9$; R$^9$ denoting a linear or branched C$_1$-C$_3$ alkoxy radical, or a hydroxyl group,
an aromatic or heteroaromatic, non-cationic radical optionally substituted with one or more halogen atoms, one or more linear or branched C$_1$-C$_3$ alkyl groups optionally substituted with one or more halogen atoms, one or more C$_1$-C$_3$ alkoxy groups, one or more amino groups —NR$^{11}$R$^{12}$, one or more groups —COR$^{11}$, one or more groups —COOR$^{11}$, one or more amido groups —CONR$^{11}$R$^{12}$, one or more groups —SOR$^{11}$, one or more groups —SO$_2$R$^{11}$, one or more groups —NHCOR$^{11}$, one or more groups —NHCOOR$^{11}$, one or more groups —SO$_2$NR$^{11}$R$^{12}$ or one or more —CN groups; R$^{11}$ and R$^{12}$, which may be identical or different, representing a hydrogen atom, a hydroxyl radical —OH, a linear or branched C$_1$-C$_3$ alkyl radical optionally substituted with one or more halogen atoms;

when $R^3$ or $R^4$ represents a group —CH=R$^7$ or a group —C=CH—R$^7$, then R$^7$ does not represent a hydrogen atom, a halogen atom or a group COOR$'^7$, $R^5$ represents a hydrogen atom or a halogen atom, a linear or branched C$_1$-C$_3$ alkyl radical optionally substituted with one or more halogen atoms; an amino radical —NH$_2$, a radical CH$_2$R$'^{7a}$ with R$'^{7a}$ denoting a C$_1$ alkoxy radical, a hydroxyl group —OH, a —CH$_2$COOH group, a group —CH(R$^{5b}$)OH, an amino group —NH$_2$, a carboxylic group —COOH, a —CN group, a thioxo function, $R'_5$ represents a carbonyl function (C=O) or a thioxo function (C=S), $R^{8a}$ and $R^{8b}$, which may be identical or different, denote a hydrogen atom, a linear or branched C$_1$-C$_3$ alkyl radical or a cyclopropyl radical.

The compound(s) according to the invention thus correspond to bicyclic sulfonamide derivatives, and thus to one or more sulfonamide compounds bearing in their structure at least two rings that are fused to each other.

In accordance with formula (I) according to the invention, the endocyclic bond between the cyclic radical X, as represented above, and the aromatic nucleus comprising the elements Q$_1$ to Q$_3$ is a double bond common to the two rings.

The compounds according to the invention make it possible to modulate, i.e. to inhibit, the activity of the RORγt receptor.

A subject of the present invention is also the compound(s) as defined previously, as medicament and cosmetic.

Another subject of the invention relates to the compound(s) as defined previously for their use in the treatment of diseases mediated by the RORγt receptor, especially inflammatory disorders and/or autoimmune diseases mediated by the RORγt receptor.

Moreover, the invention also relates to a pharmaceutical composition comprising, in a pharmaceutically acceptable medium, one or more compounds of formula (Ia) as defined previously, pharmaceutically acceptable addition salts thereof, hydrates thereof and/or solvates thereof.

The present invention also relates to the pharmaceutical composition as described previously, for its use in the treatment of diseases mediated by the RORγt receptor, especially inflammatory disorders and/or autoimmune diseases.

Finally, the invention relates to a method for treating diseases mediated by the RORγt receptor, comprising the administration, especially topically or orally, of a therapeutically effective amount of one or more compounds as defined above to a patient.

Other subjects, characteristics, aspects and advantages of the invention will emerge even more clearly on reading the description and the examples that follow.

According to one embodiment, in formula (I), L represents a single bond.

According to another embodiment, in formula (I), L represents a methylene group —$CH_2$.

Preferentially, in formula (I), L represents a single bond.

Preferably, $R^5$ represents a hydroxyl group —OH, a group —$CH(R^{5b})OH$, an amino group —$NH_2$, a carboxylic group —COOH, a halogen atom or a —CN group.

Preferentially, $R^3$ and $R^4$, which may be identical or different, represent a hydrogen atom or a group $(CHR^6)_n$—$(Z)_o$—$(CHR'^6)_p$—$R^7$.

According to one embodiment, in formula (I), $R^3$ and $R^4$ represent a hydrogen atom.

According to one embodiment, in formula (I), $R^3$ represents a group $(CHR^6)_n$—$(Z)_o$—$(CHR'^6)_p$—$R^7$ and $R^4$ represents a hydrogen atom.

According to one embodiment, in formula (I), $R^3$ represents a hydrogen atom and $R^4$ represents a group $(CHR^6)_n$—$(Z)_o$—$(CHR'^6)_p$—$R^7$.

Preferably, $R^{11}$ and $R^{12}$ are other than an —OH group.

According to one embodiment, in formula (I), the indices n, o and p, which may be identical or different, denote zero.

According to one embodiment, in formula (I), the indices n, o and p, which may be identical or different, denote a natural integer ranging from 1 to 3.

According to one embodiment, in formula (I), the indices n and p denote zero and the index o is equal to 1.

According to one embodiment, in formula (I), Z represents a methylene group —$CH_2$.

According to one embodiment, in formula (I), Z represents a divalent group —O—.

According to one embodiment, in formula (I), Z represents a divalent group —NH—.

According to one embodiment, in formula (I), $R^3$ represents a group Z—$R^7$, with Z having the meaning described previously.

According to a particular embodiment, in formula (I), $R^3$ represents a group —$CH_2$—$R^7$.

According to a particular embodiment, in formula (I), $R^3$ represents a group —O—$R^7$.

According to a particular embodiment, in formula (I), $R^3$ represents a group —NH—$R^7$.

According to one embodiment, in formula (I), $R^7$ represents a heterocyclic radical chosen from the following heterocycles:

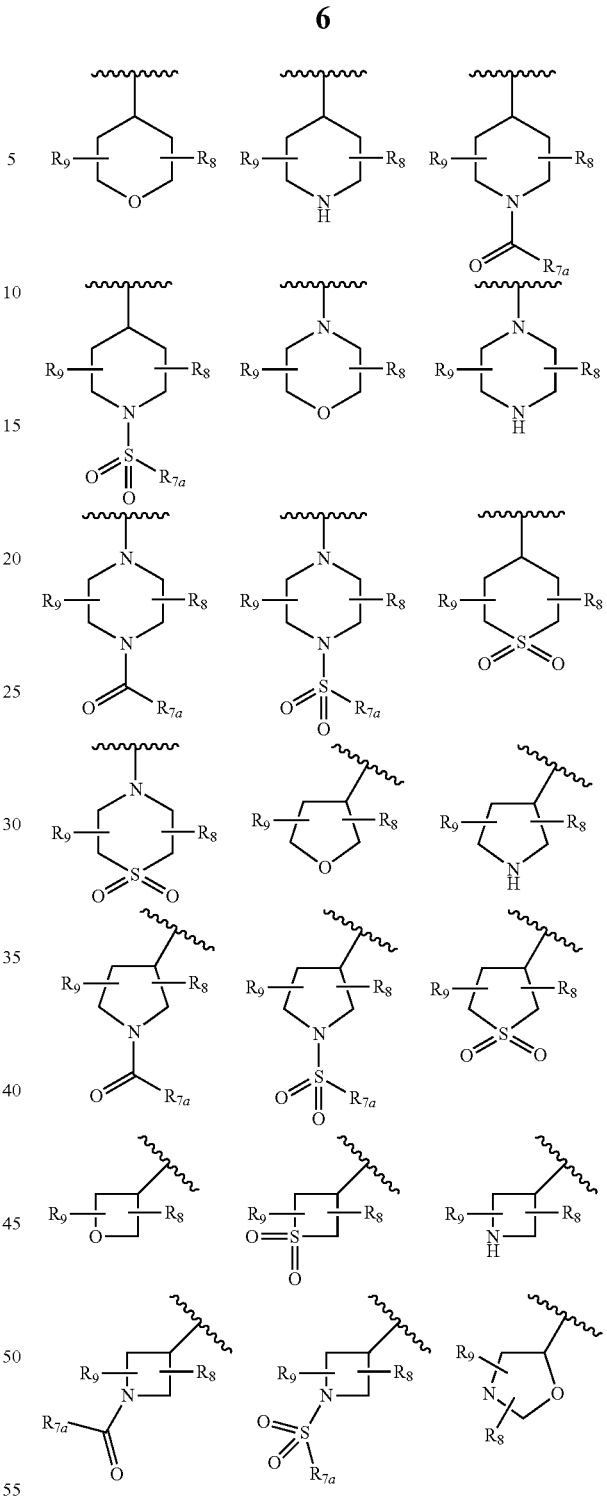

in which:
$R_{7a}$ represents a linear or branched $C_1$-$C_3$ alkyl radical, a $C_1$-$C_3$ alkoxy radical or an amino radical $N(R^{8a})(R^{8b})$,
$R^{8a}$ and $R^{8b}$, which may be identical or different, denote a hydrogen atom, a linear or branched $C_1$-$C_3$ alkyl radical or a cyclopropyl radical,
$R_8$ and $R_9$, which may be identical or different, represent a hydrogen atom, a linear or branched $C_1$-$C_3$ alkyl radical, a hydroxyl group —OH, a carbonyl function =O, a ($C_1$)hydroxyalkyl radical (—$CH_2OH$), an amino group $NH_2$, $R_8$ and $R_9$ can form, together with the carbon atoms to which they are attached, a 5- to 7-membered carbocyclic ring.

According to one embodiment, $R^7$ may also represent a spiro bicyclic radical comprising a heteroatom.

According to one embodiment, in formula (I), $R^7$ represents an aromatic or heteroaromatic radical chosen from:

[structures shown with $(R_{10})_m$ substituents]

in which:
$R_{10}$ represents a hydrogen atom or a halogen atom, one linear or branched $C_1$-$C_3$ alkyl group optionally substituted with one or more halogen atoms, one $C_1$-$C_3$ alkoxy group, one amino group —$NR^{11}R^{12}$, one group —$COR^{11}$, one group —$COOR^{11}$, one amido group —$CONR^{11}R^{12}$, one group —$SOR^{11}$, one group —$SO_2R^{11}$, one group —$NHCOR^{11}$, one group —$NHCOOR^{11}$, one group —$SO_2NR^{11}R^{12}$ or one —CN group; $R^{11}$ and $R^{12}$, which may be identical or different, representing a hydrogen atom or a linear or branched $C_1$-$C_3$ alkyl radical optionally substituted with one or more halogen atoms, m denotes zero or a natural integer ranging from 1 to 3.
Preferably, $R^{11}$ and $R^{12}$ are other than an —OH group.
Preferentially, $R^7$ represents an aromatic or heteroaromatic radical as defined previously, optionally substituted with one or more methyl groups —$CH_3$, one or more methoxy groups —$OCH_3$, one or more hydroxyl groups —OH, one or more amino groups —$NH_2$, one or more —$CH_2OH$ groups, one or more cyano groups —CN, one or more halogen atoms or one or more carbonyl functions.

According to one embodiment, the index m is equal to zero.

According to one embodiment, the index m denotes a natural integer ranging from 1 to 3.

Preferentially, the index m is equal to 1.

According to one embodiment, in formula (I), each of the elements $Y^1$, $Y^2$, $Y^3$, $Y^4$ and $Y^5$ corresponds to a group —$CR^2$ with $R^2$ having the same meaning as that described previously.

According to one embodiment, in formula (I), each of the elements $Y^1$, $Y^2$, $Y^3$, $Y^4$ and $Y^5$ corresponds to a group —$CR^2$ with $R^2$ representing a hydrogen atom.

According to one embodiment, in formula (I), each of the elements $Y^1$, $Y^2$, $Y^3$, $Y^4$ and $Y^5$ corresponds to a group —$CR^2$ with $R^2$ representing a linear or branched $C_1$-$C_5$ alkyl radical.

According to one embodiment, in formula (I), each of the elements $Q^1$, $Q^2$ and $Q^3$ represents a group —$CR^{2a}$ with $R^{2a}$ having the same meaning as that described previously.

According to one embodiment, in formula (I), each of the elements $Q^1$, $Q^2$ and $Q^3$ represents a group —$CR^{2a}$ with $R^{2a}$ representing a hydrogen atom.

According to one embodiment, in formula (I), $Q^1$ and $Q^2$ represent a group —$CR^{2a}$ with $R^{2a}$ representing a hydrogen atom and $Q^3$ represents a group —$CR^{2a}$ with $R^{2a}$ representing a linear or branched $C_1$-$C_5$ alkyl radical.

According to one embodiment, in formula (I), $R^1$ represents a linear or branched $C_3$-$C_5$ alkyl radical, preferably a branched $C_3$-$C_5$ and more preferentially branched $C_4$ alkyl radical.

According to one embodiment, in formula (I), $R^1$ represents a $C_3$-$C_5$ cycloalkyl radical, preferably cyclopropyl.

According to one embodiment, in formula (I), $R^1$ represents a linear or branched $C_2$-$C_5$ alkenyl radical.

According to one embodiment, in formula (I), $R^1$ represents a $CH_2$—($C_3$-$C_5$)cycloalkyl radical.

According to one embodiment, in formula (I), $R^1$ represents a $C_4$-$C_5$ heterocycloalkyl radical.

According to one embodiment, in formula (I), $R^1$ represents a $CH_2$—($C_4$-$C_6$)heterocycloalkyl radical, in particular a $CH_2$—($C_4$-$C_5$)heterocycloalkyl radical.

Preferentially, $R^1$ represents a linear or branched $C_3$-$C_5$ alkyl radical, or a $CH_2$—($C_4$-$C_5$)heterocycloalkyl radical.

According to one embodiment, $R^5$ represents a hydrogen atom.

According to one embodiment, $R'^5$ represents a carbonyl function (C=O).

More preferentially, $R^3$ represents a group $CH_2$—$R^7$.

Preferably, the compound(s) of formula (I) are chosen from the compound(s) of formula (V), the pharmaceutically acceptable addition salts thereof, hydrates thereof and/or solvates thereof:

(V)

[structure]

in which formula (V), $R^1$, $R^3$, $R^4$, $R^5$, $R'^5$ and $Y^1$ to $Y^5$, and the indices $t_1$ and $t_3$ have the same meanings as in formula (I) described previously.

Preferentially, in formula (V), $R^4$ denotes a hydrogen atom.

Preferentially, in formula (V), when $t_1$ is equal to zero, then $t_3$ is equal to 1, and reciprocally, when $t_1$ is equal to 1, then $t_3$ denotes zero.

According to one embodiment, $R'^5$ denotes a carbonyl function.

According to one embodiment, $R^5$ represents a hydroxyl group —OH.

In accordance with these two embodiments, $R^4$ preferentially denotes a hydrogen atom.

According to a preferred embodiment, the compound(s) of formula (V) are chosen from the compounds of formula (V'):

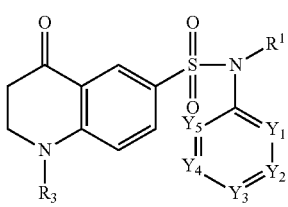

(V')

in which formula (V') $R^1$, $R^3$, and $Y^1$ to $Y^5$ have the same meanings as in formula (I) described previously.

In this embodiment, $t_1$ is equal to zero, $t_3$ is equal to 1, $R'^5$ denotes a carbonyl function and $R^4$ represents a hydrogen atom.

Preferentially, $R^3$ represents a group $CH_2$—$R^7$.

According to a preferred embodiment, the compound(s) of formula (V) are also chosen from the compound(s) of formula (V"):

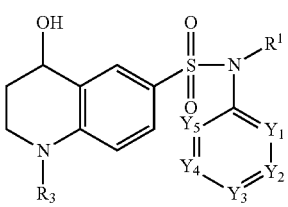

(V")

in which formula (V") $R^1$, $R^3$ and $Y^1$ to $Y^5$ have the same meanings as in formula described previously.

In this embodiment, $t_1$ is equal to 1, $t_3$ is equal to zero, $R^5$ denotes a hydroxyl group —OH and $R^4$ represents a hydrogen atom.

Preferentially, $R^3$ represents a group $CH_2$—$R^7$.

Thus, the compound(s) of formula (I) according to the invention is(are) chosen from the compound(s) of formula (V).

The compounds of formula (I) may be in the form of pharmaceutically acceptable salts. Examples of pharmaceutically acceptable salts are described in Berge et al., 1977, "Sels pharmaceutiquement acceptables" [Pharmaceutically acceptable salts], J. Pharm. Sci., Vol. 66, pages 1-19.

In particular, when the compounds of formula according to the invention are in the form of salts, then the electrical neutrality of said compounds is ensured by an external cationic counterion Y which may be organic or mineral.

Y may be chosen from suitable inorganic cations such as alkali metal ions, especially $Na^+$, $K^+$, alkaline-earth metal ions, especially $Ca^{2+}$, $Mg^{2+}$, or alternatively other cations such as the aluminum ion $Al^{3+}$.

Y may be chosen from suitable organic cations such as the ammonium ion $NH_4^+$, substituted ammonium ions such as $NH_3R^+$, $NHR_2^+$, $NR_4^+$ with R representing a $C_1$-$C_4$ alkyl radical.

In particular, the substituted ammonium ions are those chosen from derivatives of ethylamine, diethylamine, dicyclohexylamine, triethylamine, butylamine, ethylenediamine, ethanolamine, diethanolamine, piperazine, benzylamine, phenylbenzylamine, choline, meglumine and tromethamine, and amino acids such as lysine and arginine.

An example of a quaternary ammonium ion may be the ion $N^+$ $(CH_3)_4$.

The compound(s) according to the invention may be in the form of the solvates thereof.

For the purposes of the present invention, the term "solvate" means a complex of solute (i.e. the compound according to the invention or the salt of said compound) and of solvent.

If the solvent is water, then the solvate may suitably be considered as a hydrate, for example, a hemihydrate, a monohydrate, a dihydrate, a trihydrate, etc.

For example, the solvates and/or hydrates may be obtained directly at the end of the synthetic process, the target compound being isolated in the form of a hydrate, for example a monohydrate or hemihydrate, or in the form of a solvate of the reaction and/or purification solvent.

Unless otherwise indicated, any reference to a compound according to the invention also includes the solvate or the hydrate of the corresponding compound.

Typical processes for the preparation and identification of hydrates and solvates are well known to those skilled in the art: see, for example, pages 202-209 of KJ Guillory, "Generation of Polymorphs, Hydrates, Solvates, and Amorphous Solids" in Polymorphism in Pharmaceutical Solids, edition. Harry G. Britain, Vol. 95, Marcel Dekker, Inc., New York, 1999.

The hydrates and solvates may be isolated and characterized via methods known in the art, such as thermogravimetric analysis (TGA), TGA-mass spectroscopy, TGA-infrared spectroscopy, x-ray powder diffraction, Karl Fischer titration, high-resolution x-ray diffraction, and the like.

Preferably, the compound(s) of formula (I) are chosen from the compounds as described in the tables below, and also the pharmaceutically acceptable addition salts thereof, hydrates thereof and/or solvates thereof:

TABLE 1

| | | IC50 hRORg | IC50 hCD4/IL17 |
|---|---|---|---|
| (structure) | 4-oxo-1-(tetrahydropyran-4-ylmethyl)-1,2,3,4-tetrahydroquinoline-6-sulfonic acid (4-ethylphenyl)isobutylamide<br>Compound 1 | B | B |
| (structure) | 4-hydroxy-1-(tetrahydropyran-4-ylmethyl)-1,2,3,4-tetrahydroquinoline-6-sulfonic acid (4-ethylphenyl)isobutylamide<br>Compound 2 | A | B |
| Enantiomer 1 | | A | A |
| Enantiomer 2 | | B | A |
| (structure) | 4-oxo-1-(5-oxopyrrolidin-2-ylmethyl)-1,2,3,4-tetrahydroquinoline-6-sulfonic acid (4-ethylphenyl)isobutylamide<br>Compound 3 | C | ND |
| (structure) | 4-oxo-1-pyridin-4-ylmethyl-1,2,3,4-tetrahydroquinoline-6-sulfonic acid (4-ethylphenyl)isobutylamide<br>Compound 4 | A | A |
| (structure) | tert-butyl ester of 4-{6-[(4-ethylphenyl)isobutylsulfamoyl]-4-oxo-3,4-dihydro-2H-quinolin-1-ylmethyl}piperidine-1-carboxylic acid<br>Compound 5 | C | ND |

TABLE 1-continued

| | IC50 hRORg | IC50 hCD4/IL17 |
|---|---|---|
| 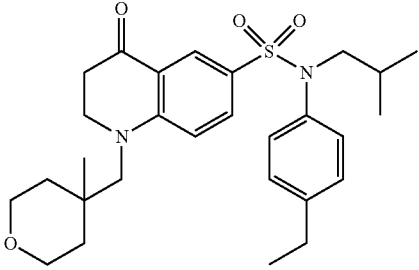 [SMILES: CCc1ccc(N(CC(C)C)S(=O)(=O)c2ccc3c(c2)C(=O)CCN3CC2(C)CCOCC2)cc1] 1-(4-methyltetrahydropyran-4-ylmethyl)-4-oxo-1,2,3,4-tetrahydroquinoline-6-sulfonic acid (4-ethylphenyl)isobutylamide Compound 6 | B | ND |
| 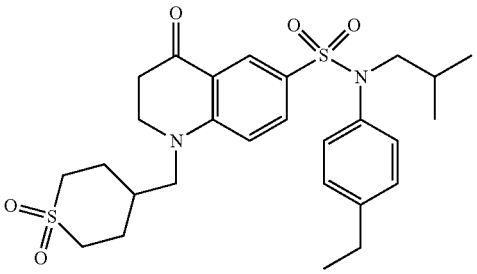 [SMILES: CCc1ccc(N(CC(C)C)S(=O)(=O)c2ccc3c(c2)C(=O)CCN3CC2CCS(=O)(=O)CC2)cc1] 1-(1,1-dioxohexahydro-1$\lambda^6$-thiopyran-4-ylmethyl)-4-oxo-1,2,3,4-tetrahydroquinoline-6-sulfonic acid (4-ethylphenyl)isobutylamide Compound 7 | C | ND |
| 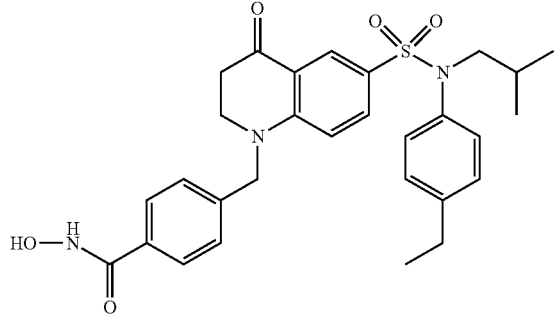 [SMILES: CCc1ccc(N(CC(C)C)S(=O)(=O)c2ccc3c(c2)C(=O)CCN3Cc2ccc(C(=O)NO)cc2)cc1] 4-{6-[(4-ethylphenyl)isobutylsulfamoyl]-4-oxo-3,4-dihydro-2H-quinolin-1-ylmethyl}-N-hydroxybenzamide Compound 8 | C | ND |
| 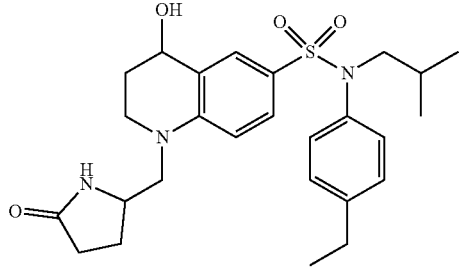 4-hydroxy-1-(5-oxopyrrolidin-2-ylmethyl)-1,2,3,4-tetrahydroquinoline-6-sulfonic acid (4-ethylphenyl)isobutylamide Compound 9 | B | ND |
| 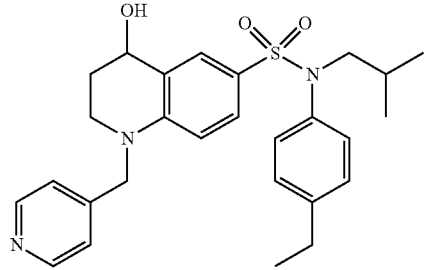 [SMILES: CCc1ccc(N(CC(C)C)S(=O)(=O)c2ccc3c(c2)C(O)CCN3Cc2ccncc2)cc1] 4-hydroxy-1-pyridin-4-ylmethyl-1,2,3,4-tetrahydroquinoline-6-sulfonic acid (4-ethylphenyl)isobutylamide Compound 10 | A | A |

TABLE 1-continued

| | | IC50 hRORg | IC50 hCD4/IL17 |
|---|---|---|---|
| 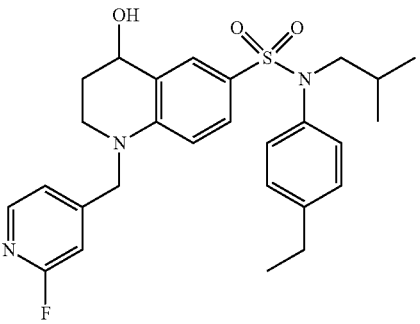 [SMILES: CCc1ccc(N(CC(C)C)S(=O)(=O)c2ccc3c(c2)C(O)CCN3Cc2ccnc(F)c2)cc1] | 1-(2-fluoropyridin-4-ylmethyl)-4-hydroxy-1,2,3,4-tetrahydroquinoline-6-sulfonic acid (4-ethylphenyl)isobutylamide<br>Compound 11 | A | A |
| 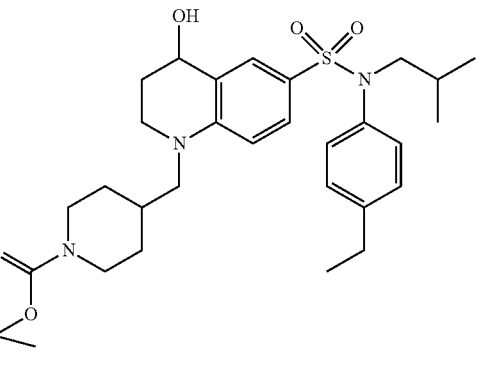 | tert-butyl ester of 4-{6-[(4-ethylphenyl)isobutylsulfamoyl]-4-hydroxy-3,4-dihydro-2H-quinolin-1-ylmethyl}piperidine-1-carboxylic acid<br>Compound 12 | C | ND |
| 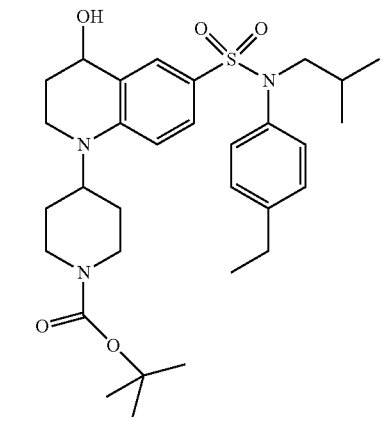 [SMILES: CCc1ccc(N(CC(C)C)S(=O)(=O)c2ccc3c(c2)C(O)CCN3C2CCN(C(=O)OC(C)(C)C)CC2)cc1] | tert-butyl ester of 4-{6-[(4-ethylphenyl)isobutylsulfamoyl]-4-hydroxy-3,4-dihydro-2H-quinolin-1-yl}piperidine-1-carboxylic acid<br>Compound 13 | C | ND |
| 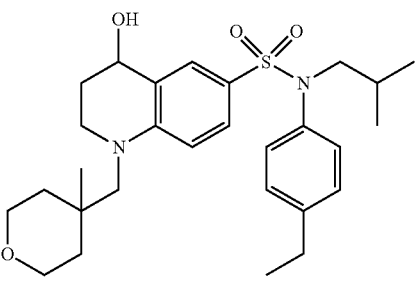 [SMILES: CCc1ccc(N(CC(C)C)S(=O)(=O)c2ccc3c(c2)C(O)CCN3CC2(C)CCOCC2)cc1] | 1-(4-methyltetrahydropyran-4-ylmethyl)-4-hydroxy-1,2,3,4-tetrahydroquinoline-6-sulfonic acid (4-ethylphenyl)isobutylamide<br>Compound 14 | A | A |

TABLE 1-continued

| | | IC50 hRORg | IC50 hCD4/IL17 |
|---|---|---|---|
| 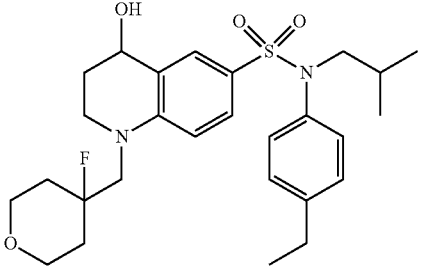 | 1-(4-fluorotetrahydropyran-4-ylmethyl)-4-hydroxy-1,2,3,4-tetrahydroquinoline-6-sulfonic acid (4-ethylphenyl)isobutylamide Compound 15 | B | A |
| 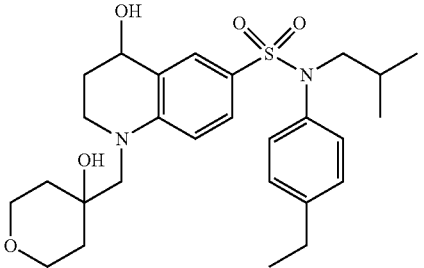 [SMILES: CCc1ccc(N(CC(C)C)S(=O)(=O)c2ccc3c(c2)C(O)CCN3CC2(O)CCOCC2)cc1] | 4-hydroxy-1-(4-hydroxytetrahydropyran-4-ylmethyl)-1,2,3,4-tetrahydroquinoline-6-sulfonic acid (4-ethylphenyl)isobutylamide Compound 16 | C | ND |
| 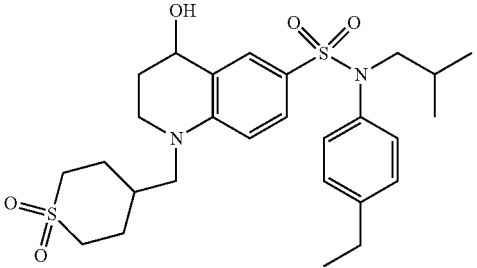 [SMILES: CCc1ccc(N(CC(C)C)S(=O)(=O)c2ccc3c(c2)C(O)CCN3CC2CCS(=O)(=O)CC2)cc1] | 1-(1,1-dioxohexahydro-1$\lambda^6$-thiopyran-4-ylmethyl)-4-hydroxy-1,2,3,4-tetrahydroquinoline-6-sulfonic acid (4-ethylphenyl)isobutylamide Compound 17 | C | ND |
| 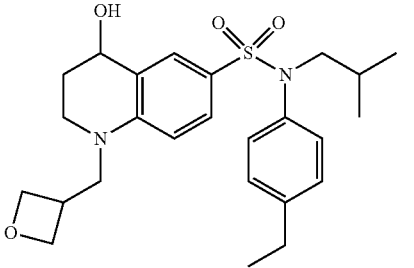 [SMILES: CCc1ccc(N(CC(C)C)S(=O)(=O)c2ccc3c(c2)C(O)CCN3CC2COC2)cc1] | 4-hydroxy-1-oxetan-3-ylmethyl-1,2,3,4-tetrahydroquinoline-6-sulfonic acid (4-ethylphenyl)isobutylamide Compound 18 | B | ND |
| 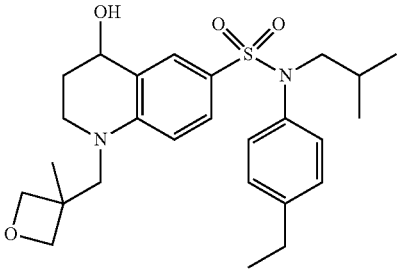 [SMILES: CCc1ccc(N(CC(C)C)S(=O)(=O)c2ccc3c(c2)C(O)CCN3CC2(C)COC2)cc1] | 4-hydroxy-1-(3-methyloxetan-3-ylmethyl)-1,2,3,4-tetrahydroquinoline-6-sulfonic acid (4-ethylphenyl)isobutylamide Compound 19 | B | A |

TABLE 1-continued

| | | IC50 hRORg | IC50 hCD4/IL17 |
|---|---|---|---|
| 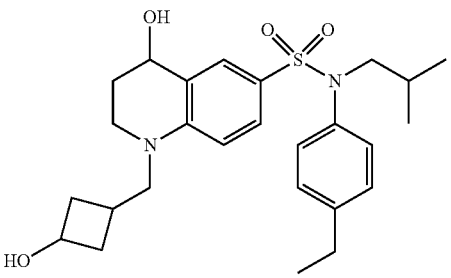 [SMILES: CCc1ccc(N(CC(C)C)S(=O)(=O)c2ccc3c(c2)C(O)CCN3CC2CC(O)C2)cc1] | 4-hydroxy-1-(3-hydroxycyclobutylmethyl)-1,2,3,4-tetrahydroquinoline-6-sulfonic acid (4-ethylphenyl)isobutylamide mixture of diastereoisomers: Compound 20 | B | A |
| 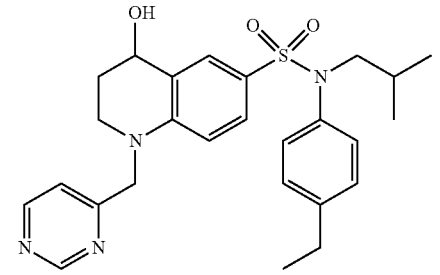 | 4-hydroxy-1-pyrimidin-4-ylmethyl-1,2,3,4-tetrahydroquinoline-6-sulfonic acid (4-ethylphenyl)isobutylamide Compound 21 | A | ND |
| 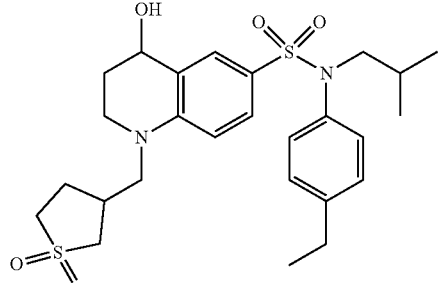 | 1-(1,1-dioxotetrahydro-1$\lambda^6$-thiophen-3-ylmethyl)-4-hydroxy-1,2,3,4-tetrahydroquinoline-6-sulfonic acid (4-ethylphenyl)isobutylamide Compound 22 | B | ND |
| 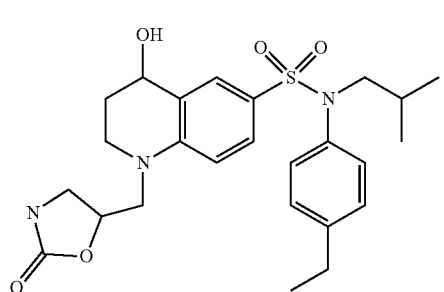 [SMILES: CCc1ccc(N(CC(C)C)S(=O)(=O)c2ccc3c(c2)C(O)CCN3CC2CNC(=O)O2)cc1] | 4-hydroxy-1-(2-oxooxazolidin-5-ylmethyl)-1,2,3,4-tetrahydroquinoline-6-sulfonic acid (4-ethylphenyl)isobutylamide Compound 23 | B | ND |
| 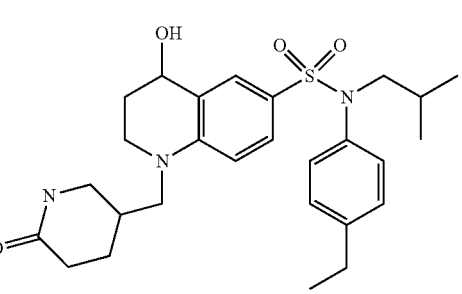 | 4-hydroxy-1-(6-oxopiperidin-3-ylmethyl)-1,2,3,4-tetrahydroquinoline-6-sulfonic acid (4-ethylphenyl)isobutylamide Compound 24 | B | ND |

TABLE 1-continued

| | | IC50 hRORg | IC50 hCD4/IL17 |
|---|---|---|---|
| 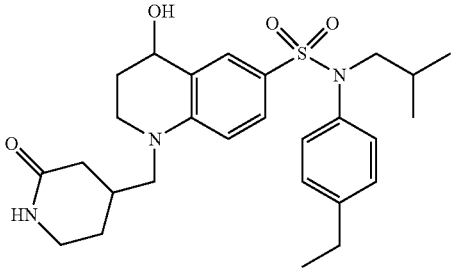 [SMILES: CCc1ccc(N(CC(C)C)S(=O)(=O)c2ccc3c(c2)C(O)CCN3CC2CCNC(=O)C2)cc1] | 4-hydroxy-1-(2-oxopiperidin-4-ylmethyl)-1,2,3,4-tetrahydroquinoline-6-sulfonic acid (4-ethylphenyl)isobutylamide Compound 25 | C | ND |
| 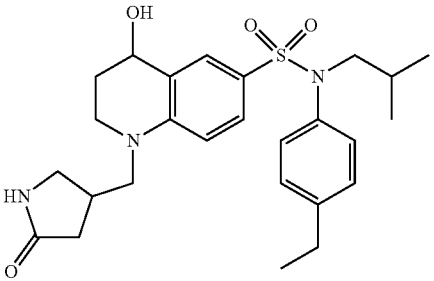 [SMILES: CCc1ccc(N(CC(C)C)S(=O)(=O)c2ccc3c(c2)C(O)CCN3CC2CNC(=O)C2)cc1] | 4-hydroxy-1-(5-oxopyrrolidin-3-ylmethyl)-1,2,3,4-tetrahydroquinoline-6-sulfonic acid (4-ethylphenyl)isobutylamide Compound 26 | B | ND |
| 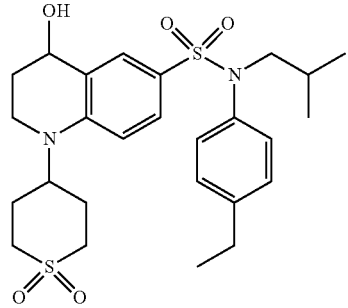 [SMILES: CCc1ccc(N(CC(C)C)S(=O)(=O)c2ccc3c(c2)C(O)CCN3C2CCS(=O)(=O)CC2)cc1] | 1-(1,1-dioxohexahydro-1$\lambda^6$-thiopyran-4-yl)-4-hydroxy-1,2,3,4-tetrahydroquinoline-6-sulfonic acid (4-ethylphenyl)isobutylamide Compound 27 | B | ND |
| 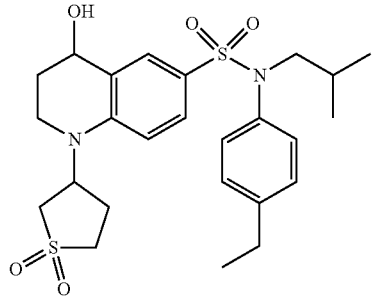 [SMILES: CCc1ccc(N(CC(C)C)S(=O)(=O)c2ccc3c(c2)C(O)CCN3C2CCS(=O)(=O)C2)cc1] | 1-(1,1-dioxotetrahydro-1$\lambda^6$-thiophen-3-yl)-4-hydroxy-1,2,3,4-tetrahydroquinoline-6-sulfonic acid (4-ethylphenyl)isobutylamide Compound 28 | B | ND |
| 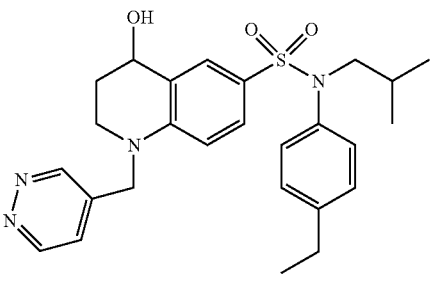 [SMILES: CCc1ccc(N(CC(C)C)S(=O)(=O)c2ccc3c(c2)C(O)CCN3Cc2ccnnc2)cc1] | 4-hydroxy-1-pyridazin-4-ylmethyl-1,2,3,4-tetrahydroquinoline-6-sulfonic acid (4 ethylphenyl)isobutylamide Compound 29 | A | A |

TABLE 1-continued

| | | IC50 hRORg | IC50 hCD4/IL17 |
|---|---|---|---|
| 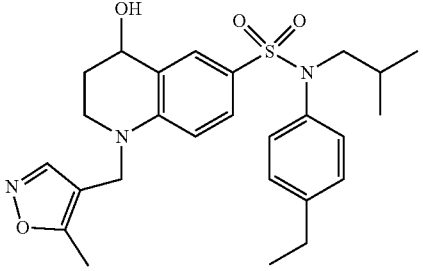 [SMILES: CCc1ccc(N(CC(C)C)S(=O)(=O)c2ccc3c(c2)C(O)CCN3Cc2cnoc2C)cc1] | 4-hydroxy-1-(5-methylisoxazol-4-ylmethyl)-1,2,3,4-tetrahydroquinoline-6-sulfonic acid (4-ethylphenyl)isobutylamide Compound 30 | B | ND |
| 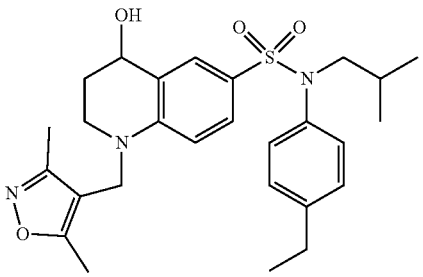 [SMILES: CCc1ccc(N(CC(C)C)S(=O)(=O)c2ccc3c(c2)C(O)CCN3Cc2c(C)noc2C)cc1] | 1-(3,5-dimethylisoxazol-4-ylmethyl)-4-hydroxy-1,2,3,4-tetrahydroquinoline-6-sulfonic acid (4-ethylphenyl)isobutylamide Compound 31 | B | ND |
| 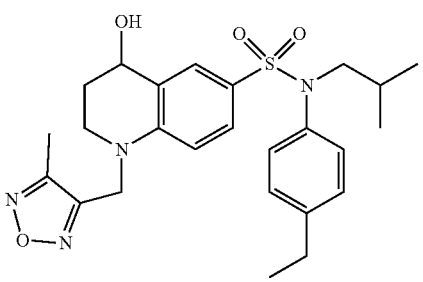 [SMILES: CCc1ccc(N(CC(C)C)S(=O)(=O)c2ccc3c(c2)C(O)CCN3Cc2nonc2C)cc1] | 4-hydroxy-1-(4-methylfurazan-3-ylmethyl)-1,2,3,4-tetrahydroquinoline-6-sulfonic acid (4-ethylphenyl)isobutylamide Compound 32 | B | ND |
| 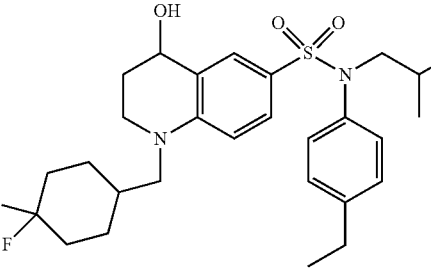 | 1-(4,4-difluorocyclohexylmethyl)-4-hydroxy-1,2,3,4-tetrahydroquinoline-6-sulfonic acid (4-ethylphenyl)isobutylamide Compound 33 | C | ND |
| 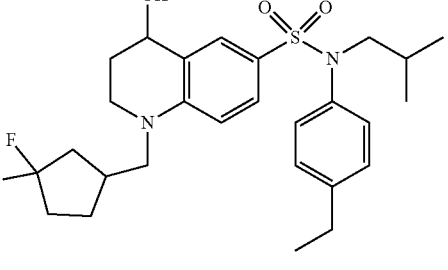 | 1-(3,3-difluorocyclopentylmethyl)-4-hydroxy-1,2,3,4-tetrahydroquinoline-6-sulfonic acid (4-ethylphenyl)isobutylamide Compound 34 | B | ND |

TABLE 1-continued

| | | IC50 hRORg | IC50 hCD4/IL17 |
|---|---|---|---|
| 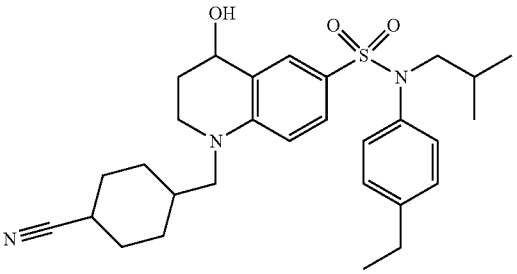 [SMILES: CCc1ccc(N(CC(C)C)S(=O)(=O)c2ccc3c(c2)C(O)CCN3CC2CCC(C#N)CC2)cc1] | 1-(4-cyanocyclohexylmethyl)-4-hydroxy-1,2,3,4-tetrahydroquinoline-6-sulfonic acid (4-ethylphenyl)isobutylamide Compound 35 | C | ND |
| 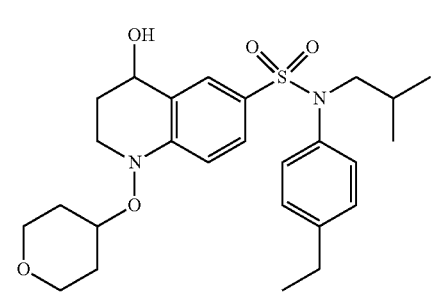 [SMILES: CCc1ccc(N(CC(C)C)S(=O)(=O)c2ccc3c(c2)C(O)CCN3OC2CCOCC2)cc1] | 4-hydroxy-1-(tetrahydropyran-4-yloxy)-1,2,3,4-tetrahydroquinoline-6-sulfonic acid (4-ethylphenyl)isobutylamide Compound 36 | B | ND |
| 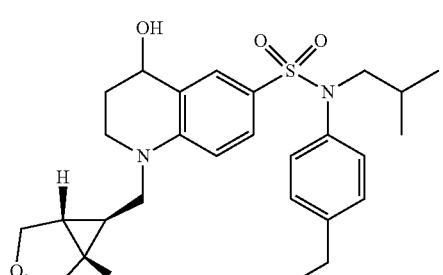 | 4-hydroxy-1-[(1S,5R,6S)-1-(3-oxabicyclo[3.1.0]hex-6-yl)methyl]-1,2,3,4-tetrahydroquinoline-6-sulfonic acid (4-ethylphenyl)isobutylamide Compound 37 | A | A |
| 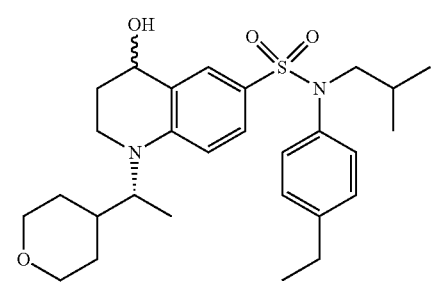 [SMILES: CCc1ccc(N(CC(C)C)S(=O)(=O)c2ccc3c(c2)C(O)CCN3[C@H](C)C2CCOCC2)cc1] | 4-hydroxy-1-[(R)-1-(tetrahydropyran-4-yl)ethyl]-1,2,3,4-tetrahydroquinoline-6-sulfonic acid (4-ethylphenyl)isobutylamide Compound 38 | C | ND |
| 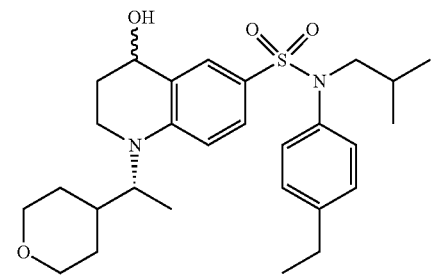 [SMILES: CCc1ccc(N(CC(C)C)S(=O)(=O)c2ccc3c(c2)C(O)CCN3[C@H](C)C2CCOCC2)cc1] | 4-hydroxy-1-[(R)-1-(tetrahydropyran-4-yl)ethyl]-1,2,3,4-tetrahydroquinoline-6-sulfonic acid (4-ethylphenyl)isobutylamide Compound 39 | C | ND |

TABLE 1-continued

| Structure | Name | IC50 hRORg | IC50 hCD4/IL17 |
|---|---|---|---|
| | 4-hydroxy-1-[(S)-1-(tetrahydropyran-4-yl)ethyl]-1,2,3,4-tetrahydroquinoline-6-sulfonic acid (4-ethylphenyl)isobutylamide Compound 40 | B | ND |
| | 4-hydroxy-1-[(S)-1-(tetrahydropyran-4-yl)ethyl]-1,2,3,4-tetrahydroquinoline-6-sulfonic acid (4-ethylphenyl)isobutylamide Compound 41 | B | ND |
| | 4-hydroxy-1-(4-hydroxycyclohexylmethyl)-1,2,3,4-tetrahydroquinoline-6-sulfonic acid (4-ethylphenyl)isobutylamide Compound 42 | B | ND |
| | 4-hydroxy-1-(4-hydroxycyclohexylmethyl)-1,2,3,4-tetrahydroquinoline-6-sulfonic acid (4-ethylphenyl)isobutylamide Compound 43 | B | ND |
| | 4-hydroxy-1-(2-oxaspiro[3.3]hept-6-ylmethyl)-1,2,3,4-tetrahydroquinoline-6-sulfonic acid (4-ethylphenyl)isobutylamide Compound 44 | B | ND |

TABLE 1-continued

| | | IC50 hRORg | IC50 hCD4/IL17 |
|---|---|---|---|
| 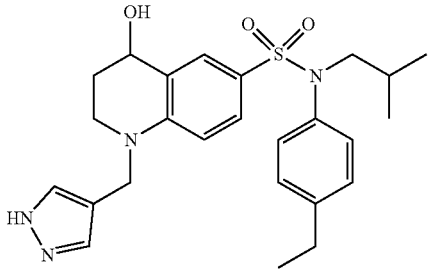 [SMILES: CCc1ccc(N(CC(C)C)S(=O)(=O)c2ccc3c(c2)C(O)CCN3Cc2cn[nH]c2)cc1] | 4-hydroxy-1-(1H-pyrazol-4-ylmethyl)-1,2,3,4-tetrahydroquinoline-6-sulfonic acid (4-ethylphenyl)isobutylamide<br>Compound 45 | B | A |
| 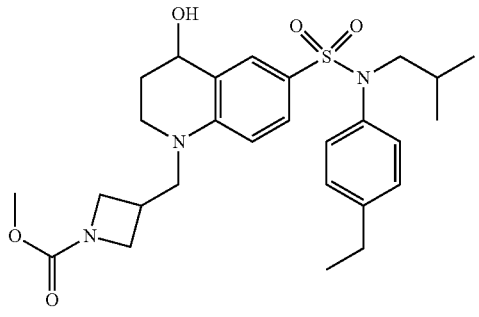 [SMILES: CCc1ccc(N(CC(C)C)S(=O)(=O)c2ccc3c(c2)C(O)CCN3CC2CN(C(=O)OC)C2)cc1] | methyl ester of 3-{6-[(4-ethylphenyl)isobutylsulfamoyl]-4-hydroxy-3,4-dihydro-2H-quinolin-1-ylmethyl}azetidine-1-carboxylic acid<br>Compound 46 | B | B |
| 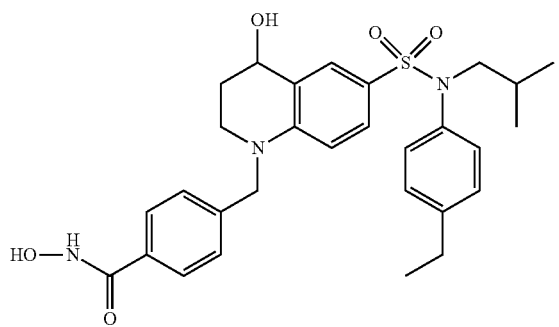 [SMILES: CCc1ccc(N(CC(C)C)S(=O)(=O)c2ccc3c(c2)C(O)CCN3Cc2ccc(C(=O)NO)cc2)cc1] | 4-{6-[(4-ethylphenyl)isobutylsulfamoyl]-4-hydroxy-3,4-dihydro-2H-quinolin-1-ylmethyl}-N-hydroxybenzamide<br>Compound 47 | C | ND |
| 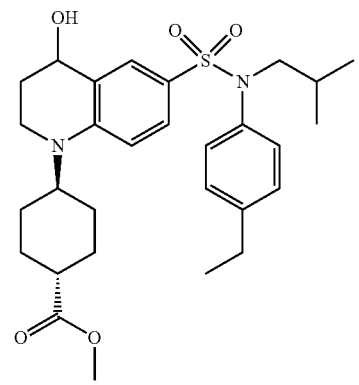 [SMILES: CCc1ccc(N(CC(C)C)S(=O)(=O)c2ccc3c(c2)C(O)CCN3[C@H]2CC[C@H](C(=O)OC)CC2)cc1] | methyl (1R,4R)-4-(6-(N-(4-ethylphenyl)-N-isobutylsulfamoyl)-4-hydroxy-3,4-dihydroquinolin-1(2H)-yl)cyclohexane-1-carboxylate<br>Compound 48 | C | ND |

TABLE 1-continued

| | | IC50 hRORg | IC50 hCD4/IL17 |
|---|---|---|---|
| 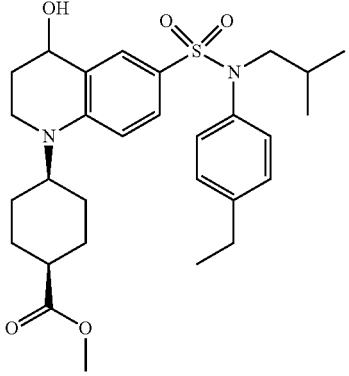 [SMILES: CCc1ccc(N(CC(C)C)S(=O)(=O)c2ccc3c(c2)C(O)CCN3[C@H]2CC[C@@H](C(=O)OC)CC2)cc1] | methyl (1S,4S)-4-(6-(N-(4-ethylphenyl)-N-isobutylsulfamoyl)-4-hydroxy-3,4-dihydroquinolin-1(2H)-yl)cyclohexane-1-carboxylate Compound 49 | C | ND |
| 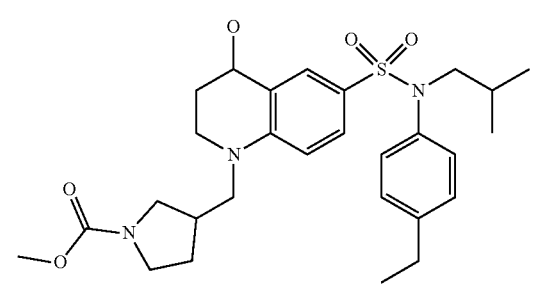 [SMILES: CCc1ccc(N(CC(C)C)S(=O)(=O)c2ccc3c(c2)C(O)CCN3CC2CCN(C(=O)OC)C2)cc1] | methyl ester of 3-{6-[(4-ethylphenyl)isobutylsulfamoyl]-4-hydroxy-3,4-dihydro-2H-quinolin-1-ylmethyl}pyrrolidine-1-carboxylic acid Compound 50 | C | ND |
| 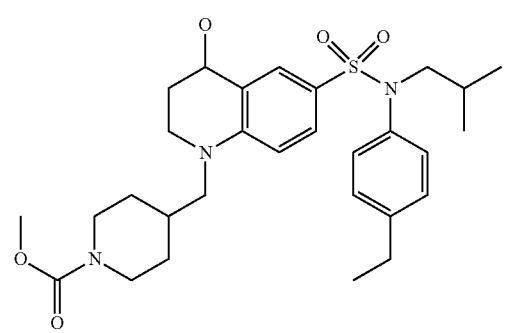 [SMILES: CCc1ccc(N(CC(C)C)S(=O)(=O)c2ccc3c(c2)C(O)CCN3CC2CCN(C(=O)OC)CC2)cc1] | methyl ester of 4-{6-[(4-ethylphenyl)isobutylsulfamoyl]-4-hydroxy-3,4-dihydro-2H-quinolin-1-ylmethyl}piperidine-1-carboxylic acid Compound 51 | C | ND |
| 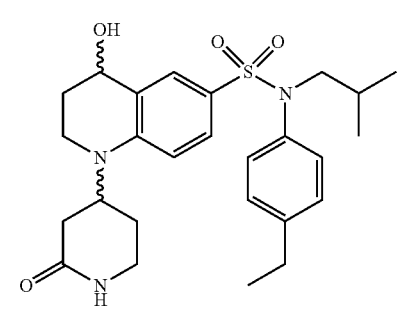 [SMILES: CCc1ccc(N(CC(C)C)S(=O)(=O)c2ccc3c(c2)C(O)CCN3C2CCNC(=O)C2)cc1] | Diastereoisomer 1 4-hydroxy-1-(2-oxopiperidin-4-yl)-1,2,3,4-tetrahydroquinoline-6-sulfonic acid (4-ethylphenyl)isobutylamide Compound 52 | C | ND |
| 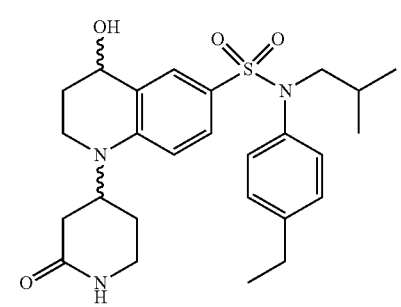 [SMILES: CCc1ccc(N(CC(C)C)S(=O)(=O)c2ccc3c(c2)C(O)CCN3C2CCNC(=O)C2)cc1] | Diastereoisomer 2 4-hydroxy-1-(2-oxopiperidin-4-yl)-1,2,3,4-tetrahydroquinoline-6-sulfonic acid (4-ethylphenyl)isobutylamide Compound 53 | C | ND |

TABLE 1-continued

| | | IC50 hRORg | IC50 hCD4/IL17 |
|---|---|---|---|
| 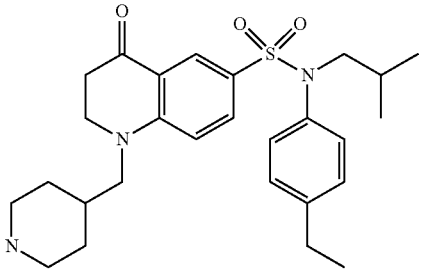 [SMILES: CCc1ccc(N(CC(C)C)S(=O)(=O)c2ccc3c(c2)C(=O)CCN3CC2CCNCC2)cc1] | 4-oxo-1-piperidin-4-ylmethyl-1,2,3,4-tetrahydroquinoline-6-sulfonic acid (4-ethylphenyl)isobutylamide Compound 54 | C | ND |
| 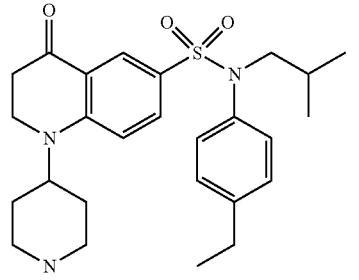 [SMILES: CCc1ccc(N(CC(C)C)S(=O)(=O)c2ccc3c(c2)C(=O)CCN3C2CCNCC2)cc1] | 4-oxo-1-piperidin-4-yl-1,2,3,4-tetrahydroquinoline-6-sulfonic acid (4-ethylphenyl)isobutylamide Compound 55 | C | ND |
| 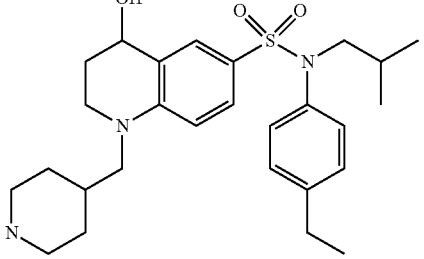 | 4-hydroxy-1-piperidin-4-ylmethyl-1,2,3,4-tetrahydroquinoline-6-sulfonic acid (4-ethylphenyl)isobutylamide Compound 56 | C | ND |
| 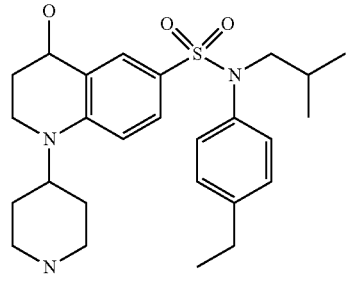 [SMILES: CCc1ccc(N(CC(C)C)S(=O)(=O)c2ccc3c(c2)C(O)CCN3C2CCNCC2)cc1] | 4-hydroxy-1-piperidin-4-yl-1,2,3,4-tetrahydroquinoline-6-sulfonic acid (4-ethylphenyl)isobutylamide Compound 57 | C | ND |
| 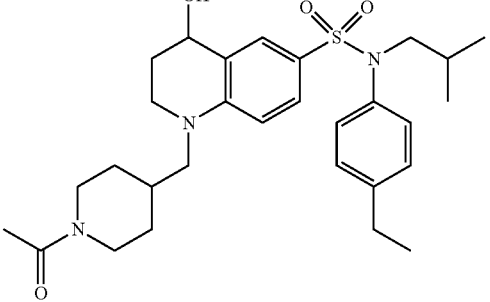 | 4-hydroxy-1-piperidin-4-ylmethyl-1,2,3,4-tetrahydroquinoline-6-sulfonic acid (4-ethylphenyl)isobutylamide Compound 58 | C | ND |

TABLE 1-continued

| | | IC50 hRORg | IC50 hCD4/IL17 |
|---|---|---|---|
| 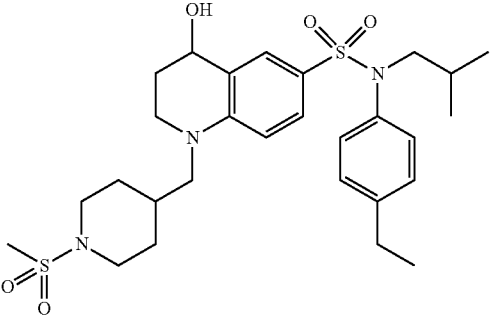 [SMILES: CCc1ccc(N(CC(C)C)S(=O)(=O)c2ccc3c(c2)C(O)CCN3CC2CCN(S(C)(=O)=O)CC2)cc1] | 4-hydroxy-1-piperidin-4-ylmethyl-1,2,3,4-tetrahydroquinoline-6-sulfonic acid (4-ethylphenyl)isobutylamide Compound 59 | C | ND |
| 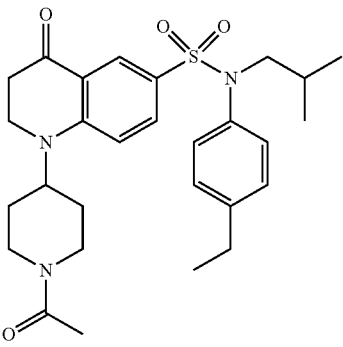 [SMILES: CCc1ccc(N(CC(C)C)S(=O)(=O)c2ccc3c(c2)C(=O)CCN3C2CCN(C(C)=O)CC2)cc1] | 1-(1-acetylpiperidin-4-yl)-4-oxo-1,2,3,4-tetrahydroquinoline-6-sulfonic acid (4-ethylphenyl)isobutylamide Compound 60 | C | ND |
| 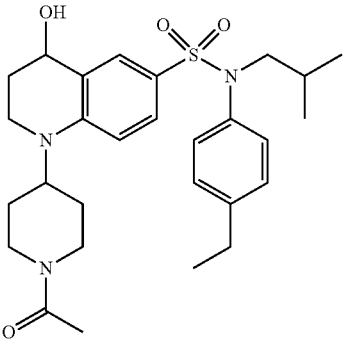 [SMILES: CCc1ccc(N(CC(C)C)S(=O)(=O)c2ccc3c(c2)C(O)CCN3C2CCN(C(C)=O)CC2)cc1] | 1-(1-acetylpiperidin-4-yl)-4-hydroxy-1,2,3,4-tetrahydroquinoline-6-sulfonic acid (4-ethylphenyl)isobutylamide Compound 61 | C | ND |
| 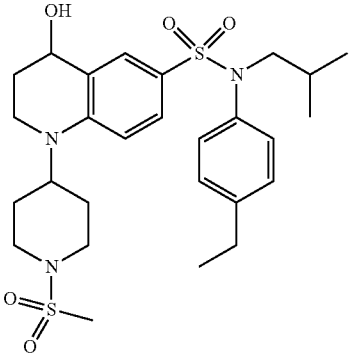 [SMILES: CCc1ccc(N(CC(C)C)S(=O)(=O)c2ccc3c(c2)C(O)CCN3C2CCN(S(C)(=O)=O)CC2)cc1] | 1-(1-acetylpiperidin-4-yl)-4-oxo-1,2,3,4-tetrahydroquinoline-6-sulfonic acid (4-ethylphenyl)isobutylamide Compound 63 | C | ND |

TABLE 1-continued

| | | IC50 hRORg | IC50 hCD4/IL17 |
|---|---|---|---|
| 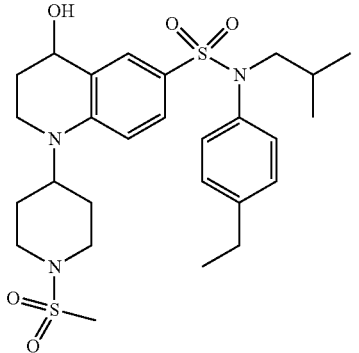 [SMILES: CCc1ccc(N(CC(C)C)S(=O)(=O)c2ccc3c(c2)C(O)CCN3C2CCN(S(C)(=O)=O)CC2)cc1] | 4-hydroxy-1-(1-methanesulfonylpiperidin-4-yl)-1,2,3,4-tetrahydroquinoline-6-sulfonic acid (4-ethylphenyl)isobutylamide Compound 64 | C | ND |
| 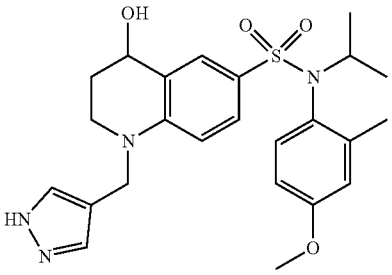 [SMILES: COc1ccc(N(C(C)C)S(=O)(=O)c2ccc3c(c2)C(O)CCN3Cc2cn[nH]c2)c(C)c1] | 4-hydroxy-1-(1H-pyrazol-4-ylmethyl)-1,2,3,4-tetrahydroquinoline-6-sulfonic acid isopropyl(4-methoxy-2-methylphenyl)amide Compound 65 | C | ND |
| 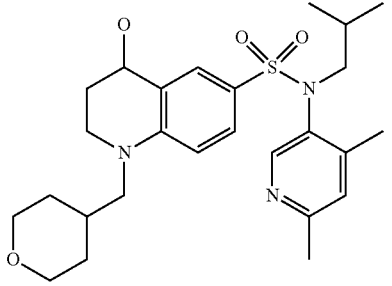 [SMILES: Cc1cc(C)c(N(CC(C)C)S(=O)(=O)c2ccc3c(c2)C(O)CCN3CC2CCOCC2)cn1] | 4-hydroxy-1-(tetrahydropyran-4-ylmethyl)-1,2,3,4-tetrahydroquinoline-6-sulfonic acid (4,6-dimethylpyridin-3-yl)isobutylamide Compound 66 | C | C |

ND: not determined;
A: IC50 < 100 nm;
B: IC50 = 100 nm-1 µM;
C: IC50 > 1 µM

In the tables described above, the median inhibitory concentrations $IC_{50}$ for the compounds belonging to formula (I) according to the invention have been given according to the following models:

GAL4—RORγ Transactivation

The RORγ transactivation model was developed from the line HG5LN, which is a HeLa line that stably expresses a luciferase reporter gene controlled by a pentamer of the GAL4 recognition domain of yeast and of a β-globin promoter. The HG5LN line was stably transfected by the DNA-binding domain (DBD) of GAL4 fused to the ROR gamma ligand-binding domain (LBD). Molecules that inhibit the ROR gamma constitutive activity reduce the luciferase expression, thus leading to a reduction in the emitted luminescence.

The cells are seeded in 384-well plates (5000 cells in 45 µL/well of culture medium containing 10% fetal calf serum) and incubated for 4 hours at 37° C., 5% $CO_2$. 5 µL of the test molecules (compounds described in the tables described above) are then added to each well and the plates are incubated for 18 hours at a temperature of 37° C. under 5% of $CO_2$. 20 µL of luciferase substrate (Promega) are added to each well and the luminescence emitted is read by a microplate reader.

The luminescence units ("RLU") are normalized by positive controls ("POS" containing a saturated concentration of N-(2,2,2-trifluoroethyl)-N-[4-[2,2,2-trifluoro-1-hydroxy-1-(trifluoromethyl)ethyl]phenyl])benzenesulfonamide and negative controls ("NEG" containing DMSO): % inhibition=((RLU-NEG)*100)/(POS-NEG). The IC50 values are calculated from a 4-parameter logistic model using the XLFit software (IDBS).

IL-17A Secretion

This model allows measurement of the effect of inhibitors on IL-17A secretion by CD4+ cells. The cells are frozen CD4+ cells (STEMCELL, #70026), isolated from peripheral human blood and activated with anti-CD3 and anti-CD28 antibodies. The amount of IL-17A secreted is measured by the TR-FRET (kit HTRF® Human Interleukin 17A (Cisbio, #64H17PEC)) technology.

The cells are rapidly thawed, resuspended in their culture medium (RPMI inactivated 10% FCS) supplemented with soluble anti-CD28 antibodies and seeded (100 000 cells/well) in 96-well plates precoated with anti-CD3 antibodies. The cells are then treated with the ranges of inhibitors to be tested (from 1000 nM to 0.05 nM, 0.1% DMSO). After 4 days of incubation, the HTRF signal is measured using a microplate reader (λexcitation=337 nm, λemission=620/665 nm). The ratios obtained (665/620) are normalized relative to the positive control (cells activated with anti-CD3 and anti-CD28, 0.1% DMSO). The $IC_{50}$ values are calculated from a 4-parameter logistic model using the XLFit software (IDBS).

Preferentially, the compounds of formula (I) according to the invention are chosen from the following compounds:

TABLE 3

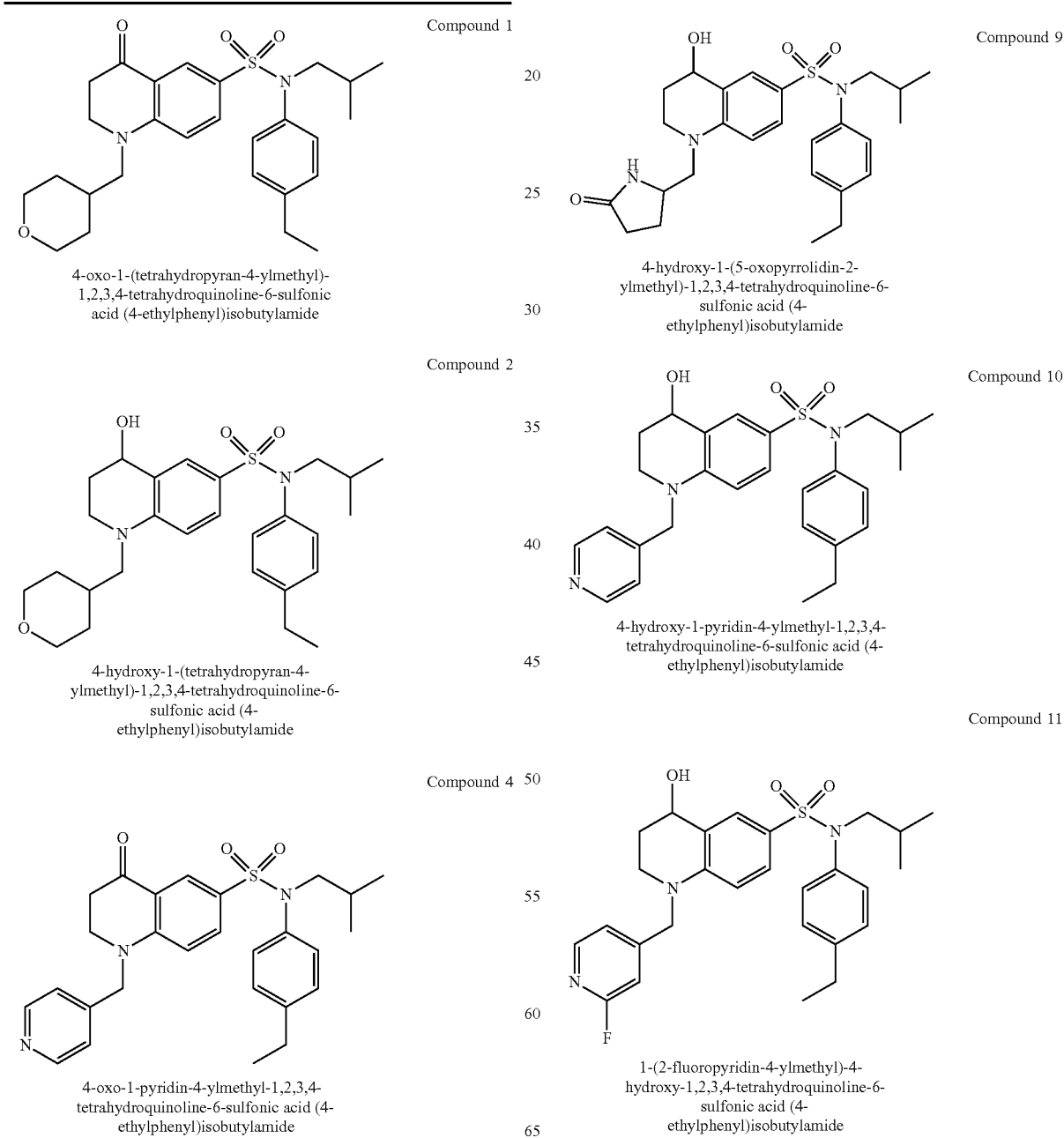

TABLE 3-continued

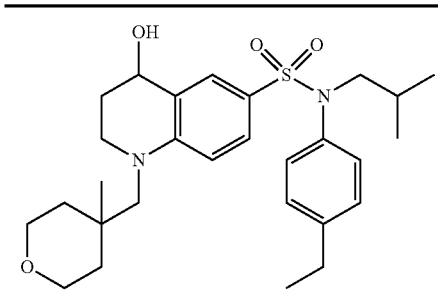

Compound 14

1-(4-methyltetrahydropyran-4-ylmethyl)-
4-hydroxy-1,2,3,4-tetrahydroquinoline-6-
sulfonic acid (4-
ethylphenyl)isobutylamide

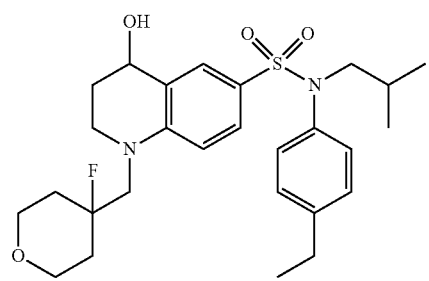

Compound 15

1-(4-fluorotetrahydropyran-4-ylmethyl)-
4-hydroxy-1,2,3,4-tetrahydroquinoline-6-
sulfonic acid (4-
ethylphenyl)isobutylamide

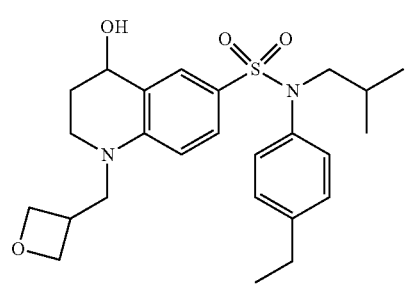

Compound 18

4-hydroxy-1-oxetan-3-ylmethyl-1,2,3,4-
tetrahydroquinoline-6-sulfonic acid (4-
ethylphenyl)isobutylamide

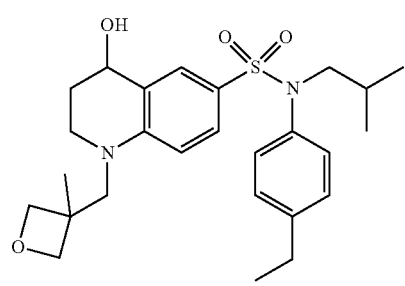

Compound 19

4-hydroxy-1-(3-methyloxetan-3-
ylmethyl)-1,2,3,4-tetrahydroquinoline-6-
sulfonic acid (4-
ethylphenyl)isobutylamide TABLE 3-continued

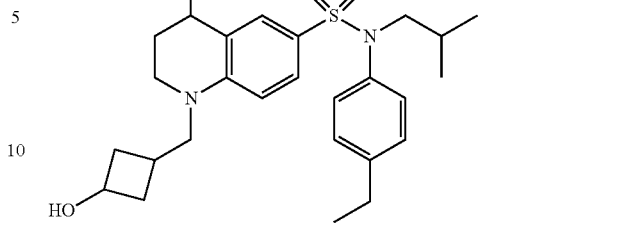

Compound 20

4-hydroxy-1-(3-
hydroxycyclobutylmethyl)-1,2,3,4-
tetrahydroquinoline-6-sulfonic acid (4-
ethylphenyl)isobutylamide
mixture of diastereoisomers:

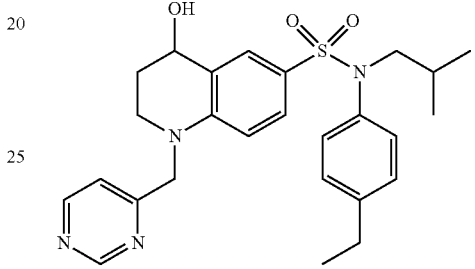

Compound 21

4-hydroxy-1-oxetan-3-ylmethyl-1,2,3,4-
tetrahydroquinoline-6-sulfonic acid (4-
ethylphenyl)isobutylamide

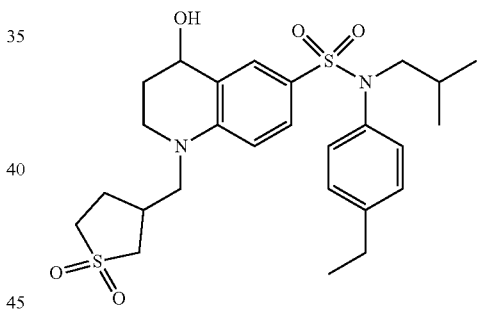

Compound 22

1-(1,1-dioxotetrahydro-1$\lambda^6$-thiophen-3-
ylmethyl)-4-hydroxy-1,2,3,4-
tetrahydroquinoline-6-sulfonic acid (4-
ethylphenyl)isobutylamide

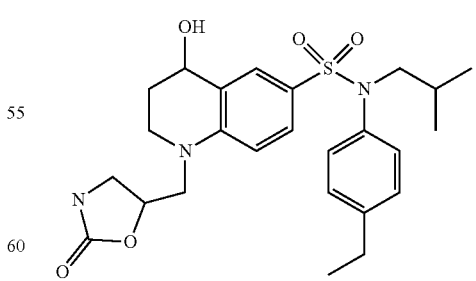

Compound 23

4-hydroxy-1-(2-oxooxazolidin-5-
ylmethyl)-1,2,3,4-tetrahydroquinoline-6-
sulfonic acid (4-
ethylphenyl)isobutylamide TABLE 3-continued

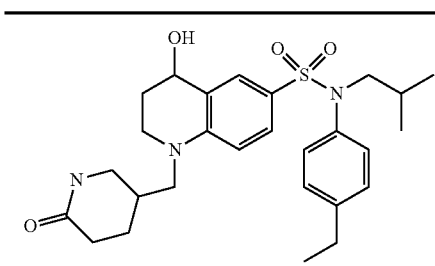

Compound 24

4-hydroxy-1-(6-oxopiperidin-3-
ylmethyl)-1,2,3,4-tetrahydroquinoline-6-
sulfonic acid (4-
ethylphenyl)isobutylamide

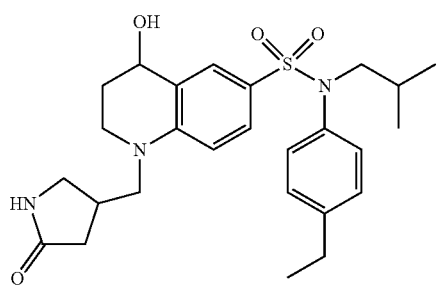

Compound 26

4-hydroxy-1-(5-oxopyrrolidin-3-
ylmethyl)-1,2,3,4-tetrahydroquinoline-6-
sulfonic acid (4-
ethylphenyl)isobutylamide

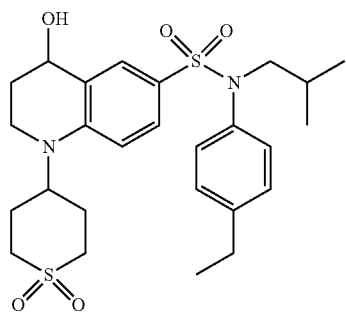

Compound 27

1-(1,1-dioxohexahydro-1$\lambda^6$-thiopyran-4-
yl)-4-hydroxy-1,2,3,4-
tetrahydroquinoline-6-sulfonic acid (4-
ethylphenyl)isobutylamide

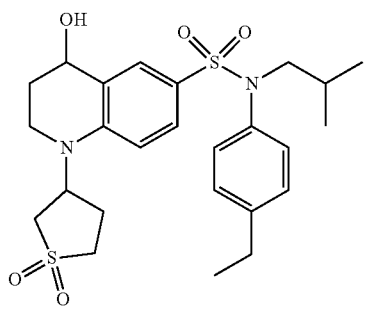

Compound 28

1-(1,1-dioxotetrahydro-1$\lambda^6$-thiophen-3-
yl)-4-hydroxy-1,2,3,4-
tetrahydroquinoline-6-sulfonic acid (4-
ethylphenyl)isobutylamide

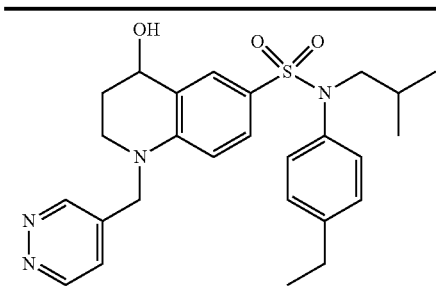

Compound 29

4-hydroxy-1-pyridazin-4-ylmethyl-
1,2,3,4-tetrahydroquinoline-6-sulfonic
acid (4 ethylphenyl)isobutylamide

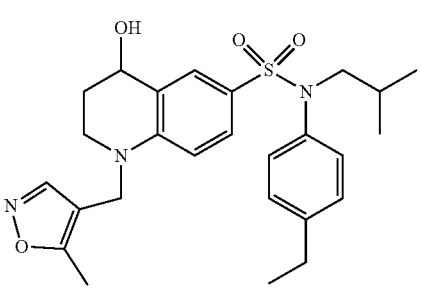

Compound 30

4-hydroxy-1-(5-methylisoxazol-4-
ylmethyl)-1,2,3,4-tetrahydroquinoline-6-
sulfonic acid (4-
ethylphenyl)isobutylamide

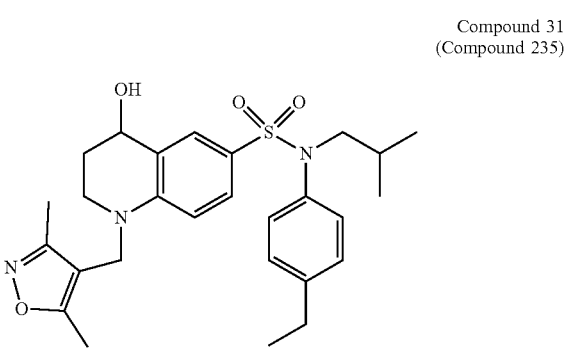

Compound 31
(Compound 235)

1-(3,5-dimethylisoxazol-4-ylmethyl)-4-
hydroxy-1,2,3,4-tetrahydroquinoline-6-
sulfonic acid (4-
ethylphenyl)isobutylamide

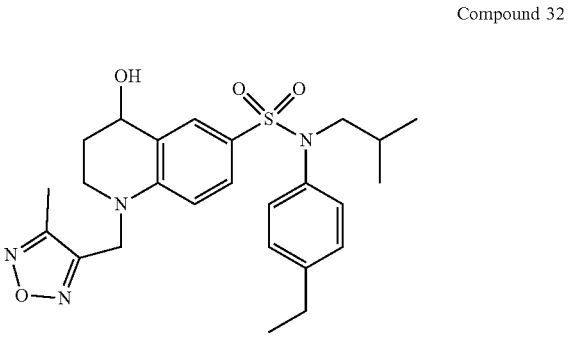

Compound 32

4-hydroxy-1-(4-methylfurazan-3-
ylmethyl)-1,2,3,4-tetrahydroquinoline-6-
sulfonic acid (4-
ethylphenyl)isobutylamide TABLE 3-continued

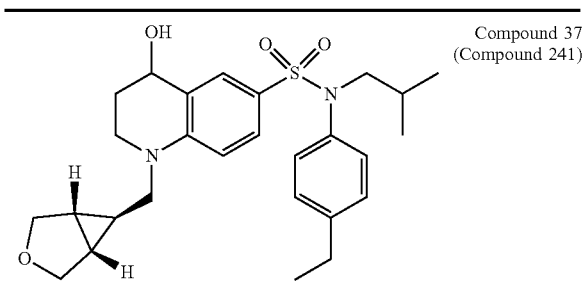

Compound 37
(Compound 241)

4-hydroxy-1-[(1S,5R,6S)-1-(3-oxabicyclo[3.1.0]hex-6-yl)methyl]-1,2,3,4-tetrahydroquinoline-6-sulfonic acid (4-ethylphenyl)isobutylamide

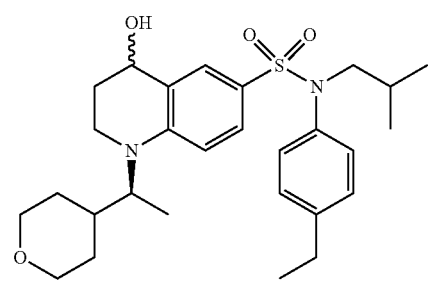

Compound 40

4-hydroxy-1-[(S)-1-(tetrahydropyran-4-yl)ethyl]-1,2,3,4-tetrahydroquinoline-6-sulfonic acid (4-ethylphenyl)isobutylamide

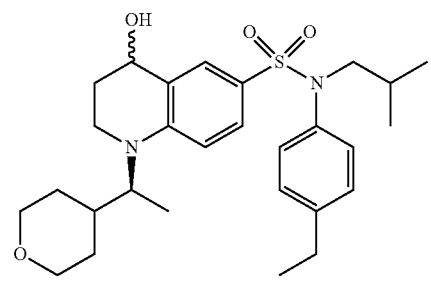

Compound 41

4-hydroxy-1-[(S)-1-(tetrahydropyran-4-yl)ethyl]-1,2,3,4-tetrahydroquinoline-6-sulfonic acid (4-ethylphenyl)isobutylamide

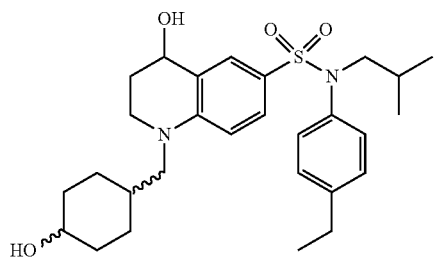

Compound 42

4-hydroxy-1-(4-hydroxycyclohexylmethyl)-1,2,3,4-tetrahydroquinoline-6-sulfonic acid (4-ethylphenyl)isobutylamide TABLE 3-continued

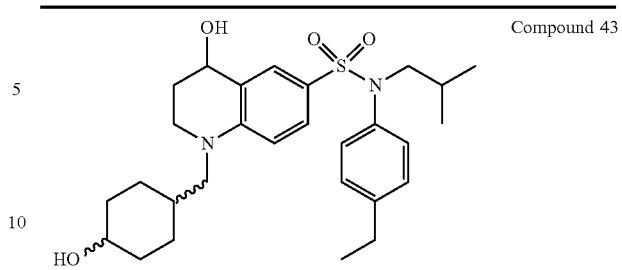

Compound 43

4-hydroxy-1-(4-hydroxycyclohexylmethyl)-1,2,3,4-tetrahydroquinoline-6-sulfonic acid (4-ethylphenyl)isobutylamide

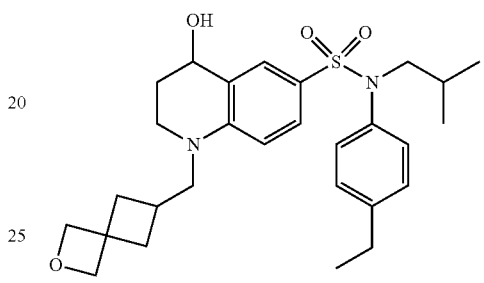

Compound 44

4-hydroxy-1-(2-oxaspiro[3.3]hept-6-ylmethyl)-1,2,3,4-tetrahydroquinoline-6-sulfonic acid (4-ethylphenyl)isobutylamide

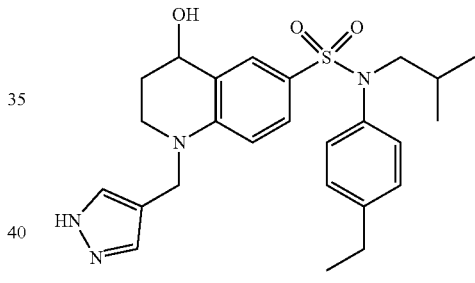

Compound 45

4-hydroxy-1-(1H-pyrazol-4-ylmethyl)-1,2,3,4-tetrahydroquinoline-6-sulfonic acid (4-ethylphenyl)isobutylamide Thus, compounds 1, 2, 4, 6, 9-11, 14, 15, 18 to 24, 26 to 32, 37, 40 and 45 are preferred.

The invention also relates to the compound(s) as described previously, as medicament and cosmetic.

Preferably, the invention also relates to the compound(s) as described previously, as medicament.

Specifically, the compounds according to the invention have advantageous pharmacological properties, given that said compounds modulate, i.e. inhibit, the activity of the RORγt receptor.

Thus, these properties make the compound(s) of formula (Ia) as described previously usable as medicament in the treatment of diseases mediated by the RORγt receptor.

Preferably, the compound(s) according to the invention are used in the treatment of inflammatory disorders and/or autoimmune diseases mediated by the RORγt receptor.

More preferentially, the compound(s) according to the invention, preferably those chosen from the compounds corresponding to formula (V), preferentially (V') and (V"), are used in the treatment of acne, psoriasis and/or atopic dermatitis.

According to another embodiment, the compounds according to the invention are used for cosmetic treatment of the skin.

As indicated above, the present invention also relates to a pharmaceutical composition comprising, in a pharmaceutically acceptable medium, one or more compounds of formula (I) as defined previously, pharmaceutically acceptable addition salts thereof, hydrates thereof and/or solvates thereof.

Preferably, the pharmaceutical composition comprises one or more compounds chosen from the compounds of formula (V) as defined previously, the pharmaceutically acceptable addition salts thereof, hydrates thereof and/or solvates thereof.

More preferentially, the pharmaceutical composition comprises one or more compounds of formula (I) chosen from compounds (1) to (66) defined previously.

The pharmaceutical composition according to the invention as described previously may be administered orally or topically.

Preferably, the pharmaceutical composition is conditioned in a form that is suitable for topical application.

Via the oral route, the composition may be in the form of tablets, gel capsules, coated tablets, syrups, suspensions, solutions, powders, granules, emulsions, suspensions of microspheres or nanospheres or lipid or polymeric vesicles allowing controlled release.

Via the topical route, the pharmaceutical composition according to the invention is more particularly intended for treating the skin and mucous membranes, and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or lipid or polymeric vesicles or of polymeric or gelled patches allowing controlled release.

The pharmaceutical composition is used for treating inflammatory disorders and/or autoimmune diseases mediated by the RORγt receptor.

More preferentially, the pharmaceutical composition is used in the treatment of acne and/or psoriasis.

The invention also relates to a process for treating diseases mediated by the RORγt receptor, comprising the administration, especially topically or orally, of a therapeutically effective amount of the pharmaceutical composition as defined above to a patient.

Preferably, the pharmaceutical composition is applied topically.

Preferentially, a subject of the invention is the compound(s) of formula (V) for their use in the treatment of acne.

As a variant, a subject of the invention is also the compound(s) of formula (V) for their use in the treatment of psoriasis.

Alternatively, the compound(s) of formula (V) according to the invention are used for cosmetic treatment of the skin.

The examples that follow serve to illustrate the invention without, however, being limiting in nature.

EXAMPLES

The standard LCMS method for analyzing the products is as follows: BEH $C_{18}$ standard column (150×2.1 mm, 1.8 μm) solvent: water/acetonitrile 0.1% formic acid.

The preparative HPLC purifications were performed on a $C_{18}$ column using, as eluent: 85% acetonitrile in water/0.1% formic acid.

Part I: Synthesis of the Bicyclic Sulfonamides Via Reaction Scheme 1

Reaction scheme 1
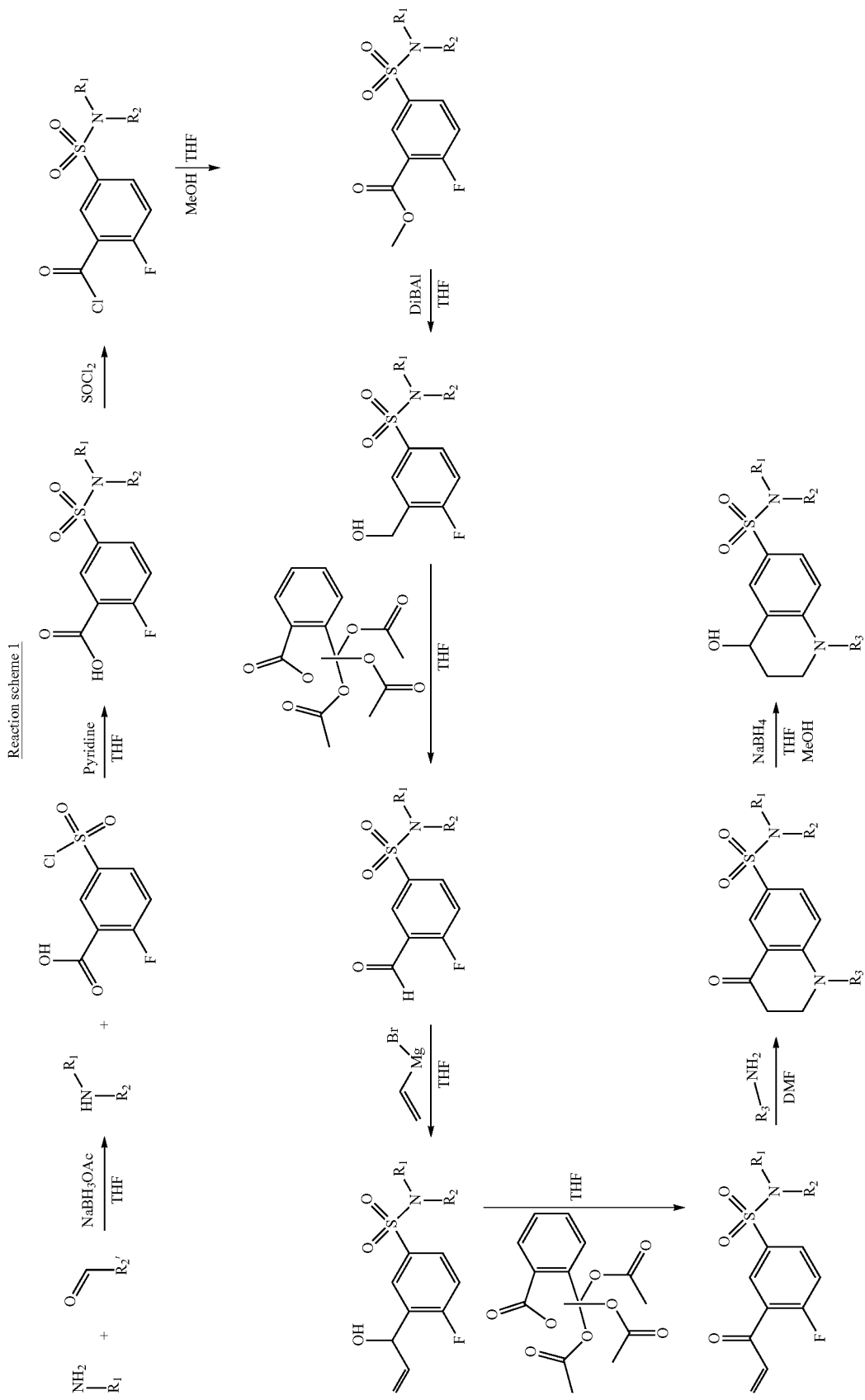

Example 1

4-Oxo-1-(tetrahydropyran-4-ylmethyl)-1,2,3,4-tetrahydroquinoline-6-sulfonic Acid (4-ethylphenyl)isobutylamide Compound 1

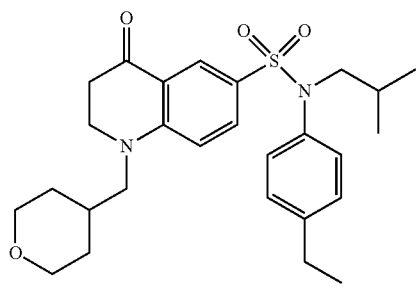

1. Synthesis of Intermediate 1.1

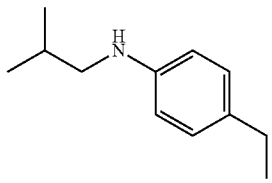

(4-ethylphenyl)isobutylamine

Isobutyraldehyde (6.33 ml; 0.07 mol) in tetrahydrofuran (100 ml) is added to 4-ethylaniline (9.48 ml; 0.08 mol). The mixture is stirred for 2 hours at room temperature.

Sodium triacetoxyborohydride (22.04 g; 0.10 mol) is then added. The mixture is stirred overnight at room temperature, water (100 ml) is added and the resulting mixture is extracted with ethyl acetate (2×100 ml). The organic phases are combined, washed with brine (100 ml), dried ($Na_2SO_4$) and concentrated.

The crude product is chromatographed on silica gel (eluent: heptane/dichloromethane from 0 to 50% of dichloromethane). The (4-ethylphenyl)isobutylamine is obtained in the form of an orange oil with a compliant $^1$H NMR.
MS: [M+H]=179

2. Synthesis of Intermediate 1.2

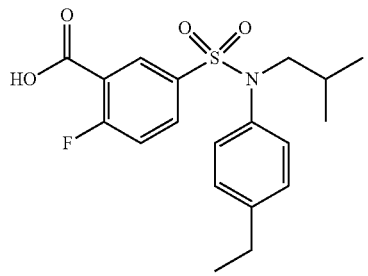 [SMILES: CCc1ccc(N(CC(C)C)S(=O)(=O)c2ccc(F)c(C(=O)O)c2)cc1]

5-[(4-ethylphenyl)isobutylsulfamoyl]-2-fluorobenzoic acid

A solution of (4-ethylphenyl)isobutylamine (0.80 g; 4.51 mmol) and pyridine (0.36 ml; 4.51 mmol) in tetrahydrofuran (8 ml) is added to a solution of 5-chlorosulfonyl-2-fluorobenzoic acid (1.44 g; 5.87 mmol) in tetrahydrofuran (8 ml).

The reaction medium is stirred for 19 hours at room temperature, hydrolyzed with aqueous 1N HCl solution and diluted with ethyl acetate.

The organic phase is washed with aqueous 1N HCl solution. The organic phase is dried ($Na_2SO_4$), filtered and concentrated.

The crude product is chromatographed on silica gel (eluent: dichloromethane/methanol, from 0 to 10% of methanol) and then by preparative HPLC (C18 column, eluent: from 60% to 70% of acetonitrile in water/0.1% of formic acid). The 5-[(4-ethylphenyl)isobutylsulfamoyl]-2-fluorobenzoic acid (0.56 g; 33%) is obtained in the form of an off-white solid with a compliant $^1$H NMR.
MS: [M−H]=378

3. Synthesis of Intermediate 1.3

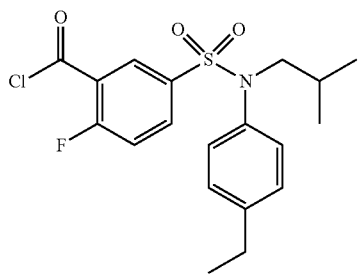 [SMILES: CCc1ccc(N(CC(C)C)S(=O)(=O)c2ccc(F)c(C(=O)Cl)c2)cc1]

5-[(4-ethylphenyl)isobutylsulfamoyl]-2-fluorobenzoyl chloride

A solution of 5-[(4-ethylphenyl)isobutylsulfamoyl]-2-fluorobenzoic acid (0.59 g; 1.55 mmol) in thionyl chloride (5.0 ml) is stirred for 3 hours at reflux and then concentrated to dryness. The 5-[(4-ethylphenyl)isobutylsulfamoyl]-2-fluorobenzoyl chloride (0.62 g; 100%) is obtained in the form of a brown oil.
MS: [M−H]=397

4. Synthesis of Intermediate 1.4

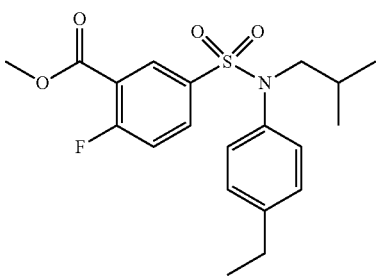 [SMILES: CCc1ccc(N(CC(C)C)S(=O)(=O)c2ccc(F)c(C(=O)OC)c2)cc1]

methyl 5-[(4-ethylphenyl)isobutylsulfamoyl]-2-fluorobenzoate

A mixture of 5-[(4-ethylphenyl)isobutylsulfamoyl]-2-fluorobenzoyl chloride (0.31 g; 0.78 mmol) and methanol (0.2 ml; 4.87 mmol) in tetrahydrofuran (3 ml) is stirred for 24 hours at room temperature.

The reaction medium is hydrolyzed with saturated aqueous NaHCO$_3$ solution and extracted with ethyl acetate. The organic phase is washed with brine, dried (Na$_2$SO$_4$), filtered and concentrated. The methyl 5-[(4-ethylphenyl)isobutylsulfamoyl]-2-fluorobenzoate (0.30 g; 98%) is obtained in the form of a white solid.

MS: [M−H]=394

5. Synthesis of Intermediate 1.5

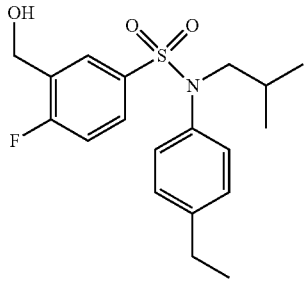

N-(4-ethylphenyl)-4-fluoro-3-hydroxymethyl-N-isobutylbenzenesulfonamide

A mixture, maintained at a temperature of −10° C., under argon, of methyl 5-[(4-ethylphenyl)isobutylsulfamoyl]-2-fluorobenzoate (2.78 g; 7.14 mmol) in dichloromethane (45 ml) and 1M diisobutylaluminum hydride solution (7.85 ml; 7.85 mmol) is stirred for 30 minutes. Further 1M diisobutylaluminum hydride solution (7.85 ml; 7.85 mmol) is added and stirring is continued for a further 1 hour.

The reaction medium is hydrolyzed with 1M sodium potassium tartrate solution, diluted with water and dichloromethane and stirred overnight at room temperature.

The organic phase is extracted, dried (Na$_2$SO$_4$), filtered and concentrated. The N-(4-ethylphenyl)-4-fluoro-3-hydroxymethyl-N-isobutylbenzenesulfonamide (2.65 g; 100%) is obtained in the form of a colorless oil with a compliant $^1$H NMR.

MS: [M−H]=366

6. Synthesis of Intermediate 1.6

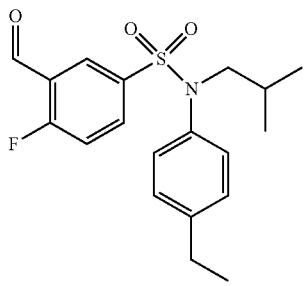 [SMILES: CCc1ccc(N(CC(C)C)S(=O)(=O)c2ccc(F)c(C=O)c2)cc1]

N-(4-ethylphenyl)-4-fluoro-3-formyl-N-isobutylbenzenesulfonamide

A mixture of N-(4-ethylphenyl)-4-fluoro-3-hydroxymethyl-N-isobutylbenzenesulfonamide (1.10 g; 3.01 mmol) in dichloromethane (20 ml) and Dess-Martin periodinane (1.56 g; 3.68 mmol) is stirred for 1 hour. The reaction medium is hydrolyzed with aqueous 10% Na$_2$S$_2$O$_3$ solution and diluted with dichloromethane.

Saturated aqueous sodium hydrogen carbonate solution (10 ml) is added and the reaction medium is stirred for two hours.

The organic phase is extracted, dried (Na$_2$SO$_4$), filtered and concentrated. The N-(4-ethylphenyl)-4-fluoro-3-formyl-N-isobutylbenzenesulfonamide (1.16 g; 106%) is obtained in the form of a pale yellow solid with a compliant $^1$H NMR.

MS: [M−H]=364

7. Synthesis of Intermediate 1.7

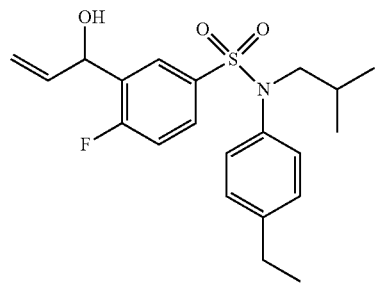 [SMILES: C=CC(O)c1cc(S(=O)(=O)N(CC(C)C)c2ccc(CC)cc2)ccc1F]

N-(4-ethylphenyl)-4-fluoro-3-(1-hydroxyallyl)-N-isobutylbenzenesulfonamide

A 1M solution of vinylmagnesium bromide in tetrahydrofuran (3.4 ml; 3.40 mmol) is added dropwise to a mixture of N-(4-ethylphenyl)-4-fluoro-3-formyl-N-isobutylbenzenesulfonamide (1.12 g; 3.08 mmol) in anhydrous tetrahydrofuran (20 ml) under argon at a temperature of −78° C.

The reaction medium is stirred for 50 minutes, hydrolyzed with aqueous 1M hydrochloric acid solution and extracted with ethyl acetate. The organic phase is washed with water, dried (Na$_2$SO$_4$), filtered and concentrated.

The crude product is chromatographed on silica gel (80 g, liquid/solid deposit, eluent: heptane/ethyl acetate, from 0 to 30% of ethyl acetate). The N-(4-ethylphenyl)-4-fluoro-3-(1-hydroxyallyl)-N-isobutylbenzenesulfonamide (0.93 g; 77%) is obtained in the form of a colorless oil with a compliant $^1$H NMR.

MS: [M−H]=392

8. Synthesis of Intermediate 1.8

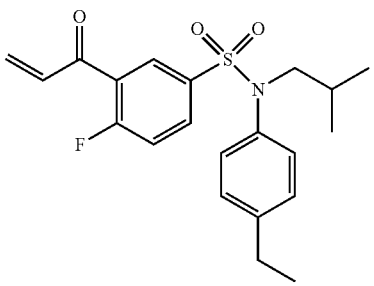 [SMILES: C=CC(=O)c1cc(S(=O)(=O)N(CC(C)C)c2ccc(CC)cc2)ccc1F]

3-acryloyl-N-(4-ethylphenyl)-4-fluoro-N-isobutyl-benzenesulfonamide

With a procedure similar to that described for the synthesis of intermediate 1.6 on N-(4-ethylphenyl)-4-fluoro-3-(1-hydroxyallyl)-N-isobutylbenzenesulfonamide (0.31 g; 0.79 mmol), 3-acryloyl-N-(4-ethylphenyl)-4-fluoro-N-isobutylbenzenesulfonamide (0.31 g; 100%) is obtained in the form of a white solid with a compliant $^1$H NMR.

MS: [M−H]=390

9. Synthesis of Compound 1 According to the Invention

4-Aminomethyltetrahydropyran (0.13 ml; 1.10 mmol) is added to a solution of 3-acryloyl-N-(4-ethylphenyl)-4-fluoro-N-isobutylbenzenesulfonamide (0.38 g; 0.73 mmol) in N,N-dimethylformamide (2 ml).

The reaction medium is stirred for 5 minutes and purified directly by preparative HPLC (C18 column, eluent: acetonitrile in water/0.1% of formic acid). The 4-oxo-1-(tetrahydropyran-4-ylmethyl)-1,2,3,4-tetrahydroquinoline-6-sulfonic acid (4-ethylphenyl)isobutylamide (0.16 g; 44%) is obtained in the form of a yellow solid.

$^1$H NMR (DMSO-d6) δ: 0.83 (d, J=6.6 Hz, 6H), 1.18 (t, J=7.6 Hz, 3H), 1.30 (ddd, J=24.2, 12.1, 7.7 Hz, 2H), 1.36-1.44 (m, 1H), 1.58-1.66 (m, 2H), 1.97 (ddd, J=11.4, 7.6, 3.7 Hz, 1H), 2.61 (q, J=7.6 Hz, 2H), 2.64-2.69 (m, 2H), 3.23 (d, J=7.3 Hz, 2H), 3.29 (dd, J=11.8, 2.0 Hz, 2H), 3.35 (d, J=7.3 Hz, 2H), 3.61-3.72 (m, 2H), 3.83-3.96 (m, 2H), 7.02 (t, J=9.1 Hz, 3H), 7.16-7.20 (m, 2H), 7.34 (dd, J=9.1, 2.5 Hz, 1H), 7.77 (d, J=2.4 Hz, 1H)

MS: [M−H]=485

Example 2

Synthesis of 4-hydroxy-1-(tetrahydropyran-4-ylmethyl)-1,2,3,4-tetrahydroquinoline-6-sulfonic Acid (4-ethylphenyl)isobutylamide Compound 2

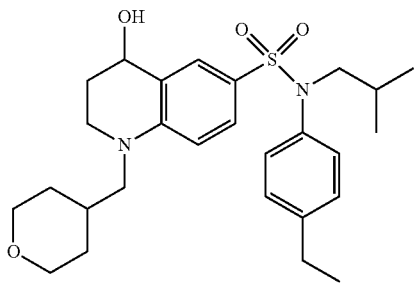

Sodium borohydride (22.00 mg; 0.58 mmol) and methanol (1 ml) are added to a solution of 4-oxo-1-(tetrahydropyran-4-ylmethyl)-1,2,3,4-tetrahydroquinoline-6-sulfonic acid (4-ethylphenyl)isobutylamide (0.14 g; 0.29 mmol) in tetrahydrofuran (1 ml) at a temperature of 0° C.

The reaction medium is stirred for 30 minutes, hydrolyzed with aqueous sodium dihydrogen phosphate solution (1M) and extracted with dichloromethane. The organic phase is concentrated. The crude product is purified by preparative HPLC (C18 column, eluent: acetonitrile in water/0.1% of formic acid).

The 4-hydroxy-1-(tetrahydropyran-4-ylmethyl)-1,2,3,4-tetrahydroquinoline-6-sulfonic acid (4-ethylphenyl)isobutylamide (100 mg; 71%) is obtained in the form of a yellow foam.

$^1$H NMR (DMSO-d6) δ: 0.82 (dd, J=6.7, 2.6 Hz, 6H), 1.17 (t, J=7.6 Hz, 3H), 1.26 (tt, J=12.1, 6.0 Hz, 2H), 1.39 (dt, J=13.7, 6.9 Hz, 1H), 1.51-1.59 (m, 2H), 1.75-1.85 (m, 2H), 1.94 (ddd, J=11.2, 7.5, 3.9 Hz, 1H), 2.59 (q, J=7.6 Hz, 3H), 3.12-3.27 (m, 6H), 3.31 (s, 6H), 3.39-3.49 (m, 1H), 3.84 (dd, J=11.1, 3.9 Hz, 2H), 4.49 (q, J=4.8 Hz, 1H), 5.29 (d, J=4.9 Hz, 1H), 6.65 (d, J=8.9 Hz, 1H), 6.94-7.02 (m, 2H), 7.08 (dd, J=8.9, 2.4 Hz, 1H), 7.12-7.19 (m, 2H), 7.30 (d, J=2.4 Hz, 1H)

MS: [M−H]=467

By chiral SFC chromatography of the racemic mixture, the following are obtained:

Enantiomer 1 of compound 2 with a retention time of 7.4 minutes $^1$H NMR (DMSO-d6) δ: 0.83 (dd, J=6.6, 2.6 Hz, 6H), 1.18 (t, J=7.6 Hz, 3H), 1.21-1.33 (m, 2H), 1.40 (hept, J=5.8 Hz, 1H), 1.56 (d, J=12.8 Hz, 2H), 1.78-1.86 (m, 2H), 1.89-2.03 (m, 1H), 2.60 (q, J=7.6 Hz, 2H), 3.18-3.38 (m, 7H), 3.41-3.50 (m, 1H), 3.77-3.91 (m, 2H), 4.51 (q, J=4.4 Hz, 1H), 5.31 (d, J=4.9 Hz, 1H), 6.66 (d, J=9.0 Hz, 1H), 6.99 (d, J=8.3 Hz, 2H), 7.09 (dd, J=8.9, 2.4 Hz, 1H), 7.17 (d, J=8.3 Hz, 2H), 7.31 (d, J=2.3 Hz, 1H)

MS: [M−H]=467

Enantiomer 2 of compound 2 with a retention time of 6.8 minutes $^1$H NMR (DMSO-d6) δ: 0.83 (dd, J=6.6, 2.6 Hz, 6H), 1.18 (t, J=7.6 Hz, 3H), 1.21-1.33 (m, 2H), 1.40 (hept, J=5.8 Hz, 1H), 1.56 (d, J=12.8 Hz, 2H), 1.78-1.86 (m, 2H), 1.89-2.03 (m, 1H), 2.60 (q, J=7.6 Hz, 2H), 3.18-3.38 (m, 7H), 3.41-3.50 (m, 1H), 3.77-3.91 (m, 2H), 4.51 (q, J=4.4 Hz, 1H), 5.31 (d, J=4.9 Hz, 1H), 6.66 (d, J=9.0 Hz, 1H), 6.99 (d, J=8.3 Hz, 2H), 7.09 (dd, J=8.9, 2.4 Hz, 1H), 7.17 (d, J=8.3 Hz, 2H), 7.31 (d, J=2.3 Hz, 1H)

MS: [M−H]=467

With a procedure similar to that described in example 1, the ketones of the table below are obtained:

| Example 3 | 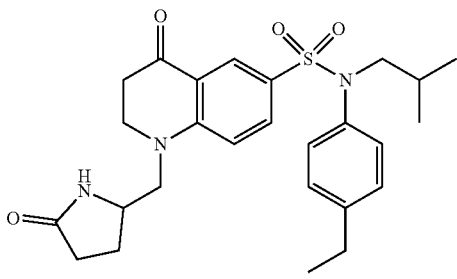 [SMILES: CCc1ccc(N(CC(C)C)S(=O)(=O)c2ccc3c(c2)C(=O)CCN3CC2CCC(=O)N2)cc1] Compound 3 | 4-oxo-1-(5-oxopyrrolidin-2-ylmethyl)-1,2,3,4-tetrahydroquinoline-6-sulfonic acid (4-ethylphenyl)isobutylamide<br>1H NMR (DMSO-d6) δ: 0.84 (d, J = 6.7 Hz, 6H), 1.18 (t, J = 7.6 Hz, 3H), 1.41 (hept, J = 6.6 Hz, 1H), 1.67-1.81 (m, 1H), 2.04-2.25 (m, 2H), 2.25-2.38 (m, 1H), 2.61 (q, J = 7.5 Hz, 2H), 2.66-2.83 (m, 2H), 3.23 (d, J = 7.3 Hz, 2H), 3.41-3.49 (m, 1H), 3.50-3.60 (m, 1H), 3.61-3.76 (m, 2H), 3.82-3.93 (m, 1H), 7.01 (d, J = 8.3 Hz, 2H), 7.05 (d, J = 9.2 Hz, 1H), 7.20 (d, J = 7.9 Hz, 2H), 7.33 (dd, J = 9.0, 2.6 Hz, 1H), 7.79 (d, J = 2.3 Hz, 1H), 7.83 (s, 1H).<br>MS: [M + H] = 484 |
|---|---|---|
| Example 4 | 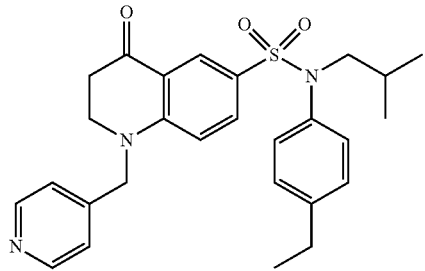 [SMILES: CCc1ccc(N(CC(C)C)S(=O)(=O)c2ccc3c(c2)C(=O)CCN3Cc2ccncc2)cc1] Compound 4 | 4-oxo-1-pyridin-4-ylmethyl-1,2,3,4-tetrahydroquinoline-6-sulfonic acid (4-ethylphenyl)isobutylamide<br>1H NMR (DMSO-d6) δ: 0.83 (d, J = 6.7 Hz, 6H), 1.17 (t, J = 7.6 Hz, 3H), 1.40 (hept, J = 7.0 Hz, 1H), 2.59 (q, J = 7.6 Hz, 2H), 2.80 (t, J = 7.2 Hz, 2H), 3.23 (d, J = 7.2 Hz, 2H), 3.79 (t, J = 7.0 Hz, 2H), 4.81 (s, 2H), 6.80 (d, J = 9.0 Hz, 1H), 6.98 (d, J = 8.3 Hz, 2H), 7.17 (d, J = 8.2 Hz, 2H), 7.30-7.36 (m, 3H), 7.82 (d, J = 2.9 Hz, 1H), 8.55 (d, J = 5.7 Hz, 2H).<br>MS: [M + H] = 478 |
| Example 5 | 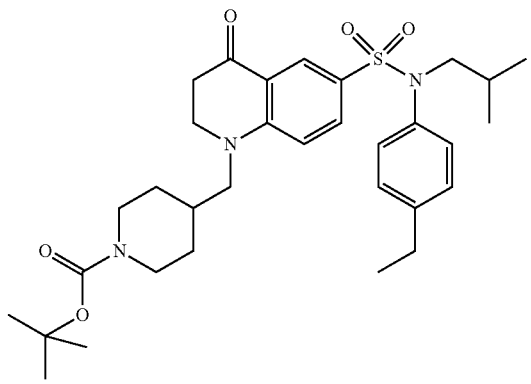 [SMILES: CCc1ccc(N(CC(C)C)S(=O)(=O)c2ccc3c(c2)C(=O)CCN3CC2CCN(C(=O)OC(C)(C)C)CC2)cc1] Compound 5 | tert-butyl 4-{6-[(4-ethylphenyl)isobutylsulfamoyl]-4-oxo-3,4-dihydro-2H-quinolin-1-ylmethyl}piperidine-1-carboxylate<br>1H NMR (DMSO-d6) δ: 0.83 (d, J = 6.7 Hz, 6H), 1.05-1.22 (m, 5H), 1.40 (s, 10H), 1.63-1.73 (m, 2H), 1.83-1.97 (m, 1H), 2.55-2.76 (m, 6H), 3.23 (d, J = 7.2 Hz, 2H), 3.33 (s, 2H), 3.65 (t, J = 7.1 Hz, 2H), 3.90-4.07 (m, 2H), 6.98-7.06 (m, 3H), 7.19 (d, J = 8.0 Hz, 2H), 7.33 (dd, J = 9.2, 2.5 Hz, 1H), 7.77 (d, J = 2.5 Hz, 1H).<br>MS: [M + H] = 584 |
| Example 6 | 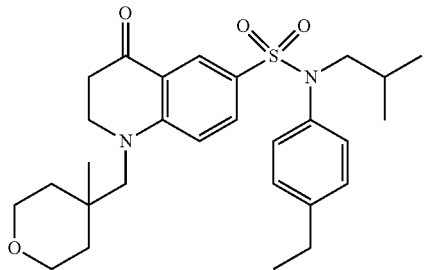 [SMILES: CCc1ccc(N(CC(C)C)S(=O)(=O)c2ccc3c(c2)C(=O)CCN3CC2(C)CCOCC2)cc1] Compound 6 | 1-(4-methyltetrahydropyran-4-ylmethyl)-4-oxo-1,2,3,4-tetrahydroquinoline-6-sulfonic acid (4-ethylphenyl)isobutylamide<br>1H NMR (DMSO-d6) δ: 0.83 (d, J = 6.7 Hz, 6H), 1.08 (s, 3H), 1.18 (t, J = 7.6 Hz, 3H), 1.30-1.47 (m, 3H), 1.56-1.68 (m, 2H), 2.60 (q, J = 7.6 Hz, 2H), 2.65-2.71 (m, 2H), 3.23 (d, J = 7.3 Hz, 2H), 3.30-3.37 (m, 2H), 3.53 (td, J = 11.3, 2.3 Hz, 2H), 3.58-3.73 (m, 4H), 7.00 (d, J = 8.3 Hz, 2H), 7.15-7.20 (m, 3H), 7.31 (dd, J = 9.1, 2.4 Hz, 1H), 7.82 (d, J = 2.4 Hz, 1H).<br>MS: [M + H] = 499 |
| Example 7 | 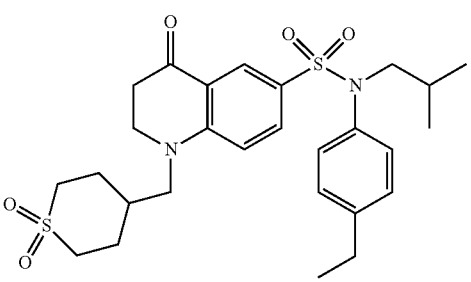 [SMILES: CCc1ccc(N(CC(C)C)S(=O)(=O)c2ccc3c(c2)C(=O)CCN3CC2CCS(=O)(=O)CC2)cc1] Compound 7 | 1-(1,1-dioxohexahydro-1$\lambda^6$-thiopyran-4-ylmethyl)-4-oxo-1,2,3,4-tetrahydroquinoline-6-sulfonic acid (4-ethylphenyl)isobutylamide<br>1H NMR (DMSO-d6) δ: 0.84 (d, J = 6.6 Hz, 6H), 1.18 (t, J = 7.5 Hz, 3H), 1.33-1.49 (m, 1H), 1.67-1.83 (m, 2H), 2.02-2.12 (m, 3H), 2.61 (q, J = 7.6 Hz, 2H), 2.68 (t, J = 7.1 Hz, 2H), 3.00-3.19 (m, 4H), 3.23 (d, J = 7.2 Hz, 2H), 3.41 (d, J = 6.8 Hz, 2H), 3.65 (t, J = 7.0 Hz, 2H), 7.01 (d, J = 7.9 Hz, 2H), 7.06 (d, J = 9.3 Hz, 1H), 7.19 (d, J = 7.9 Hz, 2H), 7.35 (dd, J = 8.9, 2.7 Hz, 1H), 7.78 (d, J = 2.8 |

| Example | Compound | Name / Data |
|---|---|---|
| | Compound 7 | Hz, 1H).<br>MS: [M + H] = 533 |
| Example 8 | 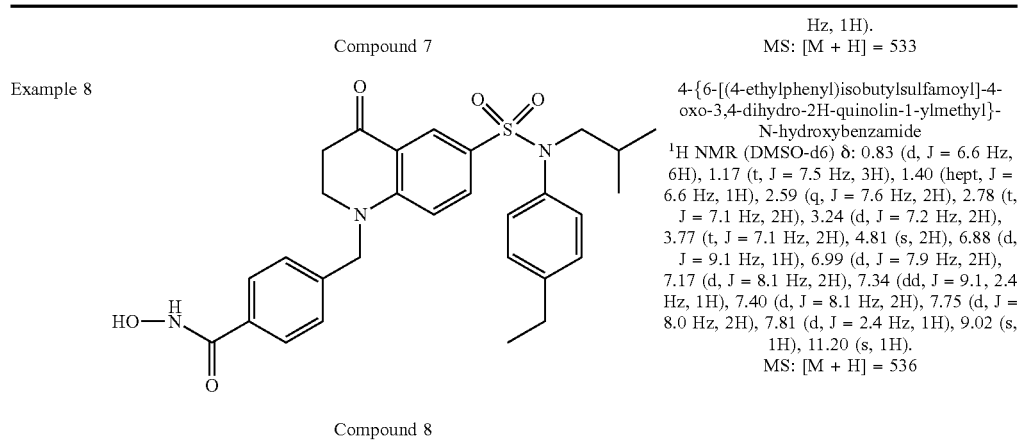<br>Compound 8 | 4-{6-[(4-ethylphenyl)isobutylsulfamoyl]-4-oxo-3,4-dihydro-2H-quinolin-1-ylmethyl}-N-hydroxybenzamide<br>$^1$H NMR (DMSO-d6) δ: 0.83 (d, J = 6.6 Hz, 6H), 1.17 (t, J = 7.5 Hz, 3H), 1.40 (hept, J = 6.6 Hz, 1H), 2.59 (q, J = 7.6 Hz, 2H), 2.78 (t, J = 7.1 Hz, 2H), 3.24 (d, J = 7.2 Hz, 2H), 3.77 (t, J = 7.1 Hz, 2H), 4.81 (s, 2H), 6.88 (d, J = 9.1 Hz, 1H), 6.99 (d, J = 7.9 Hz, 2H), 7.17 (d, J = 8.1 Hz, 2H), 7.34 (dd, J = 9.1, 2.4 Hz, 1H), 7.40 (d, J = 8.1 Hz, 2H), 7.75 (d, J = 8.0 Hz, 2H), 7.81 (d, J = 2.4 Hz, 1H), 9.02 (s, 1H), 11.20 (s, 1H).<br>MS: [M + H] = 536 |

With a procedure similar to that described in example 2 or by performing in sequence the cyclization (example 1) and the reduction (example 2) without isolating the ketone, the alcohols in the table below are obtained:

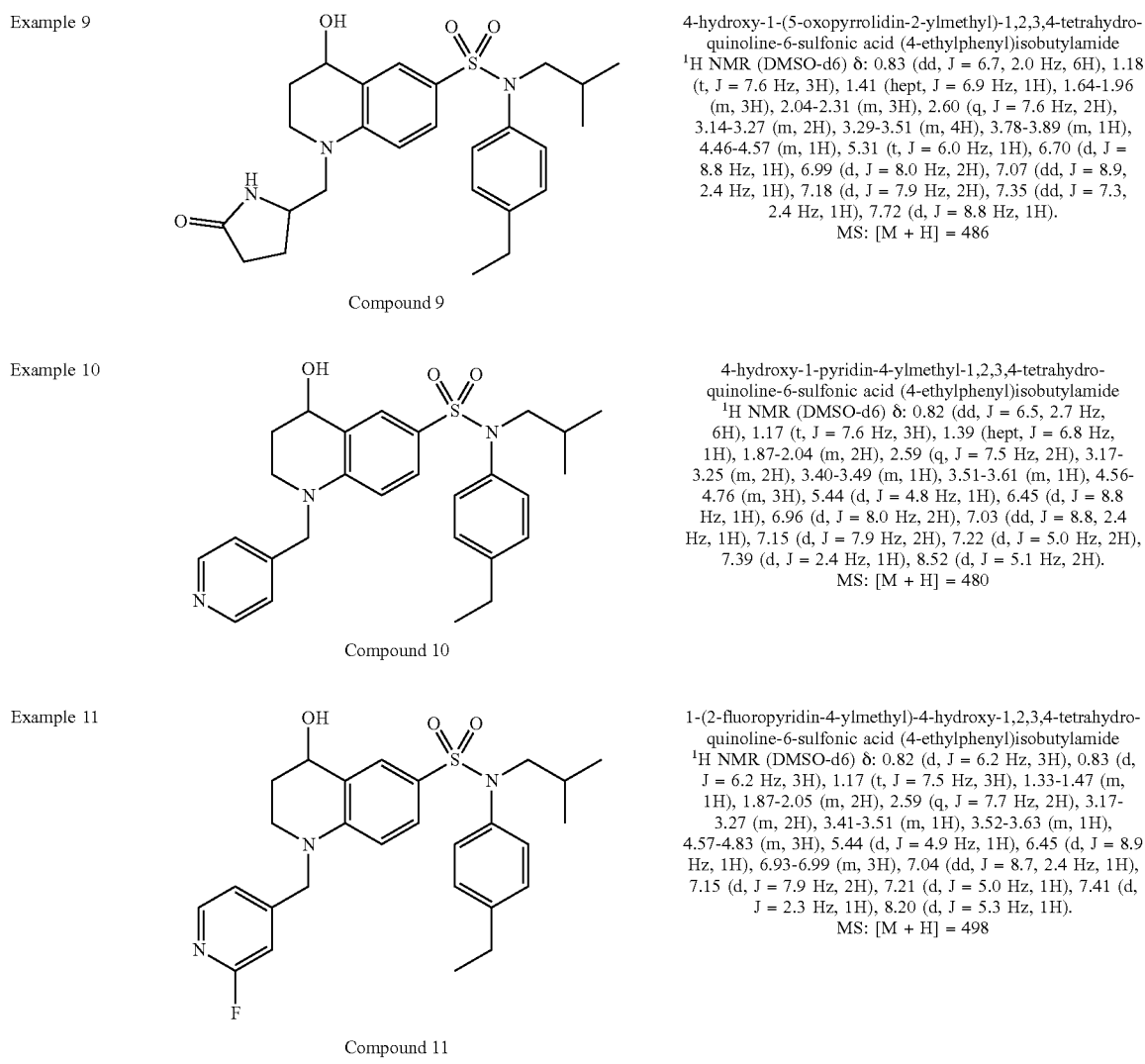

| Example | Compound | Name / Data |
|---|---|---|
| Example 9 | Compound 9 | 4-hydroxy-1-(5-oxopyrrolidin-2-ylmethyl)-1,2,3,4-tetrahydro-quinoline-6-sulfonic acid (4-ethylphenyl)isobutylamide<br>$^1$H NMR (DMSO-d6) δ: 0.83 (dd, J = 6.7, 2.0 Hz, 6H), 1.18 (t, J = 7.6 Hz, 3H), 1.41 (hept, J = 6.9 Hz, 1H), 1.64-1.96 (m, 3H), 2.04-2.31 (m, 3H), 2.60 (q, J = 7.6 Hz, 2H), 3.14-3.27 (m, 2H), 3.29-3.51 (m, 4H), 3.78-3.89 (m, 1H), 4.46-4.57 (m, 1H), 5.31 (t, J = 6.0 Hz, 1H), 6.70 (d, J = 8.8 Hz, 1H), 6.99 (d, J = 8.0 Hz, 2H), 7.07 (dd, J = 8.9, 2.4 Hz, 1H), 7.18 (d, J = 7.9 Hz, 2H), 7.35 (dd, J = 7.3, 2.4 Hz, 1H), 7.72 (d, J = 8.8 Hz, 1H).<br>MS: [M + H] = 486 |
| Example 10 | Compound 10 | 4-hydroxy-1-pyridin-4-ylmethyl-1,2,3,4-tetrahydro-quinoline-6-sulfonic acid (4-ethylphenyl)isobutylamide<br>$^1$H NMR (DMSO-d6) δ: 0.82 (dd, J = 6.5, 2.7 Hz, 6H), 1.17 (t, J = 7.6 Hz, 3H), 1.39 (hept, J = 6.8 Hz, 1H), 1.87-2.04 (m, 2H), 2.59 (q, J = 7.5 Hz, 2H), 3.17-3.25 (m, 2H), 3.40-3.49 (m, 1H), 3.51-3.61 (m, 1H), 4.56-4.76 (m, 3H), 5.44 (d, J = 4.8 Hz, 1H), 6.45 (d, J = 8.8 Hz, 1H), 6.96 (d, J = 8.0 Hz, 2H), 7.03 (dd, J = 8.8, 2.4 Hz, 1H), 7.15 (d, J = 7.9 Hz, 2H), 7.22 (d, J = 5.0 Hz, 2H), 7.39 (d, J = 2.4 Hz, 1H), 8.52 (d, J = 5.1 Hz, 2H).<br>MS: [M + H] = 480 |
| Example 11 | Compound 11 | 1-(2-fluoropyridin-4-ylmethyl)-4-hydroxy-1,2,3,4-tetrahydro-quinoline-6-sulfonic acid (4-ethylphenyl)isobutylamide<br>$^1$H NMR (DMSO-d6) δ: 0.82 (d, J = 6.2 Hz, 3H), 0.83 (d, J = 6.2 Hz, 3H), 1.17 (t, J = 7.5 Hz, 3H), 1.33-1.47 (m, 1H), 1.87-2.05 (m, 2H), 2.59 (q, J = 7.7 Hz, 2H), 3.17-3.27 (m, 2H), 3.52-3.63 (m, 1H), 3.41-3.51 (m, 1H), 4.57-4.83 (m, 3H), 5.44 (d, J = 4.9 Hz, 1H), 6.45 (d, J = 8.9 Hz, 1H), 6.93-6.99 (m, 3H), 7.04 (dd, J = 8.7, 2.4 Hz, 1H), 7.15 (d, J = 7.9 Hz, 2H), 7.21 (d, J = 5.0 Hz, 1H), 7.41 (d, J = 2.3 Hz, 1H), 8.20 (d, J = 5.3 Hz, 1H).<br>MS: [M + H] = 498 |

| Example 12 | 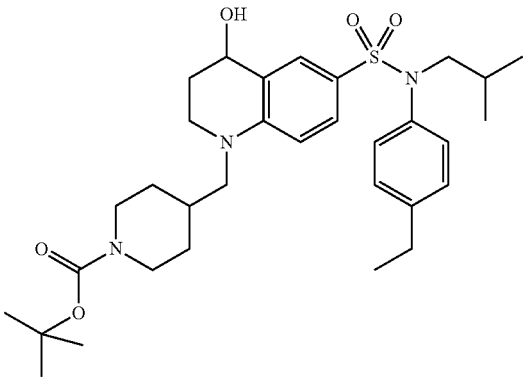<br>Compound 12 | 4-{6-[(4-ethylphenyl)isobutylsulfamoyl]-4-hydroxy-3,4-dihydro-2H-quinolin-1-ylmethyl}piperidine-1-carboxylic acid tert-butyl ester<br>¹H NMR (DMSO-d6) δ: 0.83 (dd, J = 6.6, 2.7 Hz, 6H), 1.02-1.15 (m, 2H), 1.18 (t, J = 7.6 Hz, 3H), 1.40 (s, 10H), 1.62 (d, J = 12.6 Hz, 2H), 1.72 -2.00 (m, 3H), 2.60 (q, J = 7.5 Hz, 2H), 3.15-3.27 (m, 4H), 3.27-3.36 (m, 3H), 3.38-3.49 (m, 1H), 3.90-4.03 (m, 2H), 4.46-4.54 (m, 1H), 5.32 (d, J = 4.9 Hz, 1H), 6.66 (d, J = 8.9 Hz, 1H), 6.99 (d, J = 8.0 Hz, 2H), 7.09 (dd, J = 8.9, 2.4 Hz, 1H), 7.17 (d, J = 7.9 Hz, 2H), 7.32 (d, J = 2.4 Hz, 1H).<br>MS: [M + H] = 586 |
|---|---|---|
| Example 13 | 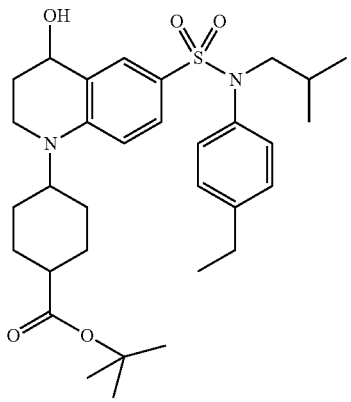<br>Compound 13 | 4-{6-[(4-ethylphenyl)isobutylsulfamoyl]-4-hydroxy-3,4-dihydro-2H-quinolin-1-yl}piperidine-1-carboxylic acid tert-butyl ester<br>¹H NMR (DMSO) δ: 0.83 (dd, J = 6.7, 1.9 Hz, 6H), 1.18 (t, J = 7.6 Hz, 3H), 1.42 (s, 10H), 1.54-1.70 (m, 4H), 1.70-1.86 (m, 2H), 2.60 (q, J = 7.6 Hz, 2H), 2.78-3.00 (m, 2H), 3.15-3.30 (m, 4H), 3.88-4.14 (m, 3H), 4.47 (q, J = 5.1 Hz, 1H), 5.33 (d, J = 5.0 Hz, 1H), 6.84 (d, J = 9.2 Hz, 1H), 6.98-7.02 (m, 2H), 7.10 (dd, J = 9.0, 2.5 Hz, 1H), 7.18 (d, J = 8.3 Hz, 2H), 7.36 (d, J = 2.5 Hz, 1H).<br>MS: [M + H] = 572 |
| Example 14 | 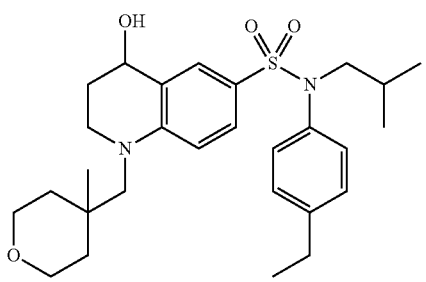<br>Compound 14 | 1-(4-methyltetrahydropyran-4-ylmethyl)-4-hydroxy-1,2,3,4-tetrahydroquinoline-6-sulfonic acid (4-ethylphenyl) isobutylamide<br>¹H NMR (DMSO-d6) δ: 0.83 (dd, J = 6.7, 2.7 Hz, 6H), 1.03 (s, 3H), 1.18 (t, J = 7.6 Hz, 3H), 1.29 (d, J = 13.1 Hz, 2H), 1.34-1.47 (m, 1H), 1.53-1.66 (m, 2H), 1.73-1.92 (m, 2H), 2.60 (q, J = 7.6 Hz, 2H), 3.15-3.28 (m, 4H), 3.27-3.38 (m, 1H), 3.40-3.56 (m, 3H), 3.58-3.71 (m, 2H), 4.53 (q, J = 5.0 Hz, 1H), 5.34 (d, J = 5.1 Hz, 1H), 6.81 (d J = 9.0 Hz, 1H), 6.95-7.00 (m, 2H), 7.05 (dd, J = 9.0, 2.5 Hz, 1H), 7.17 (d, J = 8.4 Hz, 2H), 7.35 (d, J = 2.4 Hz, 1H).<br>MS: [M + H] = 501 |
| Example 15 | 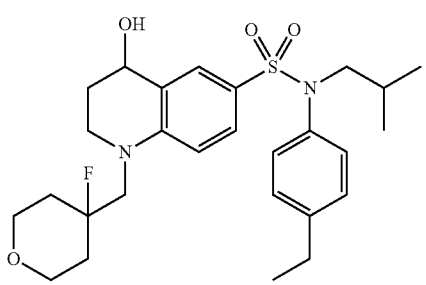<br>Compound 15 | 1-(4-fluorotetrahydropyran-4-ylmethyl)-4-hydroxy-1,2,3,4-tetrahydroquinoline-6-sulfonic acid (4-ethylphenyl) isobutylamide<br>¹H 1H NMR (DMSO-d6) δ: 0.83 (d, J = 6.6 Hz, 3H), 0.83 (d, J = 6.2 Hz, 3H), 1.18 (t, J = 7.6 Hz, 3H), 1.41 (hept, J = 6.8 Hz, 1H), 1.64-1.93 (m, 6H), 2.60 (q, J = 7.6 Hz, 2H), 3.15-3.28 (m, 2H), 3.34-3.44 (m, 1H), 3.45-3.56 (m, 3H), 3.61 (d, J = 23.1 Hz, 2H), 3.72-3.81 (m, 2H), 4.53 (q, J = 4.9 Hz, 1H), 5.34 (d, J = 4.8 Hz, 1H), 6.86 (d, J = 8.8 Hz, 1H), 6.99 (d, J = 8.1 Hz, 2H), 7.06 (dd, J = 9.1, 2.4 Hz, 1H), 7.17 (d, J = 7.8 Hz, 2H), 7.35 (d, J = 2.4 Hz, 1H).<br>MS: [M + H] = 505 |

| Example 16 | 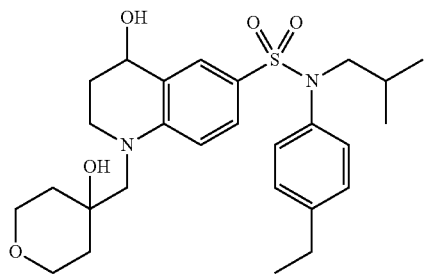<br>Compound 16 | 4-hydroxy-1-(4-hydroxytetrahydropyran-4-ylmethyl)-1,2,3,4-tetrahydroquinoline-6-sulfonic acid (4-ethylphenyl) isobutylamide<br>$^1$H 1H NMR (DMSO-d6) δ: 0.83 (d, J = 6.7 Hz, 3H), 0.83 (d, J = 6.3 Hz, 3H), 1.18 (t, J = 7.6 Hz, 3H), 1.34-1.49 (m, 3H), 1.56-1.70 (m, 2H), 1.75-1.92 (m, 2H), 2.60 (q, J = 7.7 Hz, 2H), 3.20 (dd, J = 7.5, 4.3 Hz, 4H), 3.39-3.57 (m, 2H), 3.56-3.67 (m, 4H), 4.52 (q, J = 4.8 Hz, 1H), 4.57 (s, 1H), 5.29 (d, J = 5.0 Hz, 1H), 6.89 (d, J = 9.1 Hz, 1H), 6.99 (d, J = 7.9 Hz, 2H), 7.04 (dd, J = 8.9, 2.5 Hz, 1H), 7.17 (d, J = 8.1 Hz, 2H), 7.33 (d, J = 2.5 Hz, 1H).<br>MS: [M + H] = 503 |
|---|---|---|
| Example 17 | 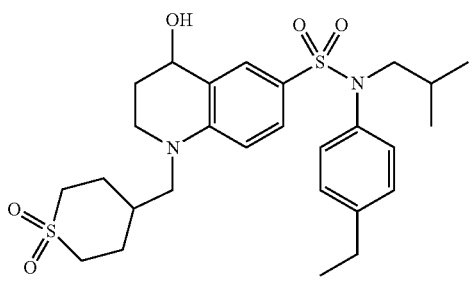<br>Compound 17 | 1-(1,1-dioxohexahydro-1□$^6$-thiopyran-4-ylmethyl)-4-hydroxy-1,2,3,4-tetrahydroquinoline-6-sulfonic acid (4-ethylphenyl)isobutylamide<br>$^1$H NMR (DMSO-d6) δ: 0.83 (dd, J = 6.6, 2.6 Hz, 6H), 1.19 (t, J = 7.6 Hz, 3H), 1.34-1.47 (m, 1H), 1.63-1.77 (m, 2H), 1.77-1.88 (m, 2H), 1.93-2.14 (m, 3H), 2.60 (q, J = 7.6 Hz, 2H), 2.96-3.26 (m, 6H), 3.26-3.34 (m, 3H), 3.36-3.49 (m, 1H), 4.51 (q, J = 4.8 Hz, 1H), 5.34 (d, J = 4.9 Hz, 1H), 6.70 (d, J = 9.0 Hz, 1H), 7.00 (d, J = 8.4 Hz, 2H), 7.09 (dd, J = 8.8, 2.4 Hz, 1H), 7.18 (d, J = 8.3 Hz, 2H), 7.32 (d, J = 2.4 Hz, 1H).<br>MS: [M + H] = 535 |
| Example 18 | 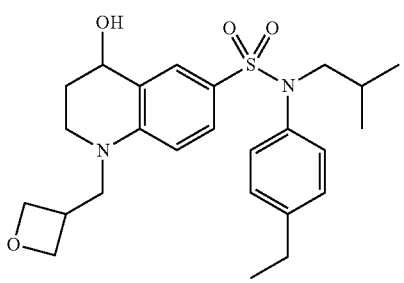<br>Compound 18 | 4-hydroxy-1-oxetan-3-ylmethyl-1,2,3,4-tetrahydroquinoline-6-sulfonic acid (4-ethylphenyl)isobutylamide<br>$^1$H NMR (DMSO-d6) δ: 0.83 (dd, J = 6.9, 2.4 Hz, 6H), 1.18 (t, J = 7.6 Hz, 3H), 1.32-1.48 (m, 1H), 1.76-1.86 (m, 2H), 2.60 (q, J = 7.6 Hz, 2H), 3.16-3.27 (m, 2H), 3.26-3.44 (m, 3H), 3.61-3.77 (m, 2H), 4.41 (q, J = 6.5 Hz, 2H), 4.45-4.53 (m, 1H), 4.61-4.68 (m, 2H), 5.32 (d, J = 5.1 Hz, 1H), 6.69 (d, J = 8.8 Hz, 1H), 6.99 (d, J = 8.2 Hz, 2H), 7.08 (dd, J = 8.9, 2.6 Hz, 1H), 7.18 (d, J = 7.9 Hz, 2H), 7.33 (d, J = 2.4 Hz, 1H).<br>MS: [M + H] = 459 |
| Example 19 | 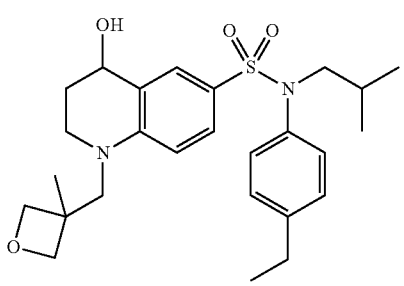<br>Compound 19 | 4-hydroxy-1-(3-methyloxetan-3-ylmethyl)-1,2,3,4-tetrahydroquinoline-6-sulfonic acid (4-ethylphenyl) isobutylamide<br>$^1$H NMR (DMSO-d6) δ: 0.82 (d, J = 6.7 Hz, 3H), 0.83 (d, J = 6.3 Hz, 3H), 1.18 (t, J = 7.6 Hz, 3H), 1.28 (s, 3H), 1.40 (hept, J = 6.8 Hz, 1H), 1.77-1.92 (m, 2H), 2.60 (q, J = 7.6 Hz, 2H), 3.17-3.40 (m, 4H), 3.50-3.61 (m, 2H), 4.13-4.23 (m, 2H), 4.49-4.57 (m, 3H), 5.35 (d, J = 4.8 Hz, 1H), 6.67 (d, J = 9.0 Hz, 1H), 6.97 (d, J = 8.0 Hz, 2H), 7.04 (dd, J = 8.9, 2.4 Hz, 1H), 7.16 (d, J = 7.9 Hz, 2H), 7.35 (d, J = 2.4 Hz, 1H).<br>MS: [M + H] = 473 |
| Example 20 | 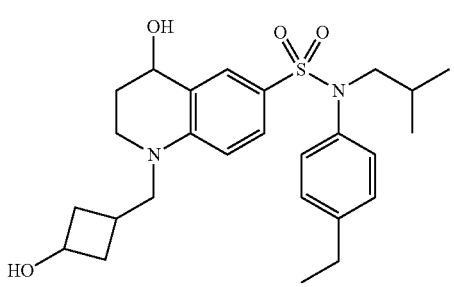<br>Compound 20 | 4-hydroxy-1-(3-hydroxycyclobutylmethyl)-1,2,3,4-tetrahydroquinoline-6-sulfonic acid (4-ethylphenyl) isobutylamide<br>mixture of diastereoisomers: $^1$H NMR (DMSO-d6) δ: 0.83 (d, J = 6.2 Hz, 6H), 0.83 (d, J = 6.8 Hz, 6H), 1.18 (t, J = 7.6 Hz, 6H), 1.33-1.46 (m, 2H), 1.52-1.65 (m, 2H), 1.75-1.86 (m, 4H), 1.87-2.07 (m, 4H), 2.23-2.32 (m, 2H), 2.60 (q, J = 7.6 Hz, 4H), 3.14-3.28 (m, 4H), 3.26-3.50 (m, 19H), 3.82-3.95 (m, 1H), 4.25-4.39 (m, 2H), 4.49 (q, J = 5.0 Hz, 2H), 4.99 (t, J = 5.8 Hz, 2H), 5.30 (d, J = 4.9 Hz, 2H), 6.60 (d, J = 9.1 Hz, 1H), 6.65 (d, J = 8.9 Hz, 1H), 6.99 (d, J = 7.9 Hz, 4H), 7.09 (dt, J = 8.9, 3.2 Hz, 2H), 7.17 (d, J = 8.1 Hz, 4H), 7.31 (s, 2H).<br>MS: [M + H] = 473 |

| Example 21 | 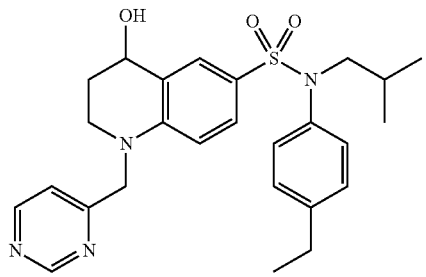<br>Compound 21 | 4-hydroxy-1-pyrimidin-4-ylmethyl-1,2,3,4-tetrahydro-quinoline-6-sulfonic acid (4-ethylphenyl) isobutylamide<br>$^1$H NMR (DMSO-d6) δ: 0.82 (dd, J = 6.5, 2.6 Hz, 6H), 1.17 (t, J = 7.5 Hz, 3H), 1.30-1.47 (m, 1H), 1.85-2.07 (m, 2H), 2.59 (q, J = 7.5 Hz, 2H), 3.15-3.27 (m, 2H), 3.45-3.57 (m, 1H), 3.55-3.68 (m, 1H), 4.57-4.80 (m, 3H), 5.44 (d, J = 4.9 Hz, 1H), 6.45 (d, J = 8.8 Hz, 1H), 6.96 (d, J = 8.1 Hz, 2H), 7.03 (dd, J = 8.8, 2.4 Hz, 1H), 7.15 (d, J = 8.1 Hz, 2H), 7.33 (d, J = 5.2 Hz, 1H), 7.40 (d, J = 2.4 Hz, 1H), 8.74 (d, J = 5.3 Hz, 1H), 9.16 (s, 1H).<br>MS: [M + H] = 481 |
|---|---|---|
| Example 22 | 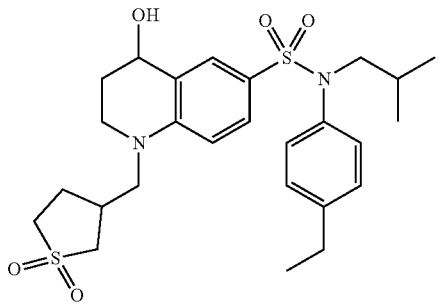<br>Compound 22 | 1-(1,1-dioxohexahydro-1□$^6$-thiophen-3-ylmethyl)-4-hydroxy-1,2,3,4-tetrahydroquinoline-6-sulfonic acid (4-ethylphenyl)isobutylamide<br>$^1$H NMR (DMSO-d6) δ: 0.79-0.87 (m, 6H), 1.18 (t, J = 7.6 Hz, 3H), 1.33-1.46 (m, 1H), 1.74-1.94 (m, 3H), 2.23-2.32 (m, 1H), 2.60 (q, J = 7.7 Hz, 2H), 2.70-2.82 (m, 1H), 2.91 (t, J = 11.8 Hz, 1H), 3.00-3.13 (m, 1H), 3.16-3.59 (m, 8H), 4.44-4.58 (m, 1H), 5.34 (d, J = 4.7 Hz, 1H), 6.76 (d, J = 8.8 Hz, 1H), 6.99 (d, J = 8.0 Hz, 2H), 7.04-7.11 (m, 1H), 7.18 (d, J = 7.9 Hz, 2H), 7.36 (s, 1H).<br>MS: [M + H] = 521 |
| Example 23 | 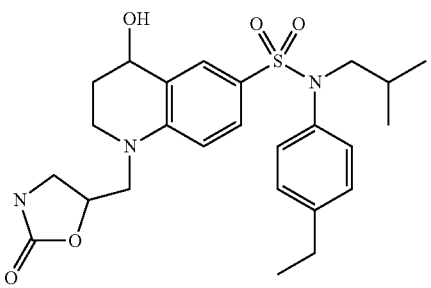<br>Compound 23 | 4-hydroxy-1-(2-oxooxazolidin-5-ylmethyl)-1,2,3,4-tetrahydroquinoline-6-sulfonic acid (4-ethylphenyl) isobutylamide<br>$^1$H NMR (DMSO-d6) δ: 0.79-0.88 (m, 6H), 1.18 (t, J = 7.5 Hz, 3H), 1.33-1.48 (m, 1H), 1.74-1.94 (m, 2H), 2.60 (q, J = 7.7 Hz, 2H), 3.08-3.29 (m, 3H), 3.29-3.74 (m, 5H), 4.46-4.59 (m, 1H), 4.74-4.87 (m, 1H), 5.37 (t, J = 5.5 Hz, 1H), 6.75 (dd, J = 8.9, 3.5 Hz, 1H), 6.99 (d, J = 7.8 Hz, 2H), 7.08 (dd, J = 8.8, 2.4 Hz, 1H), 7.18 (d, J = 7.9 Hz, 2H), 7.33-7.39 (m, 1H), 7.58 (s, 1H).<br>MS: [M + H] = 470 |
| Example 24 | 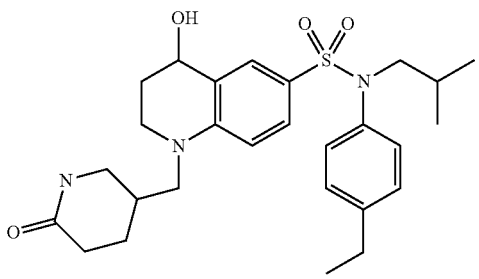<br>Compound 24 | 4-hydroxy-1-(6-oxopiperidin-3-ylmethyl)-1,2,3,4-tetrahydroquinoline-6-sulfonic acid (4-ethylphenyl) isobutylamide<br>$^1$H NMR (DMSO-d6) δ: 0.79-0.88 (m, 6H), 1.18 (t, J = 7.6 Hz, 3H), 1.33-1.58 (m, 2H), 1.74-1.90 (m, 3H), 2.08-2.26 (m, 3H), 2.60 (q, J = 7.5 Hz, 2H), 2.94 (t, J = 10.9 Hz, 1H), 3.11-3.25 (m, 3H), 3.25-3.49 (m, 4H), 4.52 (q, J = 4.8 Hz, 1H), 5.34 (d, J = 4.8 Hz, 1H), 6.70 (d, J = 8.9 Hz, 1H), 6.99 (d, J = 8.1 Hz, 2H), 7.09 (dd, J = 8.9, 2.4 Hz, 1H), 7.18 (d, J = 8.1 Hz, 2H), 7.33 (d, J = 2.4 Hz, 1H), 7.46 (d, J = 3.4 Hz, 1H).<br>MS: [M + H − 18] = 482 |
| Example 25 | 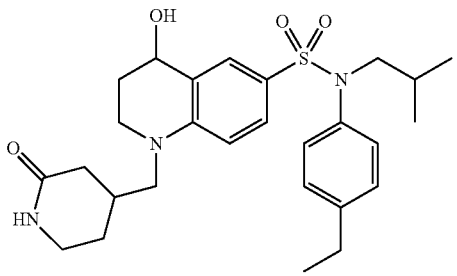<br>Compound 25 | 4-hydroxy-1-(2-oxopiperidin-4-ylmethyl)-1,2,3,4-tetrahydroquinoline-6-sulfonic acid (4-ethylphenyl) isobutylamide<br>$^1$H NMR (DMSO-d6) δ: 0.83 (d, J = 6.0 Hz, 3H), 0.83 (d, J = 6.3 Hz, 3H), 1.18 (t, J = 7.6 Hz, 3H), 1.34-1.50 (m, 2H), 1.74-1.88 (m, 3H), 1.88-2.00 (m, 1H), 2.15-2.29 (m, 2H), 2.60 (q, J = 7.6 Hz, 2H), 3.03-3.14 (m, 1H), 3.14-3.39 (m, 6H), 3.39-3.53 (m, 1H), 4.52 (q, J = 4.9 Hz, 1H), 5.26-5.36 (m, 1H), 6.71 (d, J = 9.0 Hz, 1H), 6.99 (d, J = 8.0 Hz, 2H), 7.08 (dd, J = 8.9, 2.4 Hz, 1H), 7.18 (d, J = 7.9 Hz, 2H), 7.33 (d, J = 2.4 Hz, 1H), 7.45 (s, 1H).<br>MS: [M + H] = 500 |

| | | |
|---|---|---|
| Example 26 | 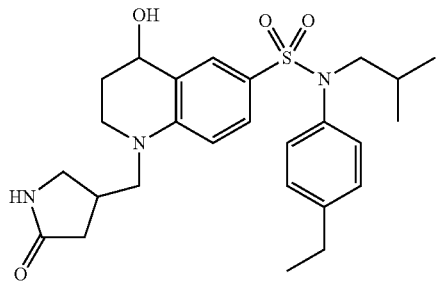

Compound 26 | 4-hydroxy-1-(5-oxopyrrolidin-3-ylmethyl)-1,2,3,4-tetrahydroquinoline-6-sulfonic acid (4-ethylphenyl) isobutylamide<br>$^1$H NMR (DMSO-d6) δ: 0.83 (d, J = 7.1 Hz, 6H), 1.18 (t, J = 7.6 Hz, 3H), 1.34-1.48 (m, 1H), 1.75-1.91 (m, 2H), 1.91-2.03 (m, 1H), 2.19-2.29 (m, 1H), 2.60 (q, J = 7.6 Hz, 2H), 2.72-2.85 (m, 1H), 2.94-3.04 (m, 1H), 3.16-3.27 (m, 2H), 3.28-3.51 (m, 5H), 4.51 (q, J = 4.9 Hz, 1H), 5.32 (d, J = 4.8 Hz, 1H), 6.71 (d, J = 8.9 Hz, 1H), 6.99 (d, J = 7.9 Hz, 2H), 7.05-7.11 (m, 2H), 7.18 (d, J = 8.0 Hz, 2H), 7.35 (s, 1H), 7.55 (s, 1H).<br>MS: [M + H] = 486 |
| Example 27 | 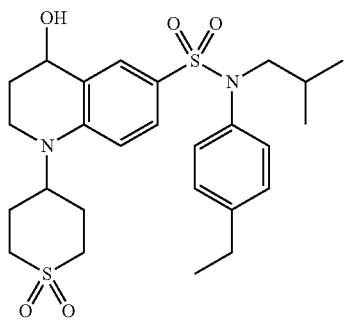

Compound 27 | 1-(1,1-dioxohexahydro-1$\square^6$-thiopyran-4-yl)-4-hydroxy-1,2,3,4-tetrahydroquinoline-6-sulfonic acid (4-ethylphenyl)isobutylamide<br>$^1$H NMR (DMSO-d6) δ: 0.83 (d, J = 6.7 Hz, 6H), 1.19 (t, J = 7.6 Hz, 3H), 1.32-1.49 (m, 1H), 1.73-1.89 (m, 2H), 1.90-2.07 (m, 2H), 2.11-2.30 (m, 2H), 2.61 (q, J = 7.5 Hz, 2H), 3.08-3.18 (m, 2H), 3.18-3.37 (m, 4H), 3.39-3.53 (m, 2H), 4.17-4.33 (m, 1H), 4.44-4.53 (m, 1H), 5.36 (d, J = 5.0 Hz, 1H), 6.87 (d, J = 9.0 Hz, 1H), 7.00 (d, J = 8.3 Hz, 2H), 7.11 (dd, J = 8.8, 2.5 Hz, 1H), 7.18 (d, J = 8.0 Hz, 2H), 7.38 (d, J = 2.6 Hz, 1H).<br>MS: [M + H] = 521 |
| Example 28 | 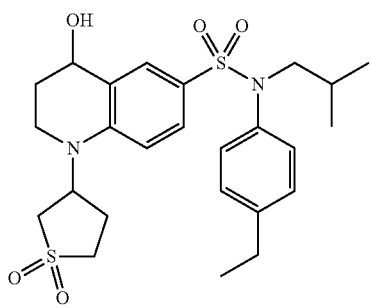

Compound 28 | 1-(1,1-dioxotetrahydro-1lambda*6*-thiophen-3-yl)-4-hydroxy-1,2,3,4-tetrahydroquinoline-6-sulfonic acid (4-ethylphenyl)isobutylamide<br>$^1$H 1H NMR (DMSO-d6) δ: 0.84 (d, J = 6.6 Hz, 6H), 1.19 (t, J = 7.6 Hz, 3H), 1.41 (hept, J = 6.7 Hz, 1H), 1.72-1.96 (m, 2H), 2.23-2.41 (m, 2H), 2.61 (q, J = 7.5 Hz, 2H), 3.11-3.40 (m, 7H), 3.40-3.53 (m, 1H), 4.44-4.55 (m, 1H), 4.83-4.99 (m, 1H), 5.40 (t, J = 6.1 Hz, 1H), 6.88-6.96 (m, 1H), 7.00 (d, J = 8.0 Hz, 2H), 7.09-7.24 (m, 3H), 7.36-7.42 (m, 1H).<br>MS: [M + H] = 507 |
| Example 29 | 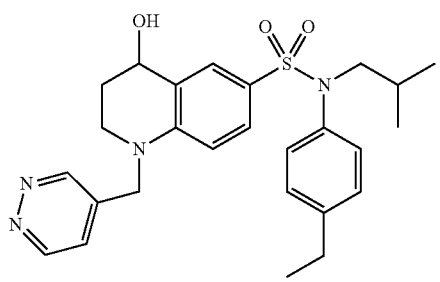

Compound 29 | 4-hydroxy-1-pyridazin-4-ylmethyl-1,2,3,4-tetrahydroquinoline-6-sulfonic acid (4-ethylphenyl)isobutylamide<br>$^1$H NMR (DMSO-d6) δ: 0.82 (d, J = 6.5 Hz, 3H), 0.83 (d, J = 6.5 Hz, 3H), 1.17 (t, J = 7.6 Hz, 3H), 1.33-1.46 (m, 1H), 1.85-2.07 (m, 2H), 2.58 (q, J = 7.6 Hz, 2H), 3.16-3.29 (m, 2H), 3.41-3.52 (m, 1H), 3.52-3.64 (m, 1H), 4.58-4.65 (m, 1H), 4.69 (d, J = 18.3 Hz, 1H), 4.78 (d, J = 18.4 Hz, 1H), 5.41-5.50 (m, 1H), 6.49 (d, J = 8.8 Hz, 1H), 6.96 (d, J = 7.9 Hz, 2H), 7.02 (dd, J = 8.8, 2.3 Hz, 1H), 7.15 (d, J = 8.2 Hz, 2H), 7.41 (d, J = 2.5 Hz, 1H), 7.46 (dd, J = 5.3, 2.4 Hz, 1H), 9.12-9.18 (m, 2H).<br>MS: [M + H] = 481 |

| | | |
|---|---|---|
| Example 30 | 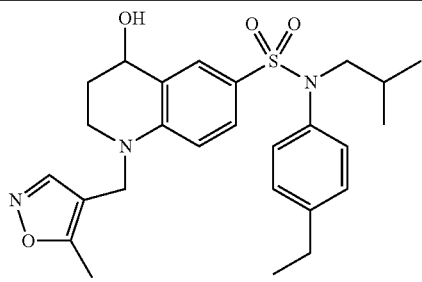

Compound 30 | 4-hydroxy-1-(5-methylisoxazol-4-ylmethyl)-1,2,3,4-tetrahydroquinoline-6-sulfonic acid (4-ethylphenyl)isobutylamide<br>$^1$H NMR (DMSO-d6) δ: 0.83 (d, J = 6.2 Hz, 3H), 0.83 (d, J = 7.3 Hz, 3H), 1.18 (t, J = 7.6 Hz, 3H), 1.33-1.47 (m, 1H), 1.79-1.97 (m, 2H), 2.43 (s, 3H), 2.60 (q, J = 7.7 Hz, 2H), 3.15-3.28 (m, 2H), 3.28-3.50 (m, 2H), 4.37 (d, J = 16.4 Hz, 1H), 4.45 (d, J = 16.5 Hz, 1H), 4.49-4.57 (m, 1H), 5.36 (d, J = 4.5 Hz, 1H), 6.77 (d, J = 8.9 Hz, 1H), 6.97 (d, J = 8.1 Hz, 2H), 7.10 (dd, J = 8.9, 2.4 Hz, 1H), 7.16 (d, J = 8.0 Hz, 2H), 7.37 (d, J = 2.5 Hz, 1H), 8.36 (s, 1H).<br>MS: [M + H] = 484 |
| Example 31 | 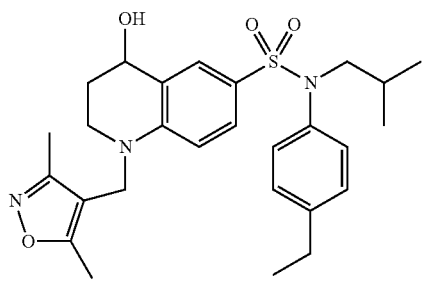

Compound 31 | 1-(3,5-dimethylisoxazol-4-ylmethyl)-4-hydroxy-1,2,3,4-tetrahydroquinoline-6-sulfonic acid (4-ethylphenyl)isobutylamide<br>$^1$H NMR (DMSO-d6) δ: 0.83 (d, J = 6.8 Hz, 3H), 0.83 (d, J = 6.3 Hz, 3H), 1.18 (t, J = 7.6 Hz, 3H), 1.41 (hept, J = 6.6 Hz, 1H), 1.77-1.92 (m, 2H), 2.10 (s, 3H), 2.31 (s, 3H), 2.60 (q, J = 7.6 Hz, 2H), 3.16-3.37 (m, 4H), 4.38 (s, 2H), 4.48-4.58 (m, 1H), 5.36 (d, J = 4.7 Hz, 1H), 6.80 (d, J = 9.0 Hz, 1H), 6.96 (d, J = 8.0 Hz, 2H), 7.12 (dd, J = 8.8, 2.4 Hz, 1H), 7.16 (d, J = 8.1 Hz, 2H), 7.38 (d, J = 2.4 Hz, 1H).<br>MS: [M + H] = 498 |
| Example 32 | 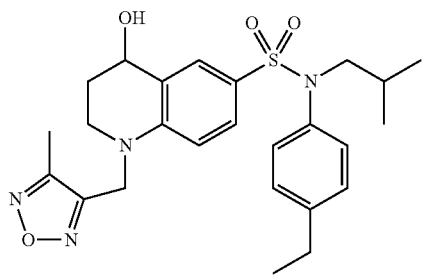

Compound 32 | 4-hydroxy-1-(4-methylfurazan-3-ylmethyl)-1,2,3,4-tetrahydroquinoline-6-sulfonicacid (4-ethylphenyl)isobutylamide<br>$^1$H 1H NMR (DMSO-d6) δ: 0.83 (d, J = 6.3 Hz, 3H), 0.83 (d, J = 6.4 Hz, 3H), 1.18 (t, J = 7.6 Hz, 3H), 1.40 (hept, J = 6.7 Hz, 1H), 1.80-2.00 (m, 2H), 2.36 (s, 3H), 2.60 (q, J = 7.7 Hz, 2H), 3.16-3.29 (m, 2H), 3.36-3.56 (m, 2H), 4.57 (q, J = 4.9 Hz, 1H), 4.84 (s, 2H), 5.42 (d, J = 4.7 Hz, 1H), 6.75 (d, J = 8.8 Hz, 1H), 6.97 (d, J = 7.9 Hz, 2H), 7.08 (dd, J = 8.8, 2.4 Hz, 1H), 7.16 (d, J = 8.0 Hz, 2H), 7.41 (d, J = 2.3 Hz, 1H).<br>MS: [M + H] = 485 |
| Example 33 | 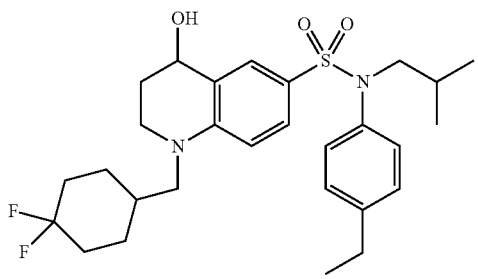

Compound 33 | 1-(4,4-difluorocyclohexylmethyl)-4-hydroxy-1,2,3,4-tetrahydroquinoline-6-sulfonic acid (4-ethylphenyl)isobutylamide<br>$^1$H 1H NMR (DMSO-d6) δ: 0.83 (d, J = 6.2 Hz, 3H), 0.83 (d, J = 7.3 Hz, 3H), 1.19 (t, J = 7.5 Hz, 3H), 1.23-1.33 (m, 2H), 1.34-1.49 (m, J = 7.2 Hz, 1H), 1.65-1.95 (m, 7H), 2.02 (m, 2H), 2.60 (q, J = 7.6 Hz, 2H), 3.16-3.36 (m, 5H), 3.38-3.52 (m, 1H), 4.51 (q, J = 4.9 Hz, 1H), 5.31 (d, J = 4.8 Hz, 1H), 6.67 (d, J = 8.9 Hz, 1H), 7.00 (d, J = 8.0 Hz, 2H), 7.09 (dd, J = 9.0, 2.4 Hz, 1H), 7.17 (d, J = 8.0 Hz, 2H), 7.32 (d, J = 2.4 Hz, 1H).<br>MS: [M + H] = 521 |
| Example 34 | 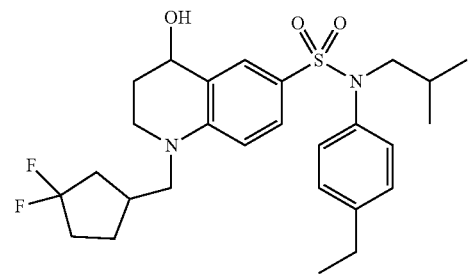

Compound 34 | 1-(3,3-difluorocyclopentylmethyl)-4-hydroxy-1,2,3,4-tetrahydroquinoline-6-sulfonic acid (4-ethylphenyl)isobutylamide<br>$^1$H NMR (DMSO-d6) δ: 0.83 (d, J = 6.4 Hz, 3H), 0.83 (d, J = 6.2 Hz, 3H), 1.18 (t, J = 7.6 Hz, 3H), 1.41 (hept, J = 6.9 Hz, 1H), 1.47-1.61 (m, 1H), 1.76-1.97 (m, 4H), 1.97-2.11 (m, 1H), 2.11-2.32 (m, 2H), 2.60 (q, J = 7.6 Hz, 2H), 3.16-3.27 (m, 2H), 3.28-3.50 (m, 5H), 4.45-4.56 (m, 1H), 5.32 (d, J = 4.8 Hz, 1H), 6.70 (d, J = 8.9 Hz, 1H), 6.99 (d, J = 7.9 Hz, 2H), 7.09 (dd, J = 8.8, 2.4 Hz, 1H), 7.17 (d, J = 8.1 Hz, 2H), 7.34 (d, J = 2.4 Hz, 1H).<br>MS: [M + H] = 507 |

| Example 35 | 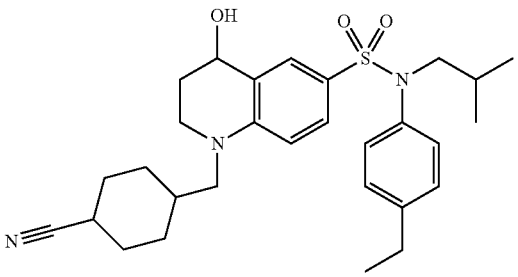
Compound 35 | 1-(4-cyanocyclohexylmethyl)-4-hydroxy-1,2,3,4-tetrahydroquinoline-6-sulfonicacid (4-ethylphenyl)isobutylamide
$^1$H NMR (DMSO-d6) δ: 0.83 (d, J = 6.6 Hz, 3H), 0.83 (d, J = 6.3 Hz, 3H), 1.04 (q, J = 12.9 Hz, 2H), 1.19 (t, J = 7.6 Hz, 3H), 1.35-1.54 (m, 3H), 1.64-1.87 (m, 5H), 2.03 (d, J = 12.6 Hz, 2H), 2.56-2.66 (m, 3H), 3.11-3.35 (m, 5H), 3.36-3.48 (m, 1H), 4.50 (q, J = 4.8 Hz, 1H), 5.31 (d, J = 4.8 Hz, 1H), 6.61 (d, J = 9.0 Hz, 1H), 6.99 (d, J = 8.2 Hz, 2H), 7.09 (dd, J = 8.9, 2.4 Hz, 1H), 7.17 (d, J = 8.0 Hz, 2H), 7.31 (d, J = 2.4 Hz, 1H).
MS: [M + H] = 510 |
| Example 36 | 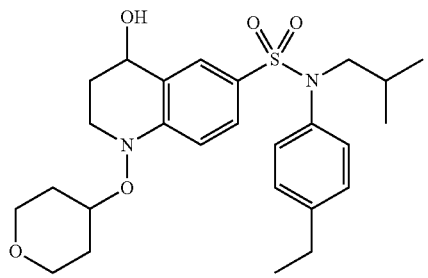
Compound 36 | 4-hydroxy-1-(tetrahydropyran-4-yloxy)-1,2,3,4-tetrahydroquinoline-6-sulfonic acid (4-ethylphenyl)isobutylamide
$^1$H NMR (DMSO) δ: 0.84 (d, J = 6.7 Hz, 3H), 0.84 (d, J = 6.2 Hz, 3H), 1.19 (t, J = 7.6 Hz, 3H), 1.41 (hept, J = 7.0 Hz, 1H), 1.51-1.66 (m, 2H), 1.88-2.05 (m, 3H), 2.07-2.20 (m, 1H), 2.61 (q, J = 7.5 Hz, 2H), 3.20-3.29 (m, 2H), 3.29-3.47 (m, 4H), 3.85-3.96 (m, 2H), 4.03-4.16 (m, 1H), 4.54 (q, J = 5.6 Hz, 1H), 5.49 (d, J = 5.4 Hz, 1H), 6.99 (d, J = 7.9 Hz, 2H), 7.11 (d, J = 8.7 Hz, 1H), 7.19 (d, J = 7.9 Hz, 2H), 7.28 (dd, J = 8.8, 2.3 Hz, 1H), 7.44 (d, J = 2.3 Hz, 1H).
MS: [M + H] = 489 |
| Example 37 | 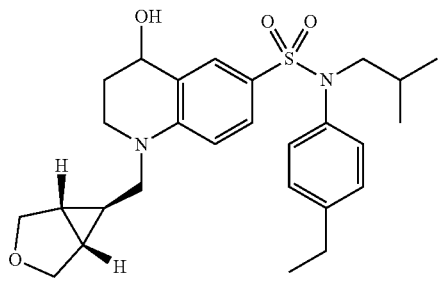
Compound 37 | 4-hydroxy-1-[(1S,5R,6S)-1-(3-oxabicyclo[3.1.0]hex-6-yl)methyl]-1,2,3,4-tetrahydroquinoline-6-sulfonic acid (4-ethylphenyl)isobutylamide
$^1$H NMR (DMSO-d6) δ: 0.78-0.91 (m, 7H), 1.18 (t, J = 7.6 Hz, 3H), 1.33-1.48 (m, 1H), 1.60-1.70 (m, 2H), 1.75-1.93 (m, 2H), 2.60 (q, J = 7.5 Hz, 2H), 3.15-3.29 (m, 3H), 3.29-3.51 (m, 3H), 3.56 (dd, J = 8.4, 2.7 Hz, 2H), 3.72 (dd, J = 8.3, 2.0 Hz, 2H), 4.50 (q, J = 4.9 Hz, 1H), 5.31 (d, J = 5.0 Hz, 1H), 6.71 (d, J = 9.0 Hz, 1H), 6.99 (d, J = 8.0 Hz, 2H), 7.11 (dd, J = 8.9, 2.4 Hz, 1H), 7.17 (d, J = 7.9 Hz, 2H), 7.34 (d, J = 2.4 Hz, 1H).
MS: [M + H] = 465 |
| Example 38 | 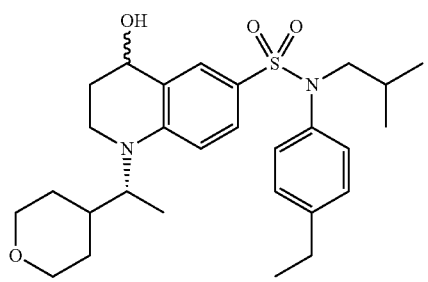
Compound 38 | 4-hydroxy-1-[(R)-1-(tetrahydropyran-4-yl)ethyl]-1,2,3,4-tetrahydroquinoline-6-sulfonic acid (4-ethylphenyl)isobutylamide
$^1$H NMR (DMSO-d6) δ: 0.83 (d, J = 6.2 Hz, 3H), 0.83 (d, J = 6.2 Hz, 3H), 1.05-1.15 (m, 4H), 1.19 (t, J = 7.6 Hz, 3H), 1.22-1.56 (m, 3H), 1.55-1.65 (m, 1H), 1.71-1.94 (m, 3H), 2.61 (q, J = 7.5 Hz, 2H), 3.11-3.30 (m, 6H), 3.76-3.85 (m, 2H), 3.86-3.95 (m, 1H), 4.47 (q, J = 4.8 Hz, 1H), 5.30 (d, J = 4.8 Hz, 1H), 6.86 (d, J = 9.1 Hz, 1H), 7.01 (d, J = 8.1 Hz, 2H), 7.08 (dd, J = 9.1, 2.5 Hz, 1H), 7.18 (d, J = 8.0 Hz, 2H), 7.33 (d, J = 2.4 Hz, 1H).
MS: [M + H] = 501 |
| Example 39 | 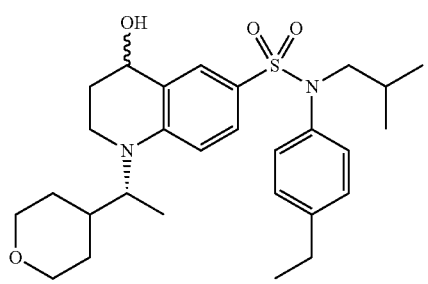
Compound 39 | 4-hydroxy-1-[(R)-1-(tetrahydropyran-4-yl)ethyl]-1,2,3,4-tetrahydroquinoline-6-sulfonic acid (4-ethylphenyl)isobutylamide
$^1$H NMR (DMSO-d6) δ: 0.83 (d, J = 6.6 Hz, 3H), 0.83 (d, J = 6.7 Hz, 3H), 1.03-1.23 (m, 7H), 1.26-1.49 (m, 3H), 1.54-1.64 (m, 1H), 1.72-1.88 (m, 3H), 2.60 (q, J = 7.6 Hz, 2H), 3.12-3.40 (m, 6H), 3.72-3.97 (m, 3H), 4.49 (q, J = 5.0 Hz, 1H), 5.29 (d, J = 4.9 Hz, 1H), 6.86 (d, J = 9.2 Hz, 1H), 7.00 (d, J = 8.3 Hz, 2H), 7.06 (dd, J = 9.0, 2.5 Hz, 1H), 7.17 (d, J = 8.3 Hz, 2H), 7.33 (d, J = 2.4 Hz, 1H).
MS: [M + H] = 501 |

| | | |
|---|---|---|
| Example 40 | 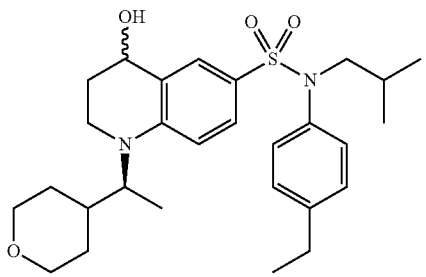<br>Compound 40 | 4-hydroxy-1-[(S)-1-(tetrahydropyran-4-yl)ethyl]-1,2,3,4-tetrahydroquinoline-6-sulfonic acid (4-ethylphenyl)isobutylamide<br><sup></sup>1H NMR (DMSO-d6) δ: 0.83 (d, J = 6.7 Hz, 3H), 0.83 (d, J = 6.3 Hz, 3H), 1.12 (d, J = 6.5 Hz, 4H), 1.19 (t, J = 7.6 Hz, 3H), 1.26-1.55 (m, 3H), 1.56-1.67 (m, 1H), 1.72-1.91 (m, 3H), 2.61 (q, J = 7.5 Hz, 2H), 3.11-3.31 (m, 6H), 3.74-3.87 (m, 2H), 3.86-3.95 (m, 1H), 4.4 (q, J = 4.7 Hz, 1H), 5.30 (d, J = 4.8 Hz, 1H), 6.86 (d, J = 9.1 Hz, 1H), 7.01 (d, J = 8.1 Hz, 2H), 7.08 (dd, J = 9.1, 2.5 Hz, 1H), 7.18 (d, J = 8.0 Hz, 2H), 7.33 (d, J = 2.4 Hz, 1H).<br>MS: [M + H] = 501 |
| Example 41 | 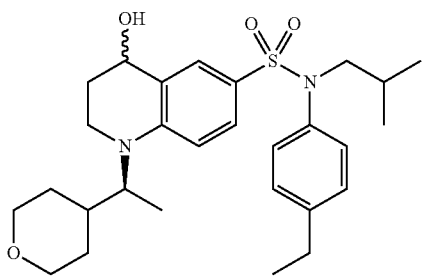<br>Compound 41 | 4-hydroxy-1-[(S)-1-(tetrahydropyran-4-yl)ethyl]-1,2,3,4-tetrahydroquinoline-6-sulfonic acid (4-ethylphenyl)isobutylamide<br>$^1$H NMR (DMSO-d6) δ: 0.83 (d, J = 6.7 Hz, 3H), 0.83 (d, J = 6.7 Hz, 3H), 1.04-1.22 (m, 7H), 1.26-1.50 (m, 3H), 1.55-1.63 (m, 1H), 1.71-1.88 (m, 3H), 2.60 (q, J = 7.6 Hz, 2H), 3.13-3.35 (m, 6H), 3.76-3.94 (m, 3H), 4.49 (q, J = 5.1 Hz, 1H), 5.29 (d, J = 4.9 Hz, 1H), 6.86 (d, J = 9.2 Hz, 1H), 6.98-7.02 (m, 2H), 7.06 (dd, J = 9.0, 2.5 Hz, 1H), 7.17 (d, J = 8.3 Hz, 2H), 7.33 (d, J = 2.5 Hz, 1H).<br>MS: [M + H] = 501 |
| Example 42 | 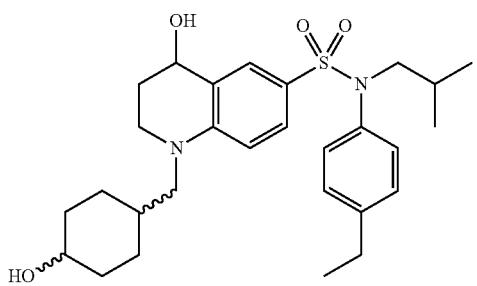<br>Compound 42 | 4-hydroxy-1-(4-hydroxycyclohexylmethyl)-1,2,3,4-tetrahydroquinoline-6-sulfonic acid (4-ethylphenyl)isobutylamide<br>$^1$H NMR (DMSO-d6) δ: 0.83 (d, J = 6.2 Hz, 3H), 0.83 (d, J = 6.8 Hz, 3H), 0.95-1.15 (m, 4H), 1.18 (t, J = 7.6 Hz, 3H), 1.41 (hept, J = 6.7 Hz, 1H), 1.56-1.74 (m, 3H), 1.74-1.91 (m, 4H), 2.60 (q, J = 7.6 Hz, 2H), 3.11-3.38 (m, 6H), 3.37-3.50 (m, 1H), 4.44-4.55 (m, 2H), 5.30 (d, J = 4.8 Hz, 1H), 6.60 (d, J = 9.0 Hz, 1H), 6.99 (d, J = 7.9 Hz, 2H), 7.09 (dd, J = 8.9, 2.5 Hz, 1H), 7.17 (d, J = 7.9 Hz, 2H), 7.31 (d, J = 2.5 Hz, 1H).<br>MS: [M + H] = 501<br>Retention time: 8.257 min |
| Example 43 | 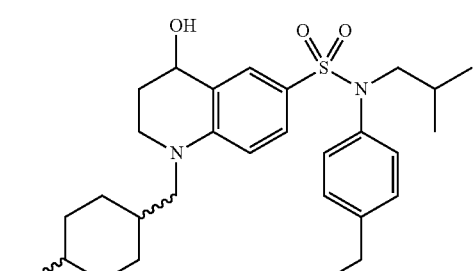<br>Compound 43 | 4-hydroxy-1-(4-hydroxycyclohexylmethyl)-1,2,3,4-tetrahydroquinoline-6-sulfonic acid (4-ethylphenyl)isobutylamide<br>$^1$H NMR (DMSO-d6) δ: 0.83 (d, J = 6.3 Hz, 3H), 0.83 (d, J = 6.4 Hz, 3H), 1.18 (t, J = 7.6 Hz, 3H), 1.31-1.49 (m, 7H), 1.55-1.68 (m, 2H), 1.69-1.89 (m, 3H), 2.60 (q, J = 7.6 Hz, 2H), 3.12-3.37 (m, 5H), 3.40-3.50 (m, 1H), 3.78 (s, 1H), 4.29 (d, J = 3.2 Hz, 1H), 4.50 (q, J = 4.8 Hz, 1H), 5.30 (d, J = 4.8 Hz, 1H), 6.60 (d, J = 9.0 Hz, 1H), 6.99 (d, J = 7.9 Hz, 2H), 7.11 (dd, J = 8.9, 2.4 Hz, 1H), 7.17 (d, J = 8.1 Hz, 2H), 7.30 (d, J = 2.4 Hz, 1H).<br>MS: [M + H] = 501<br>Retention time: 8.430 min |
| Example 44 | 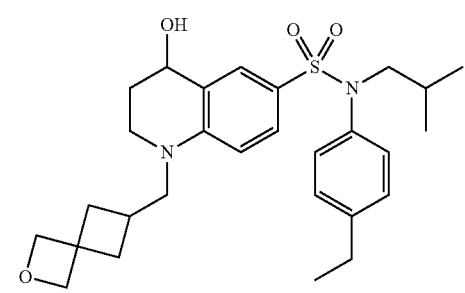<br>Compound 44 | 4-hydroxy-1-(2-oxaspiro[3.3]hept-6-ylmethyl)-1,2,3,4-tetrahydroquinoline-6-sulfonic acid (4-ethylphenyl)isobutylamide<br>$^1$H NMR (DMSO-d6) δ: 0.83 (d, J = 6.8 Hz, 3H), 0.83 (d, J = 6.3 Hz, 3H), 1.18 (t, J = 7.6 Hz, 3H), 1.34-1.47 (m, 1H), 1.74-1.85 (m, 2H), 1.89-2.02 (m, 2H), 2.23-2.54 (m, 4H), 2.60 (q, J = 7.7 Hz, 2H), 3.15-3.25 (m, 2H), 3.25-3.46 (m, 3H), 4.43-4.53 (m, 3H), 4.58 (s, 2H), 5.29 (d, J = 4.8 Hz, 1H), 6.61 (d, J = 8.9 Hz, 1H), 6.99 (d, J = 7.9 Hz, 2H), 7.08 (dd, J = 8.8, 2.5 Hz, 1H), 7.17 (d, J = 8.1 Hz, 2H), 7.31 (d, J = 2.5 Hz, 1H).<br>MS: [M + H] = 499 |

| Example 46 | 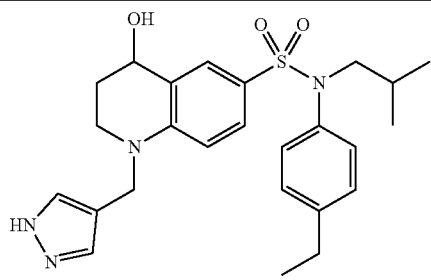

Compound 45 | 4-hydroxy-1-(1H-pyrazol-4-ylmethyl)-1,2,3,4-tetrahydroquinoline-6-sulfonic acid (4-ethylphenyl) isobutylamide
$^1$H NMR (DMSO-d6) δ: 0.82 (d, J = 6.5 Hz, 3H), 0.83 (d, J = 6.5 Hz, 3H), 1.18 (t, J = 7.6 Hz, 3H), 1.32-1.48 (m, 1H), 1.79-1.94 (m, 2H), 2.60 (q, J = 7.6 Hz, 2H), 3.15-3.28 (m, 2H), 3.28-3.54 (m, 2H), 4.33-4.54 (m, 3H), 5.31 (d, J = 4.8 Hz, 1H), 6.80 (d, J = 8.9 Hz, 1H), 6.97 (d, J = 7.8 Hz, 2H), 7.09 (dd, J = 8.8, 2.4 Hz, 1H), 7.17 (d, J = 8.0 Hz, 2H), 7.33 (d, J = 2.5 Hz, 1H), 7.43-7.74 (m, 2H), 12.71 (s, 1H).
MS: [M + H] = 469 |
| Example 47 | 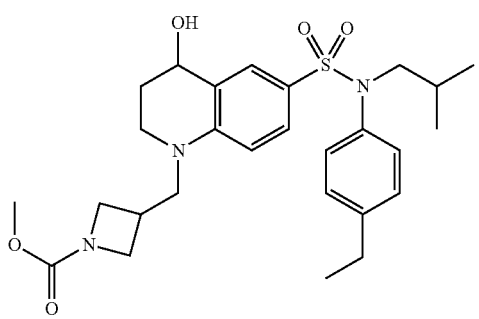

Compound 46 | methyl 3-{6-[(4-ethylphenyl)isobutylsulfamoyl]-4-hydroxy-3,4-dihydro-2H-quinolin-1-ylmethyl} azetidine-1-carboxylate
$^1$H NMR (DMSO-d6) δ: 0.83 (d, J = 6.7 Hz, 3H), 0.83 (d, J = 6.4 Hz, 3H), 1.18 (t, J = 7.5 Hz, 3H), 1.41 (hept, J = 6.7 Hz, 1H), 1.81 (p, J = 5.7, 4.9 Hz, 2H), 2.60 (q, J = 7.5 Hz, 2H), 2.85-3.00 (m, 1H), 3.15-3.27 (m, 2H), 3.27-3.47 (m, 2H), 3.56 (s, 3H), 3.58-3.65 (m, 2H), 3.65-3.78 (m, 2H), 3.89-4.06 (m, 2H), 4.49 (q, J = 4.9 Hz, 1H), 5.32 (d, J = 4.8 Hz, 1H), 6.72 (d, J = 8.9 Hz, 1H), 6.99 (d, J = 8.1 Hz, 2H), 7.08 (dd, J = 8.8, 2.4 Hz, 1H), 7.18 (d, J = 8.0 Hz, 2H), 7.34 (d, J = 2.4 Hz, 1H).
MS: [M + H] = 516 |
| Example 48 | 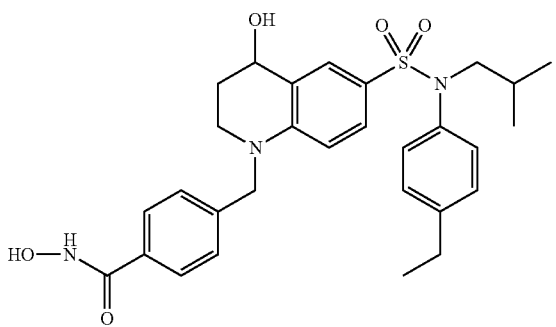

Compound 47 | 4-{6-[(4-ethylphenyl)isobutylsulfamoyl]-4-hydroxy-3,4-dihydro-2H-quinolin-1-ylmethyl}-N-hydroxybenzamide
1H NMR (DMSO-d6) δ: 0.82 (d, J = 6.6 Hz, 3H), 0.83 (d, J = 6.3 Hz, 3H), 1.17 (t, J = 7.6 Hz, 3H), 1.33-1.48 (m, 1H), 1.84-2.02 (m, 2H), 2.59 (q, J = 7.7 Hz, 2H), 3.15-3.28 (m, 2H), 3.39-3.49 (m, 1H), 3.50-3.65 (m, 1H), 4.52-4.77 (m, 3H), 5.41 (d, J = 4.8 Hz, 1H), 6.52 (d, J = 8.9 Hz, 1H), 6.97 (d, J = 8.0 Hz, 2H), 7.05 (dd, J = 8.8, 2.4 Hz, 1H), 7.16 (d, J = 7.9 Hz, 2H), 7.30 (d, J = 8.0 Hz, 2H), 7.38 (d, J = 2.4 Hz, 1H), 7.72 (d, J = 7.9 Hz, 2H), 9.00 (s, 1H), 11.17 (s, 1H).
MS: [M + H] = 538 |
| Example 49 | 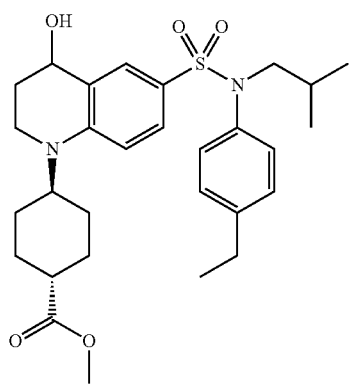

Compound 48 | methyl (1R,4R)-4-(6-(N-(4-ethylphenyl)-N-isobutyl-sulfamoyl)-4-hydroxy-3,4-dihydroquinolin-1(2H)-yl)cyclohexane-1-carboxylate
$^1$H NMR (DMSO-d6) δ: 0.83 (d, J = 6.7 Hz, 3H), 0.83 (d, J = 6.6 Hz, 3H), 1.19 (t, J = 7.6 Hz, 3H), 1.40 (hept, J = 6.7 Hz, 1H), 1.50-1.85 (m, 8H), 1.94-2.03 (m, 2H), 2.29-2.41 (m, 1H), 2.60 (q, J = 7.6 Hz, 2H), 3.15-3.35 (m, 4H), 3.61 (s, 3H), 3.68-3.82 (m, 1H), 4.46 (q, J = 5.0 Hz, 1H), 5.30 (d, J = 5.0 Hz, 1H), 6.79 (d, J = 9.2 Hz, 1H), 7.00 (d, J = 8.3 Hz, 2H), 7.10 (dd, J = 8.9, 2.4 Hz, 1H), 7.18 (d, J = 8.4 Hz, 2H), 7.34 (d, J = 2.3 Hz, 1H).
MS: [M + H] = 529 |

| | | |
|---|---|---|
| Example 50 | 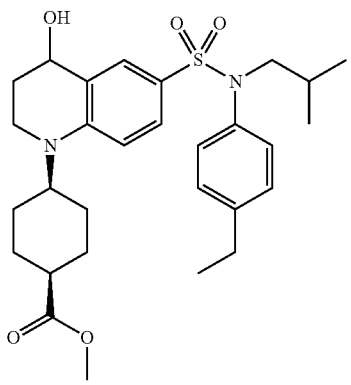<br>Compound 49 | methyl (1S,4S)-4-(6-(N-(4-ethylphenyl)-N-isobutyl-sulfamoyl)-4-hydroxy-3,4-dihydroquinolin-1(2H)-yl)cyclohexane-1-carboxylate<br>$^1$H NMR (DMSO-d6) δ: 0.83 (d, J = 6.6 Hz, 3H), 0.83 (d, J = 6.6 Hz, 3H), 1.19 (t, J = 7.6 Hz, 3H), 1.34-1.47 (m, 1H), 1.52-1.86 (m, 8H), 2.14 (d, J = 11.4 Hz, 2H), 2.60 (q, J = 7.6 Hz, 2H), 2.69-2.75 (m, 1H), 3.16-3.25 (m, 4H), 3.67 (s, 3H), 3.70-3.83 (m, 1H), 4.46 (q, J = 5.1 Hz, 1H), 5.30 (d, J = 5.0 Hz, 1H), 6.77 (d, J = 9.2 Hz, 1H), 7.00 (d, J = 8.4 Hz, 2H), 7.10 (dd, J = 9.0, 2.5 Hz, 1H), 7.18 (d, J = 8.3 Hz, 2H), 7.34 (d, J = 2.5 Hz, 1H).<br>MS: [M + H] = 529 |
| Example 51 | 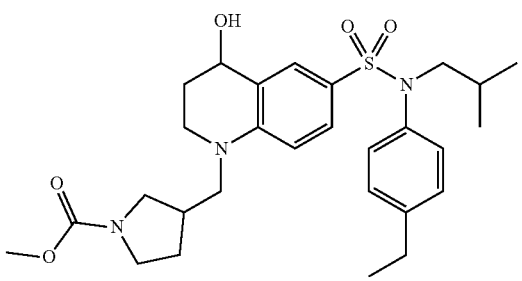<br>Compound 50 | methyl 3-{6-[(4-ethylphenyl)isobutylsulfamoyl]-4-hydroxy-3,4-dihydro-2H-quinolin-1-ylmethyl}pyrrolidine-1-carboxylate<br>$^1$H NMR (DMSO-d6) δ: 0.83 (d, J = 6.1 Hz, 3H), 0.83 (d, J = 6.1 Hz, 3H), 1.18 (t, J = 7.6 Hz, 3H), 1.41 (hept, J = 6.7 Hz, 1H), 1.56-1.74 (m, 1H), 1.76-1.90 (m, 2H), 1.90-2.04 (m, 1H), 2.55-2.66 (m, 3H), 3.03 (t, J = 9.0 Hz, 1H), 3.16-3.29 (m, 3H), 3.29-3.50 (m, 6H), 3.57 (d, J = 5.4 Hz, 3H), 4.51 (q, J = 4.9 Hz, 1H), 5.30-5.35 (m, 1H), 6.71 (d, J = 9.0 Hz, 1H), 6.99 (d, J = 8.0 Hz, 2H), 7.06-7.11 (m, 1H), 7.18 (d, J = 8.1 Hz, 2H), 7.31-7.36 (m, 1H).<br>MS: [M + H] = 530 |
| Example 52 | 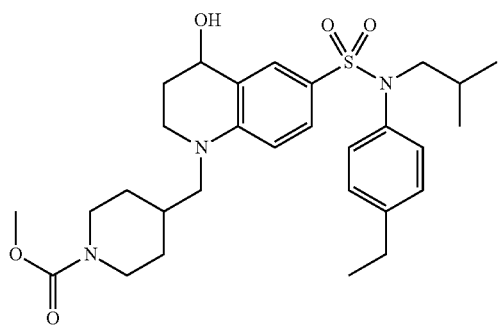<br>Compound 51 | methyl 4-{6-[(4-ethylphenyl)isobutylsulfamoyl]-4-hydroxy-3,4-dihydro-2H-quinolin-1-ylmethyl}piperidine-1-carboxylate<br>1H NMR (DMSO-d6) δ: 0.83 (d, J = 6.2 Hz, 3H), 0.83 (d, J = 6.1 Hz, 3H), 1.04-1.24 (m, 5H), 1.34-1.48 (m, J = 6.6 Hz, 1H), 1.64 (d, J = 12.8 Hz, 2H), 1.77-1.87 (m, 2H), 1.85-2.01 (m, 1H), 2.60 (q, J = 7.6 Hz, 2H), 2.66-2.82 (m, 2H), 3.15-3.38 (m, 5H), 3.38-3.49 (m, 1H), 3.58 (s, 3H), 3.90-4.09 (m, 2H), 4.51 (q, J = 4.7 Hz, 1H), 5.31 (d, J = 4.7 Hz, 1H), 6.66 (d, J = 9.0 Hz, 1H), 6.99 (d, J = 8.1 Hz, 2H), 7.08 (dd, J = 9.1, 2.4 Hz, 1H), 7.17 (d, J = 7.9 Hz, 2H), 7.32 (d, J = 2.4 Hz, 1H).<br>MS: [M + H] = 544 |
| Example 53 | 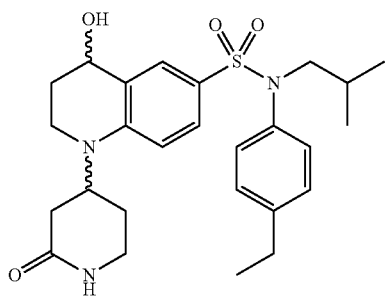<br>Compound 52 | Diastereoisomer 1<br>4-hydroxy-1-(2-oxopiperidin-4-yl)-1,2,3,4-tetrahydro-quinoline-6-sulfonic acid (4-ethylphenyl)isobutylamide<br>$^1$H NMR (DMSO-d6) δ: 0.83 (d, J = 6.4 Hz, 6H), 1.19 (t, J = 7.6 Hz, 3H), 1.41 (hept, J = 6.9 Hz, 1H), 1.73-2.00 (m, 4H), 2.23-2.36 (m, 1H), 2.40-2.54 (m, 1H), 2.61 (q, J = 7.6 Hz, 2H), 3.14-3.40 (m, 6H), 4.22-4.35 (m, 1H), 4.49 (q, J = 5.0 Hz, 1H), 5.33 (d, J = 4.8 Hz, 1H), 6.87 (d, J = 9.0 Hz, 1H), 7.00 (d, J = 8.1 Hz, 2H), 7.10 (dd, J = 8.8, 2.5 Hz, 1H), 7.18 (d, J = 7.9 Hz, 2H), 7.35 (d, J = 2.4 Hz, 1H), 7.57-7.62 (m, 1H).<br>MS: [M + H] = 486<br>Retention time: 7.671 min |

Example 54

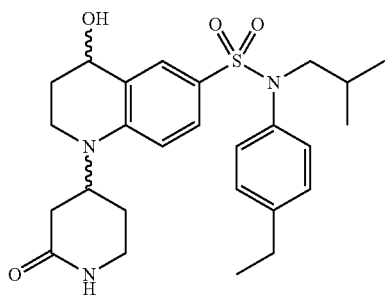

Compound 53

Diastereoisomer 2
4-hydroxy-1-(2-oxopiperidin-4-yl)-1,2,3,4-tetrahydro-quinoline-6-sulfonic acid (4-ethylphenyl)isobutylamide
$^1$H NMR (DMSO-d6) δ: 0.83 (d, J = 6.6 Hz, 3H), 0.84 (d, J = 6.1 Hz, 3H), 1.19 (t, J = 7.6 Hz, 3H), 1.34-1.47 (m, 1H), 1.71-1.90 (m, 3H), 1.91-2.05 (m, 1H), 2.23-2.44 (m, 2H), 2.61 (q, J = 7.6 Hz, 2H), 3.14-3.37 (m, 6H), 4.22-4.34 (m, 1H), 4.48 (q, J = 5.2 Hz, 1H), 5.34 (d, J = 5.0 Hz, 1H), 6.88 (d, J = 9.1 Hz, 1H), 7.00 (d, J = 8.0 Hz, 2H), 7.10 (dd, J = 8.9, 2.4 Hz, 1H), 7.18 (d, J = 8.0 Hz, 2H), 7.37 (d, J = 2.4 Hz, 1H), 7.57-7.65 (m, 1H).
MS: [M + H] = 486
Retention time: 7.961 min

Example 55

4-oxo-1-piperidin-4-ylmethyl-1,2,3,4-tetrahydroquinoline-6-sulfonic Acid (4-ethylphenyl)isobutylamide

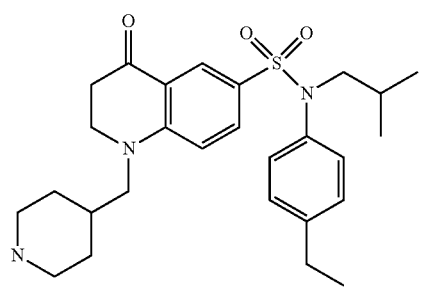

Compound 54

Trifluoroacetic acid (270 µl; 3.54 mmol) is added to a solution of tert-butyl 4-{6-[(4-ethylphenyl)isobutylsulfamoyl]-4-oxo-3,4-dihydro-2H-quinolin-1-ylmethyl}piperidine-1-carboxylate (0.14 g; 0.24 mmol) in dichloromethane (2 ml).

The reaction medium is stirred for 12 hours, hydrolyzed with aqueous 1M sodium hydroxide solution and extracted with dichloromethane. The organic phase is washed with water, dried (NaSO$_4$), filtered and concentrated.

The 4-oxo-1-piperidin-4-ylmethyl-1,2,3,4-tetrahydroquinoline-6-sulfonic acid (4-ethylphenyl)isobutylamide (0.12 g; 100%) is obtained in the form of a yellow solid.

$^1$H NMR (DMSO-d6) δ: 0.83 (d, J=6.7 Hz, 6H), 1.14-1.29 (m, 5H), 1.41 (hept, J=6.8 Hz, 1H), 1.63-1.76 (m, 2H), 1.78-1.91 (m, 1H), 2.42-2.72 (m, 6H), 2.93-3.09 (m, 2H), 3.23 (d, J=7.2 Hz, 2H), 3.25-3.46 (m, 3H), 3.62-3.67 (m, 2H), 6.97-7.03 (m, 3H), 7.16-7.21 (m, 2H), 7.31-7.38 (m, 1H), 7.77 (d, J=2.5 Hz, 1H)

MS: [M+H]=483

Example 56

Synthesis of 4-oxo-1-piperidin-4-yl-1,2,3,4-tetrahydroquinoline-6-sulfonic Acid (4-ethylphenyl)isobutylamide

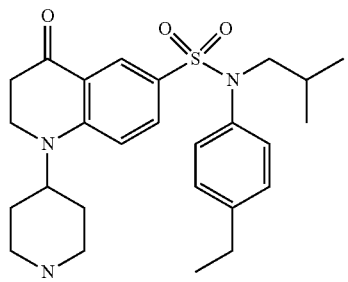

Compound 55

1. Synthesis of Intermediate 56.1

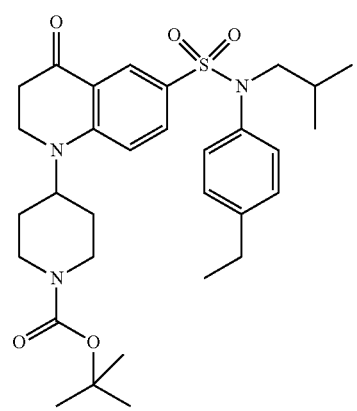 [SMILES: CCc1ccc(N(CC(C)C)S(=O)(=O)c2ccc3c(c2)C(=O)CCN3C2CCN(C(=O)OC(C)(C)C)CC2)cc1]

methyl 4-{6-[(4-ethylphenyl)isobutylsulfamoyl]-4-oxo-3,4-dihydro-2H-quinolin-1-yl}piperidine-1-carboxylate With a procedure similar to that described in example 1, methyl 4-{6-[(4-ethylphenyl)isobutylsulfamoyl]-4-oxo-3,4- dihydro-2H-quinolin-1-yl}piperidine-1-carboxylate (230 mg; 58%) is obtained in the form of a colorless yellow solid with a compliant ¹H NMR.

MS: [M+H]=570

2. Synthesis of 4-oxo-1-piperidin-4-yl-1,2,3,4-tetrahydroquinoline-6-sulfonic Acid (4-ethylphenyl)isobutylamide By following the same procedure as for example 55, 4-oxo-1-piperidin-4-yl-1,2,3,4-tetrahydroquinoline-6-sulfonic acid (4-ethylphenyl)isobutylamide (0.15 mg; 90%) is obtained in the form of a yellow solid.

¹H NMR (DMSO-d6) δ: 0.83 (d, J=6.7 Hz, 6H), 1.18 (t, J=7.6 Hz, 3H), 1.40 (hept, J=6.6 Hz, 1H), 1.56-1.72 (m, 4H), 2.00-2.23 (m, 1H), 2.54-2.71 (m, 6H), 2.97-3.06 (m, 2H), 3.23 (d, J=7.2 Hz, 2H), 3.54 (t, J=7.0 Hz, 2H), 3.96 (p, J=8.0 Hz, 1H), 7.01 (d, J=8.3 Hz, 2H), 7.16-7.22 (m, 3H), 7.36 (dd, J=9.1, 2.5 Hz, 1H), 7.81 (d, J=2.5 Hz, 1H).

MS: [M+H]=470

Example 57

4-hydroxy-1-piperidin-4-ylmethyl-1,2,3,4-tetrahydroquinoline-6-sulfonic Acid (4-ethylphenyl)isobutylamide

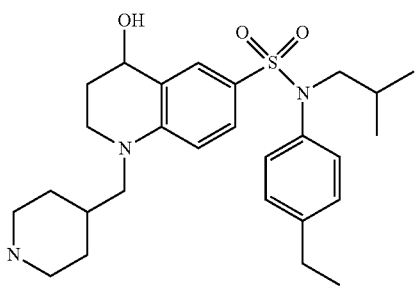

Compound 56

With the same procedure as for example 2, 4-hydroxy-1-piperidin-4-ylmethyl-1,2,3,4-tetrahydroquinoline-6-sulfonic acid (4-ethylphenyl)isobutylamide (4.5 mg; 25%) is obtained in the form of a white solid.

¹H NMR (DMSO) δ: 0.83 (dd, J=6.5, 2.8 Hz, 6H), 1.13-1.33 (m, 5H), 1.33-1.48 (m, 1H), 1.69 (d, J=12.9 Hz, 2H), 1.75-1.96 (m, 3H), 2.46-2.66 (m, 5H), 3.11 (d, J=12.2 Hz, 2H), 3.15-3.50 (m, 5H), 4.47-4.56 (m, 1H), 5.26-5.43 (m, 1H), 6.64 (d, J=8.9 Hz, 1H), 6.99 (d, J=8.2 Hz, 2H), 7.10 (dd, J=8.8, 2.5 Hz, 1H), 7.18 (d, J=7.9 Hz, 2H), 7.32 (d, J=2.5 Hz, 1H), 8.35 (s, 1H).

MS: [M+H]=485

Example 58

4-hydroxy-1-piperidin-4-yl-1,2,3,4-tetrahydroquinoline-6-sulfonic Acid (4-ethylphenyl)isobutylamide

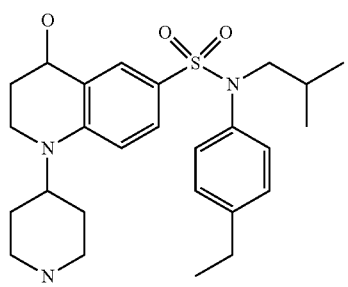

Compound 57

With the same procedure as for example 2, 4-hydroxy-1-piperidin-4-yl-1,2,3,4-tetrahydroquinoline-6-sulfonic acid (4-ethylphenyl)isobutylamide (27 mg; 95%) is obtained in the form of a white solid.

¹H NMR (DMSO-d6) δ: 0.83 (d, J=6.7 Hz, 6H), 1.19 (t, J=7.6 Hz, 3H), 1.22-1.26 (m, 1H), 1.33-1.47 (m, 1H), 1.59-2.06 (m, 5H), 2.61 (q, J=7.6 Hz, 2H), 2.91-3.10 (m, 2H), 3.12-3.68 (m, 7H), 3.95-4.15 (m, 1H), 4.44-4.54 (m, 1H), 5.13-5.60 (m, 1H), 6.82-6.92 (m, 1H), 7.00 (d, J=8.1 Hz, 2H), 7.05-7.14 (m, 1H), 7.18 (d, J=7.8 Hz, 2H), 7.30-7.43 (m, 1H).

MS: [M+H]=472

Example 59

4-hydroxy-1-piperidin-4-ylmethyl-1,2,3,4-tetrahydroquinoline-6-sulfonic Acid (4-ethylphenyl)isobutylamide

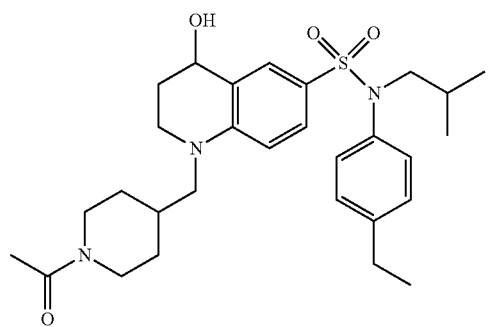

Compound 58

83

1. Synthesis of Intermediate 59.1

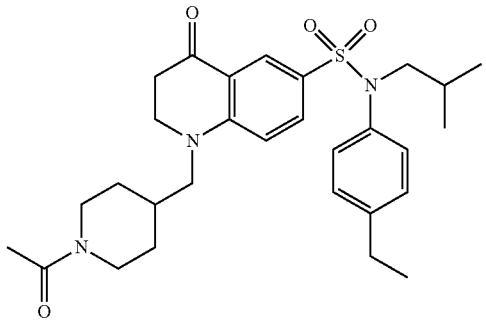 [SMILES: CCc1ccc(N(CC(C)C)S(=O)(=O)c2ccc3c(c2)C(=O)CCN3CC2CCN(C(C)=O)CC2)cc1]

1-(1-acetylpiperidin-4-ylmethyl)-4-oxo-1,2,3,4-tetra-hydroquinoline-6-sulfonic Acid (4-ethylphenyl)isobutylamide A mixture of 4-oxo-1-piperidin-4-ylmethyl-1,2,3,4-tetra-hydroquinoline-6-sulfonic acid (4-ethylphenyl)isobutylamide (40 mg; 0.08 mmol) in dichloromethane (1.5 ml), acetyl chloride (20 µl; 0.28 mmol) and trimethylamine (20.00 µl; 0.14 mmol) is stirred for 16 hours and concentrated under nitrogen. The residue is taken up in N,N'-dimethylformamide and filtered. The filtrate is purified by preparative HPLC (C18 column, eluent: acetonitrile in water/0.1% of formic acid).

The 1-(1-acetylpiperidin-4-ylmethyl)-4-oxo-1,2,3,4-tetra-hydroquinoline-6-sulfonic acid (4-ethylphenyl)isobutylamide (33 mg; 76%) is obtained in the form of a yellow solid with a compliant $^1$H NMR.

MS: [M+H]=526

2. Synthesis of 4-hydroxy-1-piperidin-4-ylmethyl-1,2,3,4-tetrahydroquinoline-6-sulfonic Acid (4-ethylphenyl)isobutylamide With the same procedure as for example 2, 1-(1-acetylpiperidin-4-ylmethyl)-4-hydroxy-1,2,3,4-tetrahydroquinoline-6-sulfonic acid (4-ethylphenyl)isobutylamide (27 mg; 86%) is obtained in the form of a white solid.

1H NMR (DMSO-d6) δ: 0.83 (dd, J=6.6, 2.7 Hz, 6H), 0.98-1.11 (m, 1H), 1.18 (t, J=7.6 Hz, 3H), 1.34-1.46 (m, 1H), 1.66 (t, J=14.9 Hz, 2H), 1.74-1.86 (m, 3H), 1.89-2.05 (m, 4H), 2.39-2.48 (m, 1H), 2.60 (q, J=7.6 Hz, 2H), 2.96 (t, J=12.7 Hz, 1H), 3.13-3.37 (m, 4H), 3.39-3.49 (m, 1H), 3.57-3.65 (m, 1H), 3.82 (d, J=13.5 Hz, 1H), 4.40 (d, J=13.0 Hz, 1H), 4.51 (q, J=4.9 Hz, 1H), 5.32 (d, J=4.9 Hz, 1H), 6.67 (d, J=9.0 Hz, 1H), 6.99 (d, J=8.3 Hz, 2H), 7.09 (dd, J=8.9, 2.4 Hz, 1H), 7.18 (d, J=8.3 Hz, 2H), 7.32 (d, J=2.4 Hz, 1H).

MS: [M+H]=528

84

Example 60

Synthesis of 4-hydroxy-1-piperidin-4-ylmethyl-1,2,3,4-tetrahydroquinoline-6-sulfonic Acid (4-ethylphenyl)isobutylamide

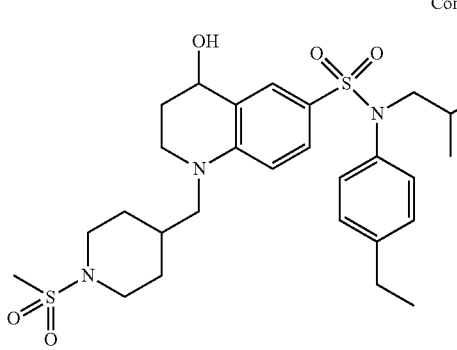

Compound 59

1. Synthesis of Intermediate 60.1

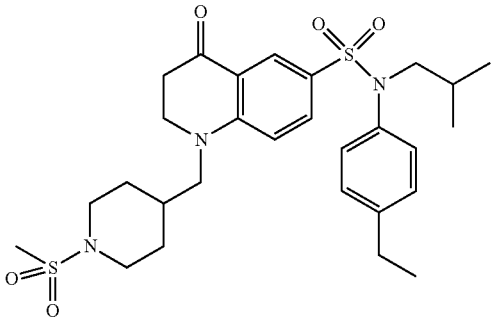 [SMILES: CCc1ccc(N(CC(C)C)S(=O)(=O)c2ccc3c(c2)C(=O)CCN3CC2CCN(S(C)(=O)=O)CC2)cc1]

1-(1-acetylpiperidin-4-ylmethyl)-4-oxo-1,2,3,4-tetra-hydroquinoline-6-sulfonic Acid (4-ethylphenyl)isobutylamide With the same procedure as for intermediate 59.1, 1-(1-methanesulfonylpiperidin-4-ylmethyl)-4-oxo-1,2,3,4-tetra-hydroquinoline-6-sulfonic acid (4-ethylphenyl)isobutylamide (6 mg; 13%) is obtained in the form of a beige-colored solid with a compliant $^1$H NMR.

MS: [M+H]=562

2. Synthesis of 4-hydroxy-1-piperidin-4-ylmethyl-1,2,3,4-tetrahydroquinoline-6-sulfonic Acid (4-ethylphenyl)isobutylamide

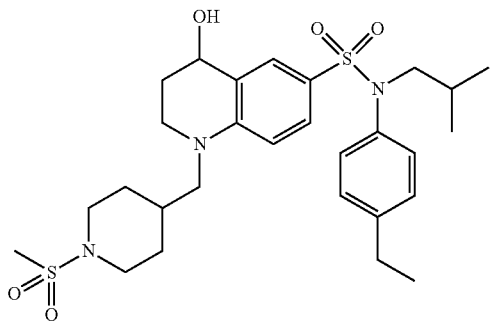 [SMILES: CCc1ccc(N(CC(C)C)S(=O)(=O)c2ccc3c(c2)C(O)CCN3CC2CCN(S(C)(=O)=O)CC2)cc1]

With the same procedure as for example 2, 4-hydroxy-1-(1-methanesulfonylpiperidin-4-ylmethyl)-1,2,3,4-tetrahydroquinoline-6-sulfonic acid (4-ethylphenyl)isobutylamide (2.1 mg; 34%) is obtained in the form of a white solid.

1H NMR (DMSO-d6) δ: 0.83 (dd, J=6.6, 2.6 Hz, 6H), 1.18 (t, J=7.6 Hz, 3H), 1.22-1.36 (m, 2H), 1.36-1.47 (m, 1H), 1.68-1.90 (m, 5H), 2.57-2.66 (m, 4H), 2.84 (s, 3H), 3.16-3.29 (m, 4H), 3.29-3.37 (m, 1H), 3.40-3.49 (m, 1H), 3.57 (d, J=11.7 Hz, 2H), 4.51 (q, J=4.9 Hz, 1H), 5.32 (d, J=4.9 Hz, 1H), 6.68 (d, J=9.0 Hz, 1H), 6.97-7.02 (m, 2H), 7.09 (dd, J=8.9, 2.4 Hz, 1H), 7.17 (d, J=8.4 Hz, 2H), 7.32 (d, J=2.2 Hz, 1H).

MS: [M+H]=564

Example 61

Synthesis of 1-(1-acetylpiperidin-4-yl)-4-oxo-1,2,3,4-tetrahydroquinoline-6-sulfonic Acid (4-ethylphenyl)isobutylamide Compound 60

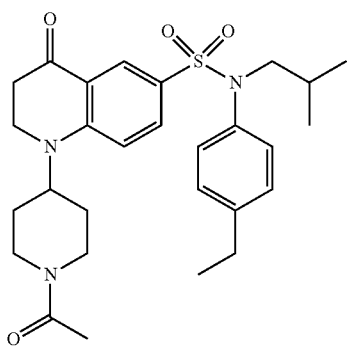

With the same procedure as for intermediate 59.1, 1-(1-acetylpiperidin-4-yl)-4-oxo-1,2,3,4-tetrahydroquinoline-6-sulfonic acid (4-ethylphenyl)isobutylamide (45 mg; 68%) is obtained in the form of a yellow solid.

1H NMR (DMSO-d6) δ: 0.84 (d, J=6.5 Hz, 6H), 1.19 (t, J=7.6 Hz, 3H), 1.34-1.47 (m, 1H), 1.51-1.86 (m, 4H), 2.04 (s, 3H), 2.57-2.72 (m, 5H), 3.15-3.28 (m, 3H), 3.52 (t, J=6.9 Hz, 2H), 3.92 (d, J=13.7 Hz, 1H), 4.15-4.30 (m, 1H), 4.53 (d, J=12.8 Hz, 1H), 7.02 (d, J=8.1 Hz, 2H), 7.20 (d, J=8.0 Hz, 2H), 7.28 (d, J=9.3 Hz, 1H), 7.37 (dd, J=9.3, 2.6 Hz, 1H), 7.82 (d, J=2.6 Hz, 1H)

MS: [M+H]=512

Example 62

Synthesis of 1-(1-acetylpiperidin-4-yl)-4-hydroxy-1,2,3,4-tetrahydroquinoline-6-sulfonic Acid (4-ethylphenyl)isobutylamide Compound 61

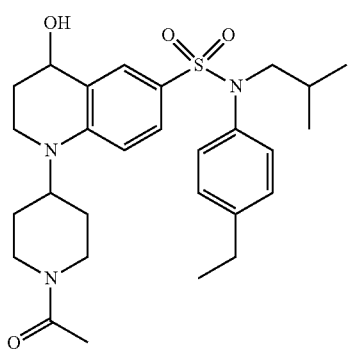

With the same procedure as for example 2, 1-(1-acetylpiperidin-4-yl)-4-hydroxy-1,2,3,4-tetrahydroquinoline-6-sulfonic acid (4-ethylphenyl)isobutylamide (33 mg; 87%) is obtained in the form of a white solid.

$^1$H NMR (DMSO-d6) δ: 0.83 (d, J=6.5 Hz, 6H), 1.19 (t, J=7.6 Hz, 3H), 1.34-1.47 (m, 1H), 1.47-1.86 (m, 6H), 2.03 (s, 3H), 2.56-2.65 (m, 3H), 3.13-3.30 (m, 5H), 3.90 (d, J=13.4 Hz, 1H), 3.96-4.10 (m, 1H), 4.41-4.58 (m, 2H), 5.33 (d, J=4.8 Hz, 1H), 6.87 (d, J=9.0 Hz, 1H), 7.00 (d, J=8.1 Hz, 2H), 7.11 (dd, J=8.8, 2.5 Hz, 1H), 7.18 (d, J=7.9 Hz, 2H), 7.36 (d, J=2.4 Hz, 1H)).

MS: [M+H]=514

Example 63

1-(1-acetylpiperidin-4-yl)-4-oxo-1,2,3,4-tetrahydroquinoline-6-sulfonic Acid (4-ethylphenyl)isobutylamide Compound 63

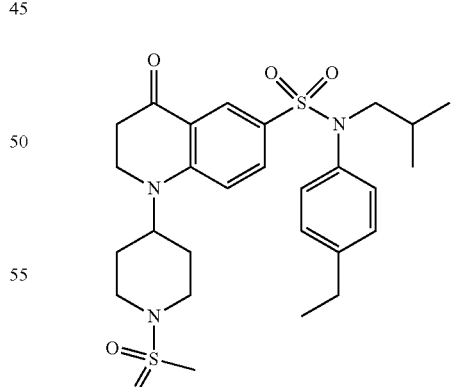

With the same procedure as for intermediate 59.1, 1-(1-methanesulfonylpiperidin-4-yl)-4-oxo-1,2,3,4-tetrahydroquinoline-6-sulfonic acid (4-ethylphenyl)isobutylamide (51 mg; 72%) is obtained in the form of a yellow solid.

1H NMR (DMSO-d6) δ: 0.84 (d, J=6.6 Hz, 6H), 1.18 (t, J=7.6 Hz, 3H), 1.41 (hept, J=6.7 Hz, 1H), 1.74-1.95 (m, 4H), 2.56-2.67 (m, 4H), 2.87-3.03 (m, 5H), 3.23 (d, J=7.3 Hz, 2H), 3.56 (t, J=6.8 Hz, 2H), 3.70 (d, J=11.7 Hz, 2H), 4.05-4.17 (m, 1H), 7.01 (d, J=8.0 Hz, 2H), 7.16-7.26 (m, 3H), 7.37 (dd, J=9.2, 2.6 Hz, 1H), 7.82 (d, J=2.7 Hz, 1H)

MS: [M+H]=548

Example 64

Synthesis of 4-hydroxy-1-(1-methanesulfonylpiperidin-4-yl)-1,2,3,4-tetrahydroquinoline-6-sulfonic Acid (4-ethylphenyl)isobutylamide Compound 64

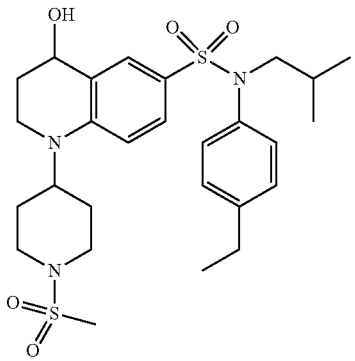

With the same procedure as for example 2, 4-hydroxy-1-(1-methanesulfonylpiperidin-4-ylmethyl)-1,2,3,4-tetrahydroquinoline-6-sulfonic acid (4-ethylphenyl)isobutylamide (2.1 mg; 34%) is obtained in the form of a white solid.

¹H NMR (DMSO-d6) δ: 0.83 (d, J=6.7 Hz, 6H), 1.19 (t, J=7.6 Hz, 3H), 1.32-1.48 (m, 1H), 1.70-1.94 (m, 6H), 2.61 (q, J=7.6 Hz, 2H), 2.87-3.00 (m, 5H), 3.14-3.37 (m, 4H), 3.67 (d, J=11.7 Hz, 2H), 3.86-3.99 (m, 1H), 4.48 (q, J=5.0 Hz, 1H), 5.34 (d, J=4.9 Hz, 1H), 6.82 (d, J=9.3 Hz, 1H), 7.00 (d, J=7.9 Hz, 2H), 7.10 (dd, J=8.8, 2.4 Hz, 1H), 7.18 (d, J=8.0 Hz, 2H), 7.37 (d, J=2.4 Hz, 1H).

MS: [M+H]=550

Example 65

Synthesis of 4-hydroxy-1-(1H-pyrazol-4-ylmethyl)-1,2,3,4-tetrahydroquinoline-6-sulfonic Acid isopropyl(4-methoxy-2-methylphenyl)amide Compound 65

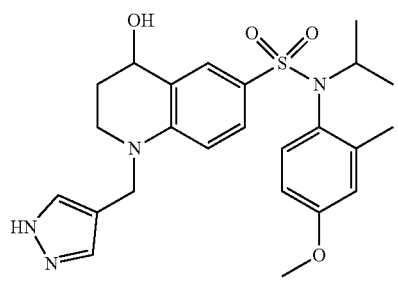

1. Synthesis of Intermediate 65.1

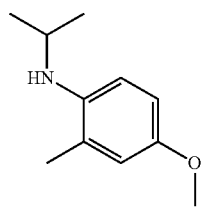

Isopropyl(4-methoxy-2-methylphenyl)amine

Sodium triacetoxyborohydride (4.63 g; 22 mmol) is added to a solution of 4-methoxy-2-methylaniline (2.0 g, 14.6 mmol) in acetone (20 ml). The reaction medium is heated for 10 minutes by microwave irradiation at 70° C. The reaction medium is poured onto ice. The aqueous phase is extracted with dichloromethane. The organic phases are combined, washed with brine, dried (MgSO₄), filtered and evaporated.

The crude product is purified by chromatography on silica gel (eluent: heptane/ethyl acetate, from 0 to 15% of ethyl acetate). The isopropyl(4-methoxy-2-methylphenyl)amine (1.43 g; 55%) is obtained in the form of a yellow oil with a compliant ¹H NMR.

MS: [M+H]=180

2. Synthesis of Intermediate 65.2

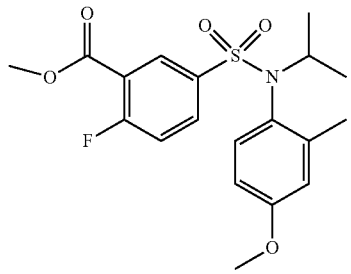 [SMILES: COC(=O)c1cc(S(=O)(=O)N(c2ccc(OC)cc2C)C(C)C)ccc1F]

methyl 2-fluoro-5-[isopropyl(4-methoxy-2-methylphenyl)sulfamoyl]benzoate

Isopropyl(4-methoxy-2-methylphenyl)amine (1.0 g; 5.6 mmol) is added to a solution of methyl 5-chlorosulfonyl-2-fluorobenzoate (1.41; 5.6 mmol) in pyridine (4.0 ml; 0.05 mol), in a sealed tube. The reaction medium is heated for 40 minutes at a temperature of 100° C. under microwave irradiation. The reaction medium is diluted with ethyl acetate.

The organic phase is washed three times with 1N hydrochloric acid solution, then with saturated sodium hydrogen carbonate solution and then with water, dried over magnesium sulfate, filtered and evaporated.

The methyl 2-fluoro-5-[isopropyl(4-methoxy-2-methylphenyl)sulfamoyl]benzoate (1.41 g; 64%) is obtained in the form of a brown oil with a compliant ¹H NMR.

MS: [M−H]=396

3. Synthesis of Intermediate 65.3

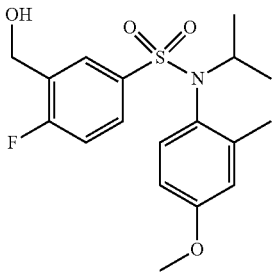 [SMILES: COc1ccc(N(C(C)C)S(=O)(=O)c2ccc(F)c(CO)c2)c(C)c1]

4-fluoro-3-hydroxymethyl-N-isopropyl-N-(4-methoxy-2-methylphenyl)benzenesulfonamide With the same procedure as for intermediate 1.5, 4-fluoro-3-hydroxymethyl-N-isopropyl-N-(4-methoxy-2-methylphenyl)benzenesulfonamide (0.47 g; 99%) is obtained in the form of a yellow oil with a compliant $^1$H NMR.

MS: [M−H]=366

4. Synthesis of Intermediate 65.4

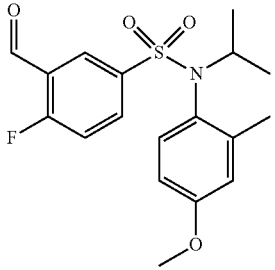 [SMILES: COc1ccc(N(C(C)C)S(=O)(=O)c2ccc(F)c(C=O)c2)c(C)c1]

fluoro-3-formyl-N-isopropyl-N-(4-methoxy-2-methylphenyl)benzenesulfonamide

With the same procedure as for intermediate 1.6, 4-fluoro-3-formyl-N-isopropyl-N-(4-methoxy-2-methylphenyl)benzenesulfonamide (0.42 g; 88%) is obtained in the form of a yellow oil with a compliant $^1$H NMR.

MS: [M−H]=366

5. Synthesis of Intermediate 65.5

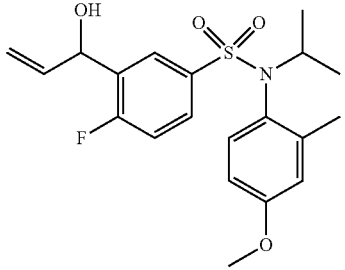 [SMILES: C=CC(O)c1cc(S(=O)(=O)N(c2ccc(OC)cc2C)C(C)C)ccc1F]

4-fluoro-3-(1-hydroxyallyl)-N-isopropyl-N-(4-methoxy-2-methylphenyl)benzenesulfonamide With the same procedure as for intermediate 1.7, 4-fluoro-3-(1-hydroxyallyl)-N-isopropyl-N-(4-methoxy-2-methylphenyl)benzenesulfonamide (0.17 g; 42%) is obtained in the form of a yellow oil with a compliant $^1$H NMR.

MS: [M−H]=394

6. Synthesis of Intermediate 65.6

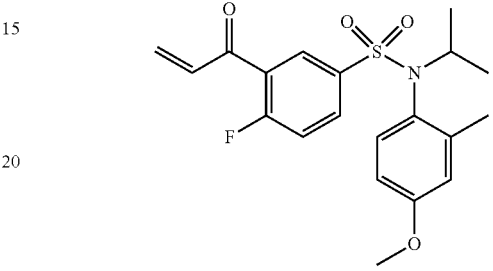

3-acryloyl-4-fluoro-N-isopropyl-N-(4-methoxy-2-methylphenyl)benzenesulfonamide

With the same procedure as for intermediate 1.6, 3-acryloyl-4-fluoro-N-isopropyl-N-(4-methoxy-2-methylphenyl)benzenesulfonamide (0.16 g; 100%) is obtained in the form of a yellow oil with a compliant $^1$H NMR.

MS: [M−H]=392

7. Synthesis of 4-hydroxy-1-(1H-pyrazol-4-ylmethyl)-1,2,3,4-tetrahydroquinoline-6-sulfonic Acid isopropyl(4-methoxy-2-methylphenyl)amide 1H-Pyrazol-4-ylmethanamine dihydrochloride (0.11 g; 0.65 mmol) and triethylamine (270 µl; 1.95 mmol) are added to a solution of 3-acryloyl-4-fluoro-N-isopropyl-N-(4-methoxy-2-methylphenyl)benzenesulfonamide (0.17 g; 0.43 mmol) in N,N-dimethylformamide (850 µl). The reaction medium is stirred for 20 minutes and sodium borohydride (0.11 g; 3 mmol) and methanol (680 µl) are then added.

The reaction medium is stirred for 25 minutes and is then hydrolyzed with aqueous 1M sodium dihydrogen phosphate solution and extracted with dichloromethane. The organic phases are combined, dried over anhydrous sodium sulfate, filtered and concentrated.

The crude product is purified by preparative HPLC (C18 column, eluent: acetonitrile in water/0.1% of formic acid).

The 4-hydroxy-1-(1H-pyrazol-4-ylmethyl)-1,2,3,4-tetrahydroquinoline-6-sulfonic acid isopropyl(4-methoxy-2-methylphenyl)amide (15.00 mg; 7.31%) is obtained in the form of a beige-colored solid.

$^1$H NMR (DMSO-d6) δ: 0.87 (dd, J=6.7, 3.1 Hz, 3H), 0.94 (dd, J=6.7, 2.2 Hz, 3H), 1.15 (s, 2H), 1.79-1.96 (m, 2H), 2.24 (d, J=8.9 Hz, 3H), 3.28-3.53 (m, 2H), 3.76 (s, 3H), 4.23-4.60 (m, 4H), 5.35 (dd, J=5.0, 2.5 Hz, 1H), 6.64-6.78 (m, 2H), 6.84 (d, J=8.9 Hz, 1H), 6.88 (t, J=3.2 Hz, 1H), 7.27 (ddd, J=8.2, 5.3, 2.4 Hz, 1H), 7.38-7.77 (m, 1H), 12.71 (s, 1H)

MS: [M−H]=471

Example 66

4-hydroxy-1-(tetrahydropyran-4-ylmethyl)-1,2,3,4-tetrahydroquinoline-6-sulfonic Acid (4,6-dimethyl-pyridin-3-yl)isobutylamide Compound 66

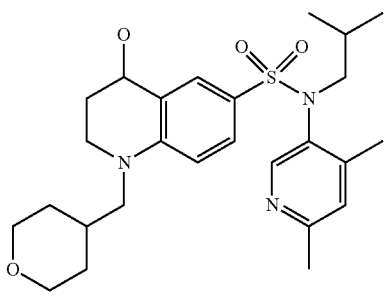

1. Synthesis of Intermediate 66.1

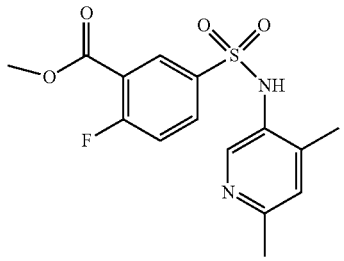

methyl 5-(4,6-dimethylpyridin-3-ylsulfamoyl)-2-fluorobenzoate

With the same procedure as for intermediate 65.2, methyl 5-(4,6-dimethylpyridin-3-ylsulfamoyl)-2-fluorobenzoate (1.40 g; 78%) is obtained in the form of a white solid with a compliant $^1$H NMR.

MS: [M+H]=339

2. Synthesis of Intermediate 66.2

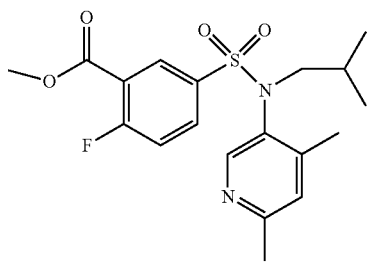 [SMILES: COC(=O)c1cc(S(=O)(=O)N(CC(C)C)c2cnc(C)cc2C)ccc1F]

methyl 5-[(4,6-dimethylpyridin-3-yl)isobutylsulfamoyl]-2-fluorobenzoate

1-Iodo-2-methylpropane (1.30 ml; 11.3 mmol) is added to a mixture of methyl 5-(4,6-dimethylpyridin-3-ylsulfamoyl)-2-fluorobenzoate (1.24 mg; 3.7 mmol) and cesium carbonate (1.79 mg; 5.5 mmol) in 1-methyl-2-pyrrolidone (12 ml).

The reaction medium is heated for 1 hour at a temperature of 100° C. and hydrolyzed with water.

The organic phase is separated out, dried (MgSO$_4$), filtered and concentrated. The crude product is chromatographed on silica gel (eluent: heptane/ethyl acetate, from 40 to 80% of ethyl acetate). The methyl 5-[(4,6-dimethylpyridin-3-yl)isobutylsulfamoyl]-2-fluorobenzoate (1.15 g; 80%) is obtained in the form of an orange oil with a compliant $^1$H NMR.

MS: [M+H]=395

3. Synthesis of Intermediate 66.3

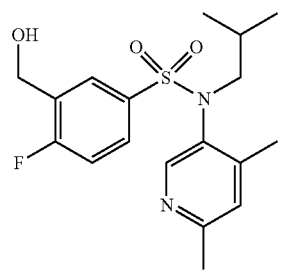 [SMILES: Cc1cc(C)c(N(CC(C)C)S(=O)(=O)c2ccc(F)c(CO)c2)cn1]

N-(4,6-dimethylpyridin-3-yl)-4-fluoro-3-hydroxymethyl-N-isobutylbenzenesulfonamide With the same procedure as for intermediate 1.5, N-(4,6-dimethylpyridin-3-yl)-4-fluoro-3-hydroxymethyl-N-isobutylbenzenesulfonamide (0.65 g; 100%) is obtained in the form of a yellow oil with a compliant $^1$H NMR.

MS: [M+H]=367

4. Synthesis of Intermediate 66.4

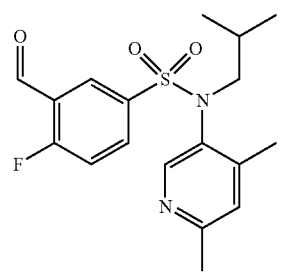 [SMILES: Cc1cc(C)c(N(CC(C)C)S(=O)(=O)c2ccc(F)c(C=O)c2)cn1]

N-(4,6-Dimethylpyridin-3-yl)-4-fluoro-3-formyl-N-isobutylbenzenesulfonamide

With the same procedure as for intermediate 1.6, N-(4,6-dimethylpyridin-3-yl)-4-fluoro-3-formyl-N-isobutylbenzenesulfonamide (0.43 g; 67%) is obtained in the form of a colorless oil with a compliant $^1$H NMR.

MS: [M+H]=365

5. Synthesis of Intermediate 66.5

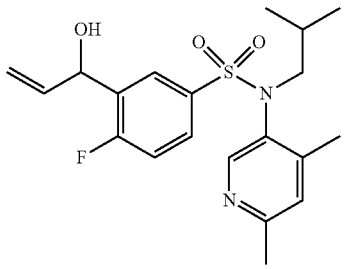 [SMILES: C=CC(O)c1cc(S(=O)(=O)N(CC(C)C)c2cnc(C)cc2C)ccc1F]

N-(4,6-dimethylpyridin-3-yl)-4-fluoro-3-(1-hydroxyallyl)-N-isobutylbenzenesulfonamide With the same procedure as for intermediate 1.7, N-(4,6-dimethylpyridin-3-yl)-4-fluoro-3-(1-hydroxyallyl)-N-isobutylbenzenesulfonamide (0.28 g; 60%) is obtained in the form of a colorless oil with a compliant $^1$H NMR.
MS: [M+H]=393

6. Synthesis of Intermediate 66.6

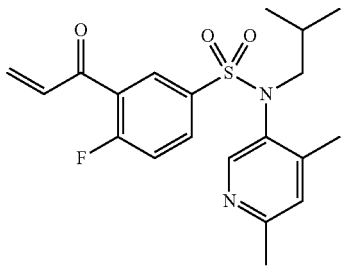 [SMILES: C=CC(=O)c1cc(S(=O)(=O)N(CC(C)C)c2cnc(C)cc2C)ccc1F]

3-acryloyl-N-(4,6-dimethylpyridin-3-yl)-4-fluoro-N-isobutylbenzenesulfonamide

With the same procedure as for intermediate 1.6, 3-acryloyl-N-(4,6-dimethylpyridin-3-yl)-4-fluoro-N-isobutylbenzenesulfonamide (0.08 g; 29%) is obtained in the form of a yellow oil with a compliant $^1$H NMR.
MS: [M+H]=391

7. Synthesis of 4-hydroxy-1-(tetrahydropyran-4-ylmethyl)-1,2,3,4-tetrahydroquinoline-6-sulfonic Acid (4,6-dimethylpyridin-3-yl)isobutylamide With the same procedure as for example 65, 4-hydroxy-1-(tetrahydropyran-4-ylmethyl)-1,2,3,4-tetrahydroquinoline-6-sulfonic acid (4,6-dimethylpyridin-3-yl)isobutylamide (16 mg; 16%) is obtained in the form of an off-white solid.

$^1$H NMR (DMSO-d6, 80° C.) δ: 0.74-0.99 (m, 6H), 1.23-1.40 (m, 2H), 1.46-1.55 (m, 1H), 1.55-1.65 (m, 2H), 1.80-1.93 (m, 2H), 1.95-2.09 (m, 1H), 2.23 (s, 3H), 2.42 (s, 3H), 3.20-3.41 (m, 7H), 3.43-3.52 (m, 1H), 3.82-3.92 (m, 2H), 4.52-4.59 (m, 1H), 5.10 (d, J=4.9 Hz, 1H), 6.71 (d, J=8.9 Hz, 1H), 7.14 (s, 1H), 7.21 (d, J=8.8 Hz, 1H), 7.44 (s, 1H), 7.78-7.93 (m, 1H)
MS: [M+H]=488

The invention claimed is:

1. A compound of formula (V), or pharmaceutically acceptable addition salt thereof, hydrate thereof, solvate thereof, and/or a mixture thereof:

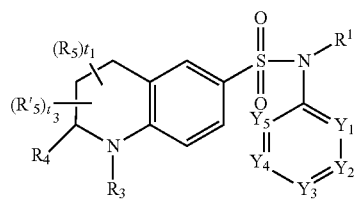

in which formula (I):
one or two of the elements $Y^1$, $Y^2$, $Y^3$, $Y^4$ and $Y^5$ represent(s) a nitrogen and the other elements correspond to a group —$CR^2$, or each of the elements $Y^1$, $Y^2$, $Y^3$, $Y^4$ and $Y^5$ corresponds to —$CR^2$, $R^1$ represents a $C_3$-$C_5$ alkyl, a $C_3$-$C_5$ cycloalkyl, a $C_2$-$C_5$ alkenyl, a $CH_2$—($C_3$-$C_5$)cycloalkyl, a $C_4$-$C_5$ heterocycloalkyl, or a $CH_2$—($C_4$-$C_6$)heterocycloalkyl, $R^2$ represents a hydrogen or a halogen, a $C_1$-$C_5$ alkyl, a $C_2$-$C_4$ alkenyl, a $C_1$-$C_4$ alkoxy, —CN, a —C(=O)$R'^2$ with $R'^2$ denoting a $C_1$-$C_3$ alkoxy, a —$CF_3$; said alkyl, alkenyl and alkoxy optionally being substituted with one or more halogens, $t_1$ and $t_3$, which may be identical or different, denote a natural integer 0 or 1, $R^3$ and $R^4$, which are identical or different, represent a hydrogen or $(CHR^6)_n$—$(Z)_o$—$(CHR'^6)_p$—$R^7$, n, o and p, which may be identical or different, represent zero or a natural integer ranging from 1 to 3, when $R^3$ represents $(CHR^6)_n$—$(Z)_o$—$(CHR'^6)_p$—$R^7$, then $R^4$ represents a hydrogen, when $R^4$ represents $(CHR^6)_n$—$(Z)_o$—$(CHR'^6)_p$—$R^7$, then $R^3$ represents a hydrogen, Z represents a divalent group selected from the group consisting of —$CH_2$—, —NH—, and —O—, $R^6$ and $R'^6$, which are identical or different, represent a hydrogen,—$CH_3$, —OH, a $C_1$ hydroxyalkyl group, or —COOH, $R^7$ represents:
  a hydrogen or a halogen,
  a COO$R'^7$ with $R'^7$ denoting ($C_1$)alkyl($C_6$)heterocycle,
  a non-cationic heterocyclic optionally substituted with one or more halogens, one or more $C_1$-$C_3$ alkyl, one or more —OH, one or more carbonyl, one or more $C_1$-$C_4$ hydroxyalkyl, one or more amino, one or more —C(=O)$R^{7a}$, one or more —S(=O)$_2R^{7a}$; $R^{7a}$ representing a $C_1$-$C_3$ alkyl, a $C_1$-$C_3$ alkoxy, or N($R^{8a}$)($R^{8b}$),
  a non-cationic $C_3$-$C_6$ cycloalkyl optionally substituted with one or more methyl, one or more halogen, a —CN or —COR$^{13}$; $R^{13}$ denoting a $C_1$-$C_3$ alkoxy or hydroxyl,
  an aromatic or heteroaromatic, non-cationic radical optionally substituted with one or more halogens, one or more $C_1$-$C_3$ alkyl optionally substituted with one or more halogens, one or more $C_1$-$C_3$ alkoxy, one or more —NR$^{11}$R$^{12}$, one or more —COR$^{11}$, one or more —COOR$^{11}$, one or more —CONR$^{11}$R$^{12}$, one or more —SOR$^{11}$, one or more —SO$_2$R$^{11}$, one or more —NHCOR$^{11}$, one or more —NHCOOR$^{11}$, one or more —SO$_2$NR$^{11}$R$^{12}$ or one or more —CN; R$^{11}$ and R$^{12}$, which are identical or different, representing a hydrogen, a —OH, a C$_1$-C$_3$ alkyl optionally substituted with one or more halogens;

R$^5$ represents a hydrogen or a halogen, a C$_1$-C$_3$ alkyl optionally substituted with one or more halogens, a —NH$_2$, a —CH$_2$R'$^{7a}$ with R'$^{7a}$ denoting a methoxy, a —OH, a —CH$_2$COOH, a —CH(R$^{5b}$)OH, a —COOH, a —CN, or a thioxo, and R'$_5$ represents a carbonyl (C=O) or a thioxo (C=S), R$^{8a}$ and R$^{8b}$, which may be identical or different, denote a hydrogen, a C$_1$-C$_3$ alkyl or a cyclopropyl.

2. The compound of formula (V), or pharmaceutically acceptable addition salt thereof, hydrate thereof, solvate thereof, and/or a mixture thereof, as defined by claim 1, wherein R$^7$ represents a heterocyclic radical selected from the group consisting of:

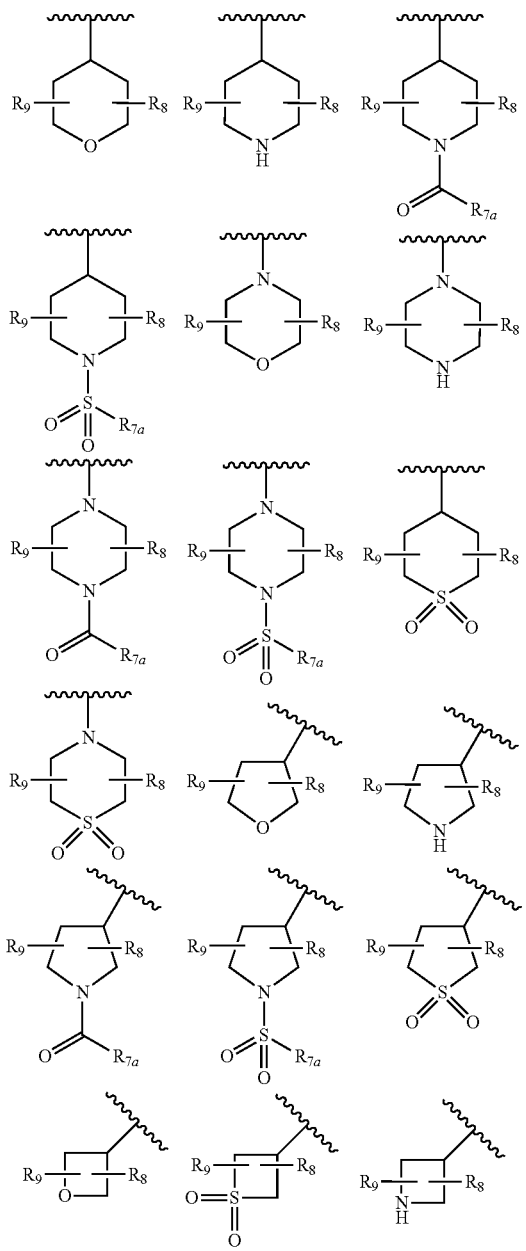

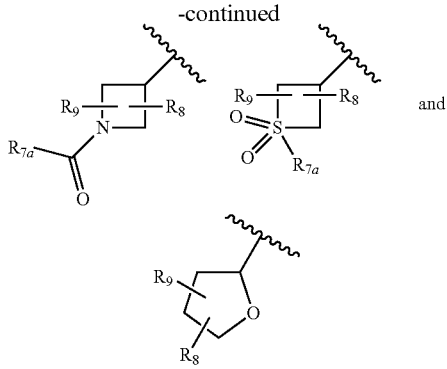

in which:
R$_{7a}$ represents a C$_1$-C$_3$ alkyl, a C$_1$-C$_3$ alkoxy or —N(R$^{8a}$)(R$^{8b}$),
R$^{8a}$ and R$^{8b}$, which are identical or different, denote a hydrogen, a C$_1$-C$_3$ alkyl or a cyclopropyl,
R$_8$ and R$_9$, which are identical or different, represent a hydrogen, a C$_1$-C$_3$ alkyl, a —OH, a carbonyl, a —CH$_2$OH or a —NH$_2$,
R$_8$ and R$_9$ can form, together with the carbons to which they are attached, a 5- to 7-membered carbocyclic ring.

3. The compound of formula (V), or pharmaceutically acceptable addition salt thereof, hydrate thereof, solvate thereof, and/or a mixture thereof, as defined by claim 1, wherein R$^7$ represents an aromatic or heteroaromatic radical selected from the group consisting of:

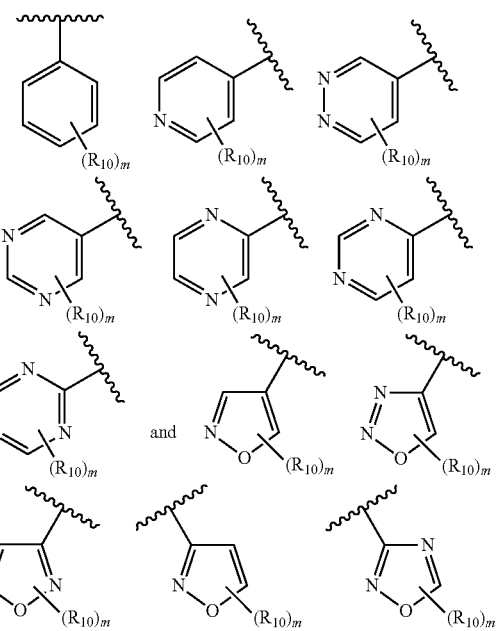

in which:
R$_{10}$ represents a hydrogen or a halogen, a C$_1$-C$_3$ alkyl optionally substituted with one or more halogens, a C$_1$-C$_3$ alkoxy, a —NR$^{11}$R$^{12}$, a —COR$^{11}$, a —COOR$^{11}$, a —CONR$^{11}$R$^{12}$, a —SOR$^{11}$, a —SO$_2$R$^{11}$, a —NHCOR$^{11}$, a —NHCOOR$^{11}$, a —SO$_2$NR$^{11}$R$^{12}$ or a —CN; R$^{11}$ and R$^{12}$, which are identical or different, representing a hydrogen or a C$_1$-C$_3$ alkyl optionally substituted with one or more halogens, and m denotes zero or a natural integer ranging from 1 to 3.

4. The compound of formula (V) as defined by claim 1, or pharmaceutically acceptable addition salt thereof, hydrate thereof, solvate thereof, and/or a mixture thereof, wherein when $t_1$ is equal to zero, then $t_3$ is equal to 1, and, when $t_1$ is equal to 1, then $t_3$ denotes zero.

5. The compound of formula (V) as claimed in any one of claims 1, or pharmaceutically acceptable addition salt thereof, hydrate thereof, solvate thereof, and/or a mixture thereof, wherein $R^{'5}$ denotes a C=O.

6. The compound of formula (V), or pharmaceutically acceptable addition salt thereof, hydrate thereof, solvate thereof, and/or a mixture thereof, as define by claim 1, wherein $R^5$ represents —OH.

7. The compound of formula (V) as defined by claim 1, wherein the compound has the structure of formula (V') or pharmaceutically acceptable addition salt thereof, hydrate thereof, solvate thereof, and/or a mixture thereof:

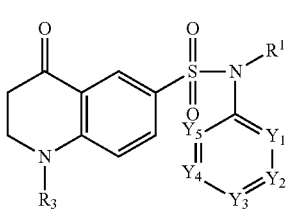

(V')

in which formula (V'), $R^1$, $R^3$, and $Y^1$ to $Y^5$, have the same meanings as in formula (V).

8. The compound of formula (V) as defined by claim 1, wherein the compound has the structure of formula (V''), or pharmaceutically acceptable addition salt thereof, hydrate thereof, solvate thereof, and/or mixture thereof:

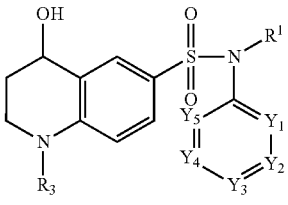

(V'')

in which formula (V'') $R^1$, $R^3$ and $Y^1$ to $Y^5$ have the same meanings as in formula (V).

9. A compound, or pharmaceutically acceptable addition salt thereof, hydrate thereof, solvate thereof, and/or a mixture thereof, selected from the group consisting of:

compound 1

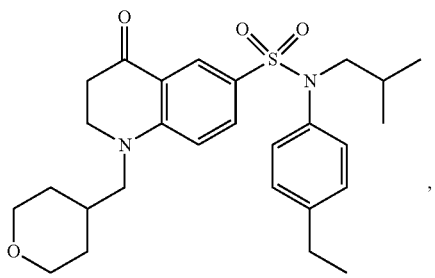

4-oxo-1-(tetrahydropyran-4-ylmethyl)-1,2,3,4-tetrahydroquinoline-6-sulfonic acid (4-ethylphenyl)isobutylamide compound 2

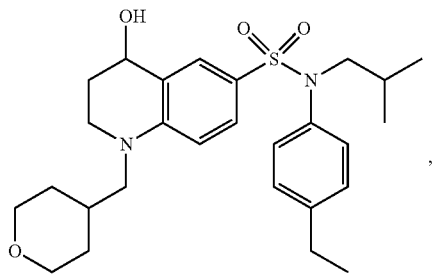

4-hydroxy-1-(tetrahydropyran-4-ylmethyl)-1,2,3,4-tetrahydroquinoline-6-sulfonic acid (4-ethylphenyl)isobutylamide compound 3

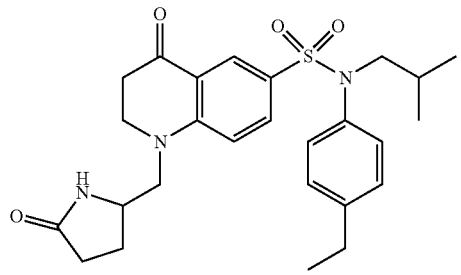

4-oxo-1-(5-oxopyrrolidin-2-ylmethyl)-1,2,3,4-tetrahydroquinoline-6-sulfonic acid (4-ethylphenyl)isobutylamide compound 4

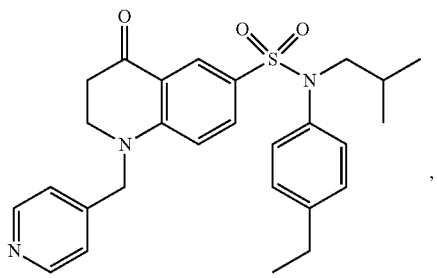

4-oxo-1-pyridin-4-ylmethyl)-1,2,3,4-tetrahydroquinoline-6-sulfonic acid (4-ethylphenyl)isobutylamide compound 6

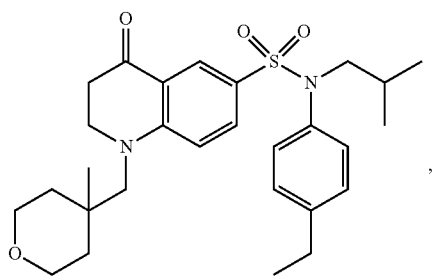

1-(4-methyltetrahydropyran-4-ylmethyl)-4-oxo-1,2,3,4-tetrahydroquinoline-6-sulfonic acid (4-ethylphenyl)isobutylamide -continued compound 7

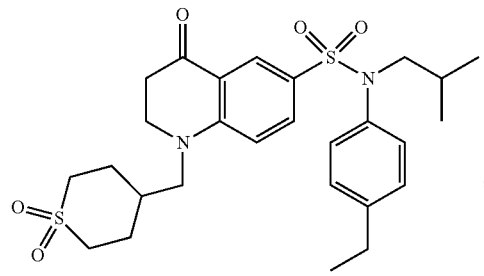

1-(1,1-dioxohexahydro-1λ⁶-thiopyran-4-ylmethyl)-4-oxo-1,2,3,4-tetrahydroquinoline-6-sulfonic acid (4-ethylphenyl)isobutylamide compound 8

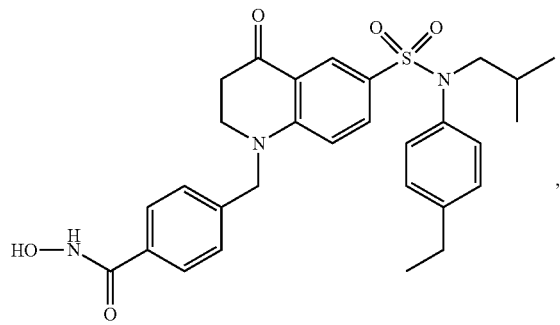

4-{6-[(4-ethylphenyl)isobutylsulfamoyl]-4-oxo-3,4-dihydro-2H-quinolin-1-ylmethyl}-N-hydroxybenazmide compound 9

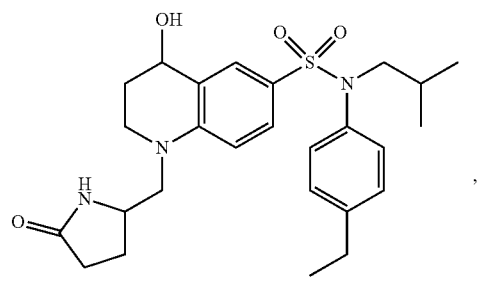

4-hydroxy-1-(5-oxopyrrolidin-2-ylmethyl)-1,2,3,4-tetrahydroquinoline-6-sulfonic acid (4-ethylphenyl)isobutylamide compound 10

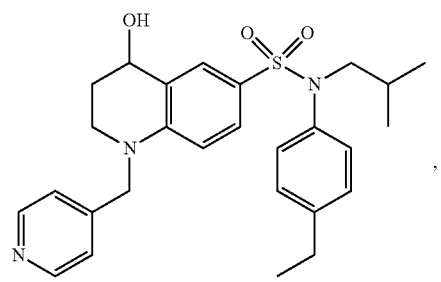

4-hydroxy-1-pyridin-4-ylmethyl)-1,2,3,4-tetrahydroquinoline-6-sulfonic acid (4-ethylphenyl)isobutylamide compound 11

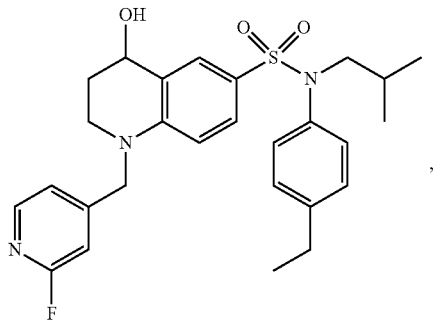

1-(2-fluoropyridin-4-ylmethyl)-4-hydroxy-1,2,3,4-tetrahydroquinoline-6-sulfonic acid (4-ethylphenyl)isobutylamide compound 14

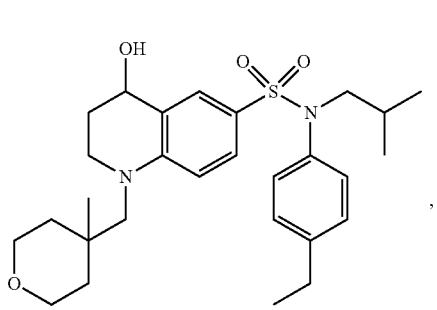

1-(4-methyltetrahydropyran-4-ylmethyl)-4-hydroxy-1,2,3,4-tetrahydroquinoline-6-sulfonic acid (4-ethylphenyl)isobutylamide compound 15

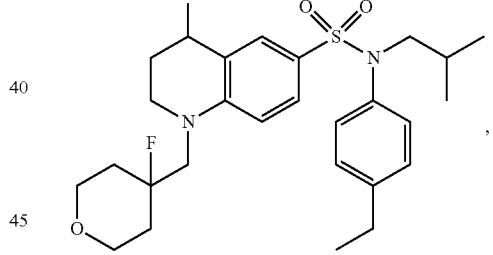

1-(4-fluorotetrahydropyran-4-ylmethyl)-4-hydroxy-1,2,3,4-tetrahydroquinoline-6-sulfonic acid (4-ethylphenyl)isobutylamide compound 16

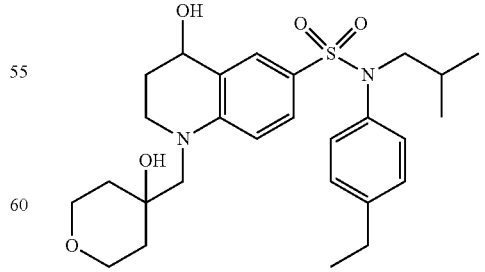

4-hydroxy-1-(4-hydroxytetrahydropyran-4-ylmethyl)-1,2,3,4-tetrahydroquinoline-6-sulfonic acid (4-ethylphenyl)isobutylamide -continued compound 17

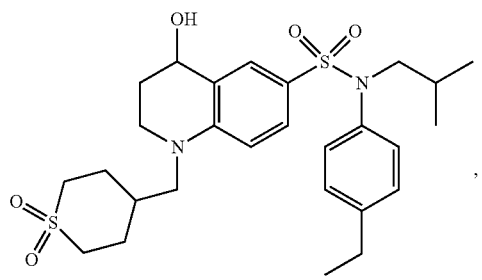

1-(1,1-dioxohexahydro-1λ⁶-thiopyran-
4-ylmethyl)-4-hydroxy-1,2,3,4-
tetrahydroquinoline-6-sulfonic acid (4-ethylphenyl)isobutylamide compound 18

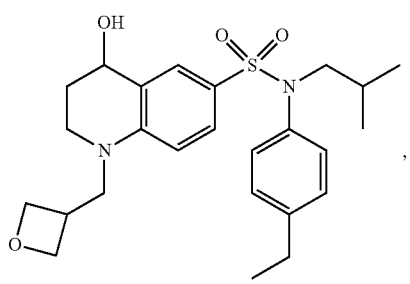

4-hydroxy-1-oxetan-3-ylmethyl-
1,2,3,4-tetrahydroquinoline-6-sulfonic
acid (4-ethylphenyl)isobutylamide compound 19

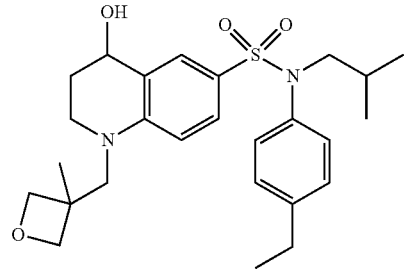

4-hydroxy-1-(3-methyloxetan-3-
ylmethyl-1,2,3,4-tetrahydroquinoline-
6-sulfonicacid (4-
ethylphenyl)isobutylamide compound 20

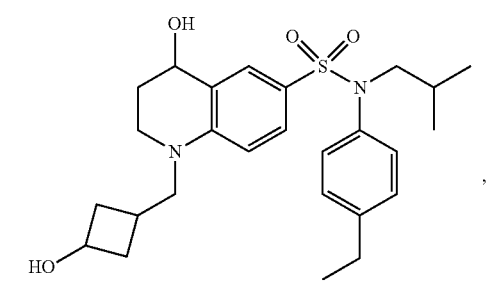

4-hydroxy-1-(3-
hydroxycyclobutylmethyl)-1,2,3,4-tetrahydroquinoline-
6-sulfonic acid (4-
ethylphenyl)isobutylamide
mixture of diastereoisomers:

compound 21

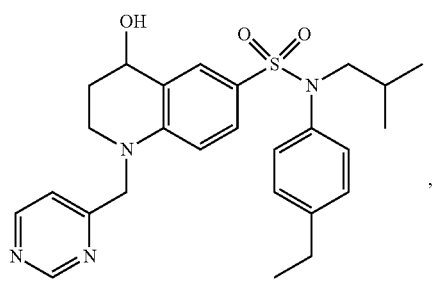

4-hydroxy-1-pyrimidin-4-ylmethyl-
1,2,3,4-tetrahydroquinoline-6-sulfonic
acid (4-ethylphenyl)isobutylamide compound 22

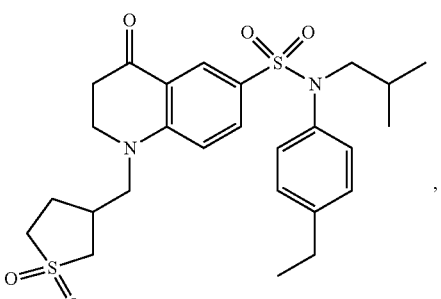

1-(1,1-dioxotetrahydro-1λ⁶-thiophen-
3-ylmethyl)-4-hydroxy-1,2,3,4-
tetrahydroquinoline-6-sulfonic acid (4-
ethylphenyl)isobutylamide compound 23

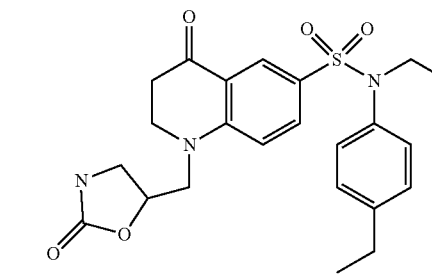

4-hydroxy-1-(2-oxooxazolidin-5-
ylmethyl)-1,2,3,4-tetrahydroquinoline-
6-sulfonic acid (4-
ethylphenyl)isobutylamide compound 24

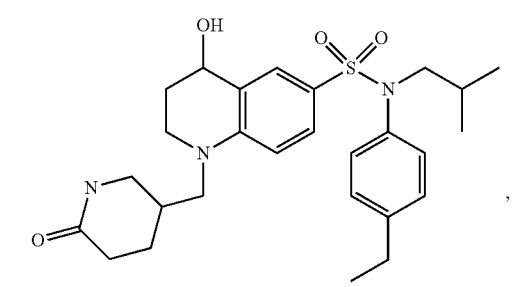

4-hydroxy-1-(5-oxopiperidin-3-
ylmethyl)-1,2,3,4-tetrahydroquinoline-
6-sulfonic acid (4-
ethylphenyl)isobutylamide compound 25

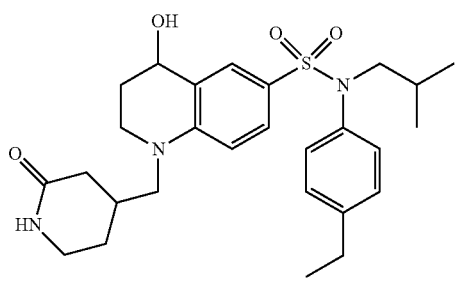

4-hydroxy-1-(2-oxopiperidin-4-ylmethyl)-1,2,3,4-tetrahydroquinoline-6-sulfonic acid (4-ethylphenyl)isobutylamide compound 26

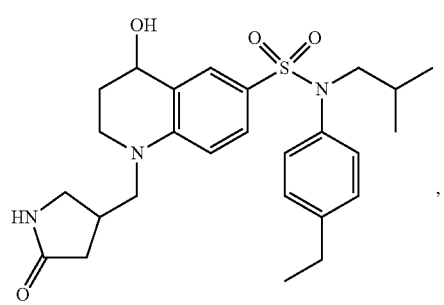

4-hydroxy-1-(5-oxopyrrolidin-3-ylmethyl)-1,2,3,4-tetrahydroquinoline-6-sulfonic acid (4-ethylphenyl)isobutylamide compound 27

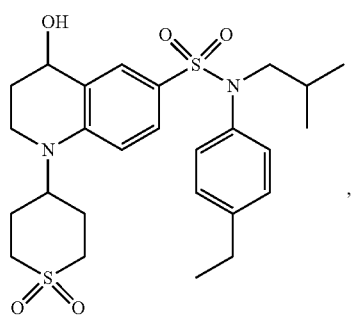

1-(1,1-dioxohexahydro-1$\lambda^6$-thiopyran-4-yl)-4-hydroxy-1,2,3,4-tetrahydroquinoline-6-sulfonic acid (4-ethylphenyl)isobutylamide compound 28

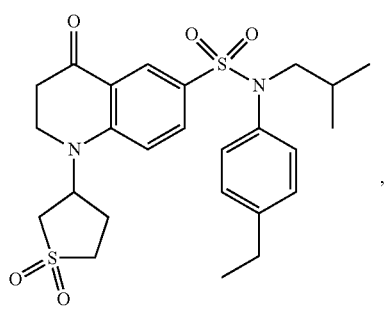

1-(1,1-dioxotetrahydro-1$\lambda^6$-thiophen-3-yl)-4-hydroxy-1,2,3,4-tetrahydroquinoline-6-sulfonic acid (4-ethylphenyl)isobutylamide compound 29

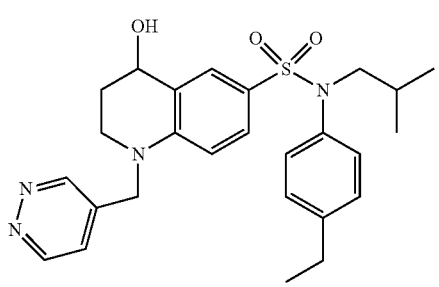

4-hydroxy-1-pyridazin-4-ylmethyl-1,2,3,4-tetrahydroquinoline-6-sulfonic acid (4 ethylpheny)isobutylamide compound 30

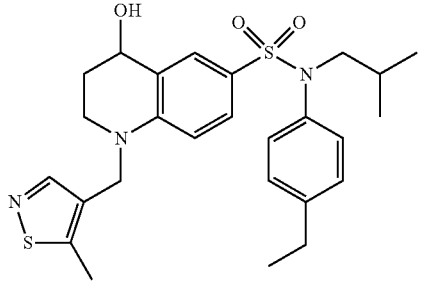

4-hydroxy-1-(5-methylisoxazol-4-ylmethyl)-1,2,3,4-tetrahydroquinoline-6-sulfonic acid (4-ethylphenyl)isobutylamide compound 31

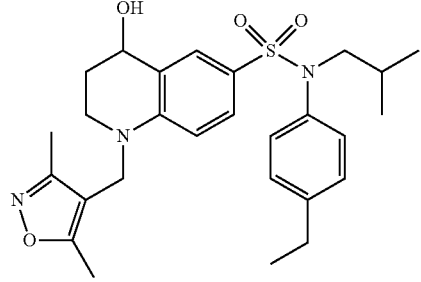

1-(3,5-dimethylisoxazol-4-ylmethyl)-4-hydroxy-1,2,3,4-tetrahydroquinoline-6-sulfonic acid (4-ethylphenyl)isobutylamide compound 32

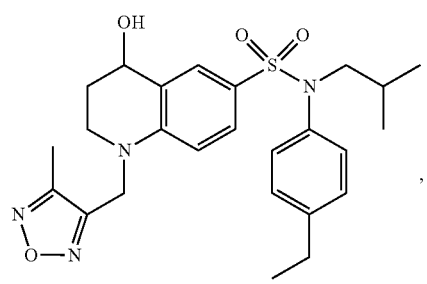

4-hydroxy-1-(4-methylfurazan-3-ylmethyl)-1,2,3,4-tetrahydroquinoline-6-sulfonic acid (4-ethylphenyl)isobutylamide compound 33

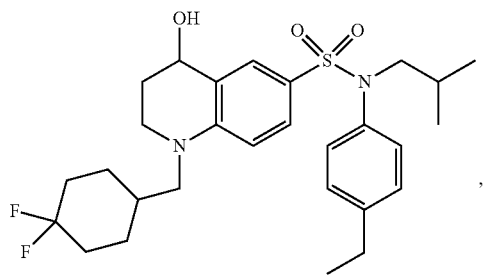

1-(4,4-difluorocyclohexylmethyl)-4-
hydroxy-1,2,3,4-tetrahydroquinoline-
6-sulfonic acid (4-
ethylphenyl)isobutylamide compound 34

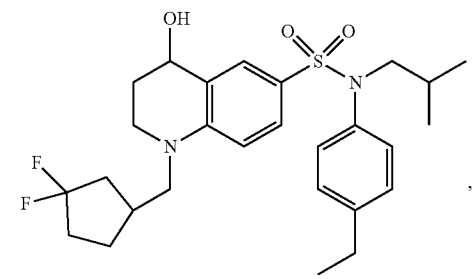

1-(3,3-difluorocyclopentylmethyl)-4-
hydroxy-1,2,3,4-tetrahydroquinoline-
6-sulfonic acid (4-
ethylphenyl)isobutylamide compound 35

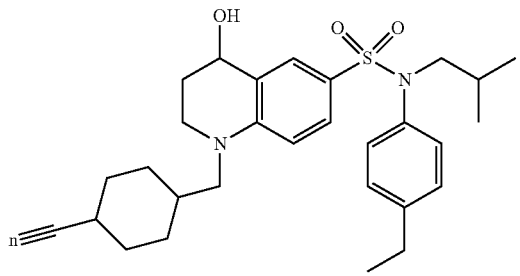

1-4-cyanocyclohexylmethyl)-4-
hydroxy-1,2,3,4-tetrahydroquinoline-
6-sulfonic acid (4-
ethylphenyl)isobutylamide compound 36

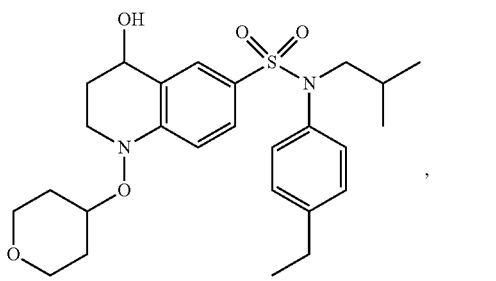

4-hydroxy-(tetrahydropyran-4-
yloxy)-1,2,3,4-tetrahydroquinoline-6-
sulfonic acid (4-
ethylphenyl)isobutylamide compound 37

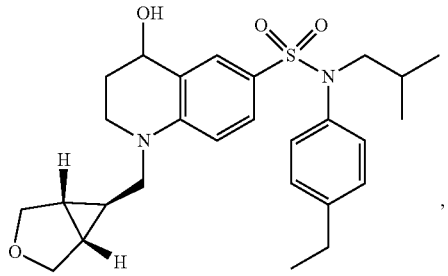

4-hydroxy-1-[(1S,5R,6S)-1-(3-
oxabicyclo[3.1.0]hex-6-yl)methyl]-
1,2,3,4-tetrahydroquinoline-6-sulfonic
acid (4-ethylphenyl)isobutylamide compound 38

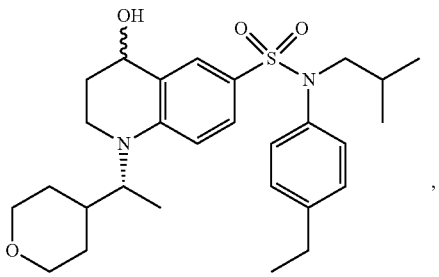

4-hydroxy-1-[(R)-1-(tetrahydropyran-
4-yl)ethyl]-1,2,3,4-
tetrahydroquinoline-6-sulfonic acid (4-
ethylphenyl)isobutylamide compound 39

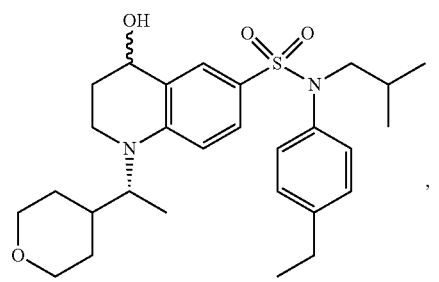

4-hydroxy-1-[(R)-1-(tetrahydropyran-
4-yl)ethyl]-1,2,3,4-
tetrahydroquinoline-6-sulfonic acid (4-
ethylphenyl)isobutylamide compound 40

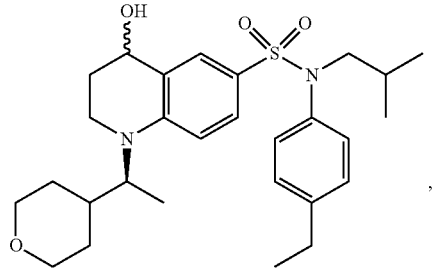

4-hydroxy-1-[(S)-1-(tetrahydropyran-
4-yl)ethyl]-1,2,3,4-
tetrahydroquinoline-6-sulfonic acid (4-
ethylphenyl)isobutylamide -continued compound 41

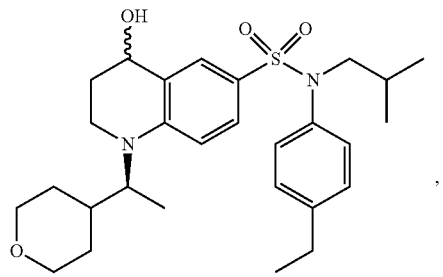

4-hydroxy-1-[(S)-1-(tetrahydropyran-4-yl)ethyl]-1,2,3,4-tetrahydroquinoline-6-sulfonic acid (4-ethylphenyl)isobutylamide compound 42

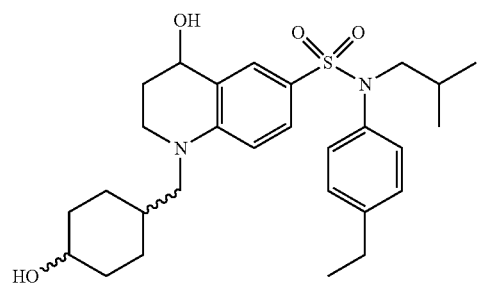

4-hydroxy-1-(4)-hydroxycyclohexylmethyl)-1,2,3,4-tetrahydroquinoline-6-sulfonic acid (4-ethylphenyl)isobutylamide compound 43

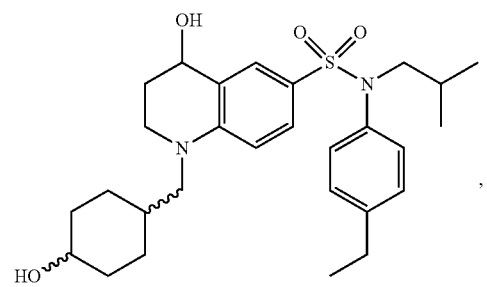

4-hydroxy-1-(4)-hydroxycyclohexylmethyl)-1,2,3,4-tetrahydroquinoline-6-sulfonic acid (4-ethylphenyl)isobutylamide compound 44

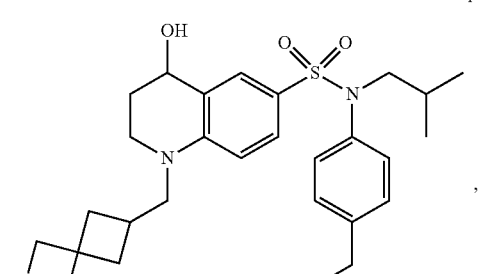

4-hydroxy-1-(2-oxaspiro[3.3]hept-6-ylmethyl-1,2,3,4-tetrahydroquinoline-6-sulfonicacid (4-ethylphenyl)isobutylamide -continued compound 45

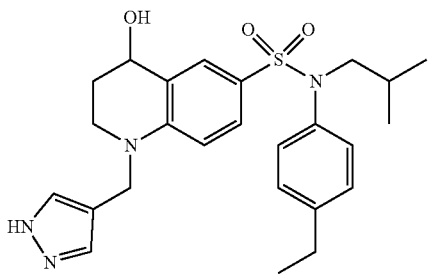

4-hydroxy-1-(1H-pyrazol-4-ylmethyl)-1,2,3,4-tetrahydroquinoline-6-sulfonic acid (4-ethylphenyl)isobutylamide compound 46

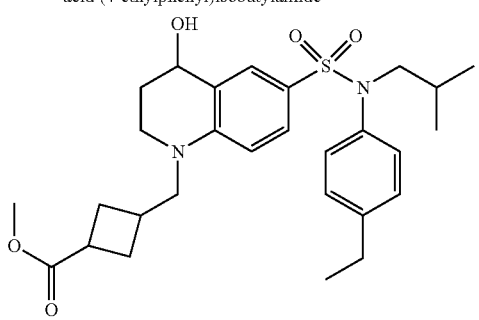

methyl ester of 3-{6-[(4-ethylphenyl)isobutylsulfamoyl]-4-hydroxy-3,4-dihydro-2H-quinolin-1-ylmethyl}azetidine-1-caroxylic acid compound 47

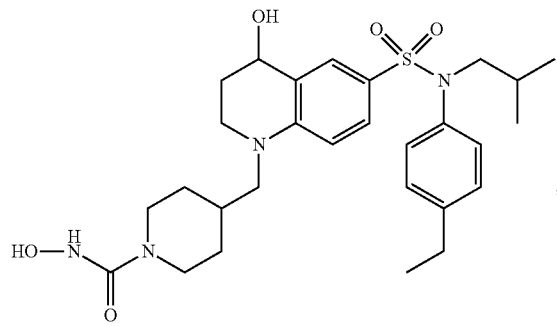

4-{6-[(4-ethylphenyl)isobutylsulfamoyl]-4-hydroxy-3,4-dihydro-2H-quinolin-1-ylmethyl}-N-hydroxybenzamide compound 48

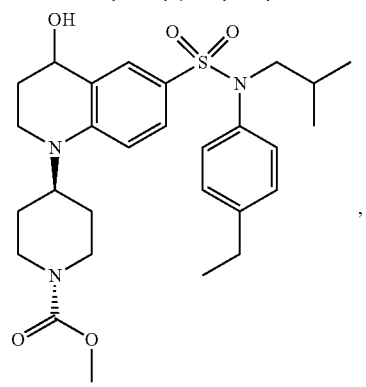

methyl (1R, 4R)- 4-(6-(N-(4-ethylphenyl)-N-isobutylsulfamoyl]-4-hydroxy-3,4-dihydroquinolin-1(2H)-yl)cyclohexane-1-carboxylate -continued

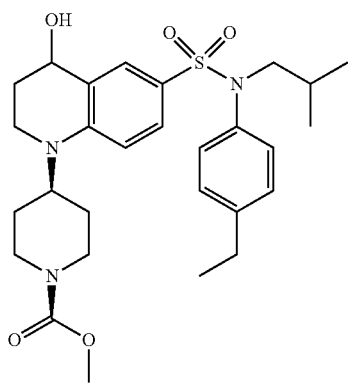

compound 49 methyl (1S, 4S)- 4-(6-(N-(4-ethylphenyl)-N-isobutysulfamoyl]-4-hydroxy-3,4-dihydroquinolin-1(2H)-yl)cyclohexane-1-carboxylate

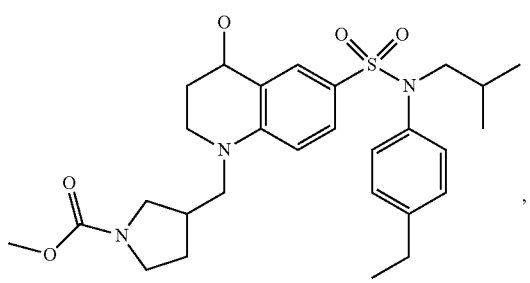

compound 50 methyl ester of 3-{6-[(4-ethylphenyl)isobutylsulfamoyl]-4-hydroxy-3,4-dihydro-2H-quinolin-1-ylmethyl}pyrrolidine-1-carobylic acid

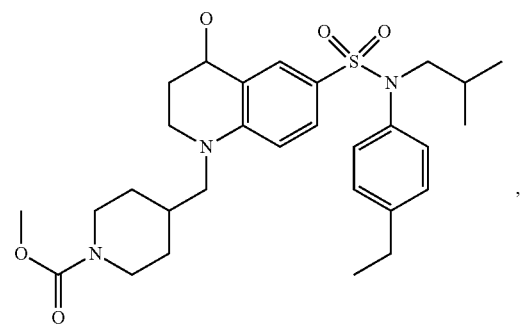

compound 51 methyl ester of carboxylic acid 4-{6-[(4-ethylphenyl)isobutylsufamoyl]-4-hydroxy-3,4-dihydro-2H-quinolin-1-ylmethyl}piperidine-1

-continued

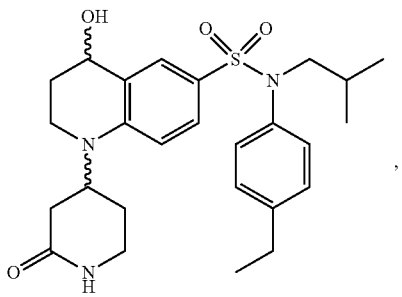

compound 52

Diastereoisomer 1
4-hydroxy-1-(2-oxopiperidin-4-yl)-1,2,3,4-tetrahydroquinoline-6-sulfonic acid (4-ethylphenyl)isobutylamide

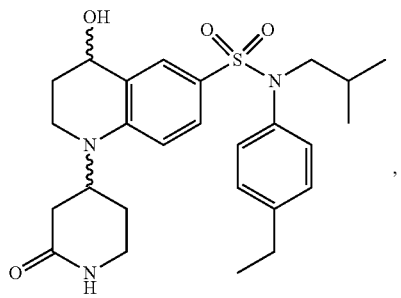

compound 53

Diastereoisomer 2
4-hydroxy-1-(2-oxopiperidin-4-yl)-1,2,3,4-tetrahydroquinoline-6-sulfonic acid (4-ethylphenyl)isobutylamide

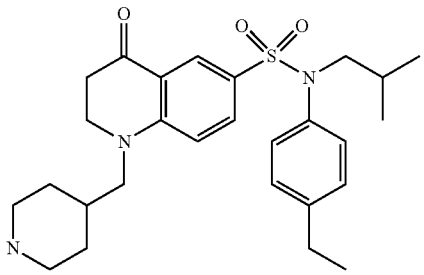

compound 54

4-oxo-1-piperidin-4-ylmethyl)-1,2,3,4-tetrahydroquinoline-6-sulfonic acid (4-ethylphenyl)isobutylamide

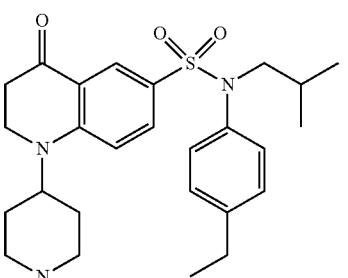

compound 55

4-oxo-1-piperidin-4-yl)-1,2,3,4-tetrahydroquinoline-6-sulfonic acid (4-ethylphenyl)isobutylamide compound 56

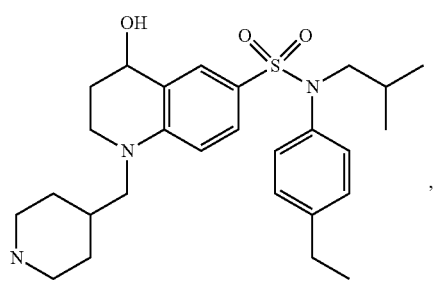

4-hydroxy-1-piperidin-4-ylmethyl)-
1,2,3,4-tetrahydroquinoline-6-sulfonic
acid (4-ethylphenyl)isobutylamide compound 57

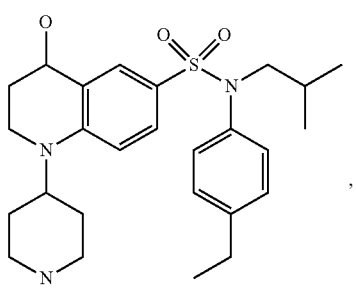

4-hydroxy-1-piperidin-4-yl)-1,2,3,4-
tetrahydroquinoline-6-sulfonic acid (4-
ethylphenyl)isobutylamide compound 58

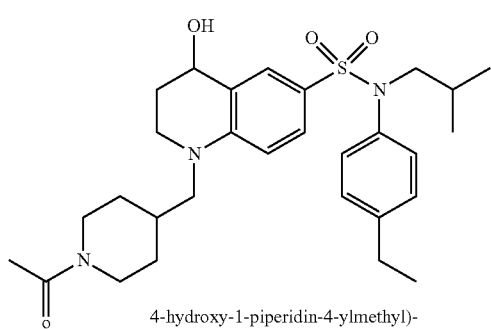

4-hydroxy-1-piperidin-4-ylmethyl)-
1,2,3,4-tetrahydroquinoline-6-sulfonic
acid (4-ethylphenyl)isobutylamide compound 59

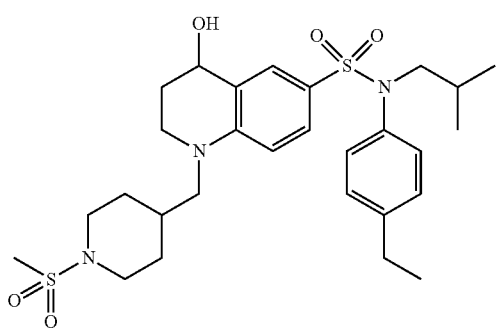

4-hydroxy-1-piperidin-4-ylmethyl)-
1,2,3,4-tetrahydroquinoline-6-sulfonic
acid (4-ethylphenyl)isobutylamide compound 60

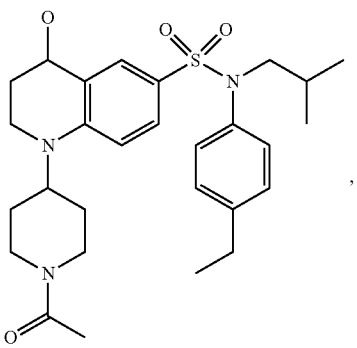

1-(1-acetylpiperidin-4-yl)-oxo-
1,2,3,4-tetrahydroquinoline-6-sulfonic
acid (4-ethylphenyl)isobutylamide compound 61

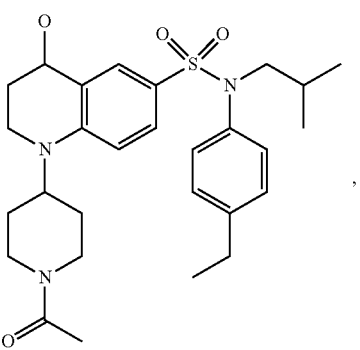

1-(1-acetylpiperidin-4-yl)-4-hydroxy-
1,2,3,4-tetrahydroquinoline-6-sulfonic
acid (4-ethylphenyl)isobutylamide compound 62

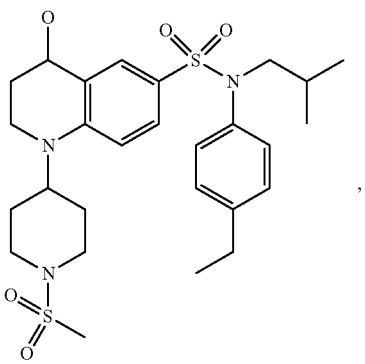

1-(1-acetylpiperidin-4-yl)-4-oxo-
1,2,3,4-tetrahydroquinoline-6-sulfonic
acid (4-ethylphenyl)isobutylamide -continued compound 64

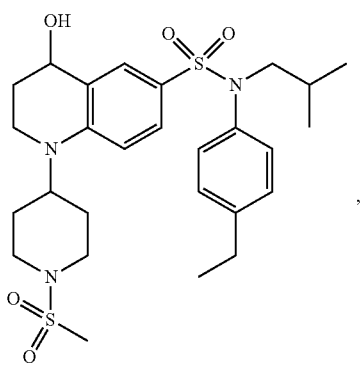

4-hydroxy-1-(1-methanesulfonylpiperidin-4-yl)-1,2,3,4-tetrahydroquinoline-6-sulfonic acid (4-ethylphenyl)isobutylamide compound 65

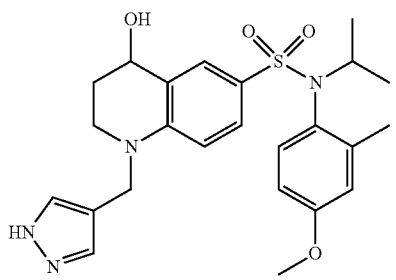

, and 4-hydroxy-1-(4-1H-pyrazol-4-ylmethyl)-1,2,3,4-tetrahydroquinoline-6-sulfonic acid isopropyl(4-methoxy-2-methylphenyl)amide compound 66

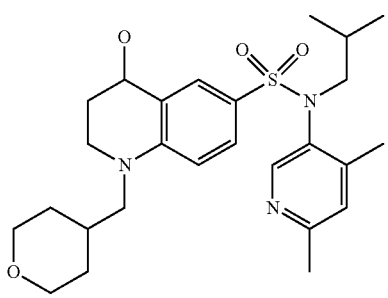

.

4-hydroxy-1-(tetrahydropyran-4-ylmethyl)-1,2,3,4-tetrahydroquinoline-6-sulfonic acid (4,6-dimethylpyridin-3-yl)isobutylamide 10. A medicament comprising an effective amount of the compound as defined by claim 1, or pharmaceutically acceptable addition salt thereof, hydrate thereof, solvate thereof, and/or a mixture thereof, for the therapeutic treatment of RORγt receptor mediated inflammatory disorders, autoimmune diseases, or a combination thereof.

11. A method of treating acne, the method comprising administering an effective amount of the compound as defined by claim 1, or pharmaceutically acceptable addition salt thereof, hydrate thereof, solvate thereof, and/or a mixture thereof, to an individual subject in need thereof.

12. A method of treating psoriasis the method comprising administering an effective amount of the compound as defined by claim 1, or pharmaceutically acceptable addition salt thereof, hydrate thereof, solvate thereof, and/or a mixture thereof, to an individual subject in need thereof.

13. A pharmaceutical composition comprising one or more compounds as defined by claim 1, or pharmaceutically acceptable addition salt thereof, hydrate thereof, solvate thereof, and/or a mixture thereof.

14. The pharmaceutical composition by claim 13, wherein the composition is formulated for topical application.

15. The pharmaceutical composition as defined by claim 14, wherein the composition is for treatment of RORγt receptor mediated inflammatory disorders, autoimmune diseases, or a combination thereof.

16. The pharmaceutical composition as defined in claim 15, wherein the inflammatory disorder and autoimmune disease are selected from the group consisting of acne, atopic dermatitis, psoriasis, and combinations of two or more thereof.

17. The pharmaceutical composition as defined by claim 13 further comprising a pharmaceutically acceptable medium.

18. A pharmaceutical composition comprising one or more compounds according to claim 9.

19. The pharmaceutical composition as defined by claim 18, wherein the composition is for the treatment of RORγt receptor mediated inflammatory disorders, autoimmune diseases, or a combination thereof.

20. The pharmaceutical composition as defined by claim 19, wherein the inflammatory disorder and autoimmune disease are selected from the group consisting of acne, atopic dermatitis, psoriasis, and combinations of two or more thereof.

* * * * *